(12) United States Patent
Zha et al.

(10) Patent No.: US 11,104,721 B2
(45) Date of Patent: Aug. 31, 2021

(54) SURFACE, ANCHORED FC-BAIT ANTIBODY DISPLAY SYSTEM

(71) Applicant: Merck Sharp & Dohme Corp., Rahway, NJ (US)

(72) Inventors: Dongxing Zha, Etna, NH (US); Hussam Hisham Shaheen, Lebanon, NH (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 100 days.

(21) Appl. No.: 16/132,663

(22) Filed: Sep. 17, 2018

(65) Prior Publication Data

US 2019/0040118 A1    Feb. 7, 2019

Related U.S. Application Data

(62) Division of application No. 15/164,773, filed on May 25, 2016, now Pat. No. 10,106,598, which is a
(Continued)

(51) Int. Cl.
*C40B 50/06* (2006.01)
*C07K 16/00* (2006.01)
(Continued)

(52) U.S. Cl.
CPC ............ *C07K 16/00* (2013.01); *C07K 16/005* (2013.01); *C07K 16/32* (2013.01); *C07K 16/40* (2013.01); *G01N 33/6845* (2013.01); *G01N 33/6854* (2013.01); *C07K 2317/14* (2013.01); *C07K 2317/35* (2013.01); *C07K 2317/52* (2013.01); *C07K 2319/00* (2013.01);
(Continued)

(58) Field of Classification Search
None
See application file for complete search history.

(56) References Cited

U.S. PATENT DOCUMENTS

| 2002/0123057 A1 | 9/2002 | Zauderer et al. |
| 2007/0105199 A1 | 5/2007 | Yan et al. |
| (Continued) | | |

FOREIGN PATENT DOCUMENTS

| CN | 1527944 A | 9/2004 |
| EP | 1743938 | 7/2005 |
| (Continued) | | |

OTHER PUBLICATIONS

U.S. Appl. No. 15/164,773, filed May 25, 2016.
(Continued)

*Primary Examiner* — Christian C Boesen
(74) *Attorney, Agent, or Firm* — John David Reilly; Anna L. Cocuzzo

(57) ABSTRACT

The present invention provides, in part, an antibody display system that simultaneously uses a secretion and a display mode. A bait complexed with a monovalent antibody fragment can be expressed on the surface of the host cell wherein the fragment may be assayed for antigen binding while full antibody is simultaneously secreted from the host cell. Methods of using the system for identifying antibodies that bind specifically to an antigen of interest are also provided. Polypeptides, polynucleotides and host cells useful for making the antibody display system are also provided along with methods of use thereof.

5 Claims, 13 Drawing Sheets

Specification includes a Sequence Listing.

Related U.S. Application Data division of application No. 13/990,941, filed as application No. PCT/US2011/062286 on Nov. 29, 2011, now Pat. No. 9,365,846.

(60) Provisional application No. 61/458,771, filed on Dec. 1, 2010.

(51) Int. Cl.
  C07K 16/32 (2006.01)
  C07K 16/40 (2006.01)
  G01N 33/68 (2006.01)
  C40B 30/04 (2006.01)

(52) U.S. Cl.
  CPC ...... C07K 2319/03 (2013.01); C07K 2319/30 (2013.01); C40B 30/04 (2013.01); C40B 50/06 (2013.01); G01N 2440/38 (2013.01)

(56) References Cited

U.S. PATENT DOCUMENTS

| | | |
|---|---|---|
| 2009/0163379 A1 | 6/2009 | Wang et al. |
| 2010/0009866 A1 | 1/2010 | Prinz et al. |
| 2010/0075326 A1 | 3/2010 | Jin |
| 2010/0331192 A1 | 12/2010 | Zha et al. |

FOREIGN PATENT DOCUMENTS

| | | |
|---|---|---|
| WO | WO2008100816 | 8/2008 |
| WO | WO2009111183 | 9/2009 |
| WO | WO2011100566 | 8/2011 |

OTHER PUBLICATIONS

U.S. Appl. No. 13/990,941, filed Aug. 6, 2013.

Shaheen et al., A dual-mode surface system for the maturation and production of monoclonal antibodies in glyco-engineered Pichia pastoris., PLOS ONE, 2013, 1-10, 8-7, US.

Yifan, Liao et al., Research progress of application of yeast surface display technology, Bulletin of Biology, 2009, 4-6 (translation of relevant pages only) 2 pages 44(2).

Yifan, Liao et al., Research progress of application of yeast surface display technology, Bulletin of Biology, 2009, 4-6, 44(2).

BP550-Fc-Sed1p

| | | AX189 Ctrl | Presorted Library | | | | | | Round 2 100nM (S2) Sorted Library | | | | |
|---|---|---|---|---|---|---|---|---|---|---|---|---|---|
| | SID | μg/mL | 2 | 3 | 4 | 5 | 6 | 7 | 8 | 9 | 10 | 11 | 12 |
| Kappa ELISA | A | 250 | 5.2 | 4.3 | 3.9 | 1.5 | 1.9 | 4.8 | 0.4 | 4.1 | 3.1 | 3.2 | 2.4 |
| | B | 83 | 4.0 | 2.1 | 5.9 | 4.5 | 4.7 | 6.8 | 2.3 | 2.5 | 3.6 | 3.8 | 3.8 |
| | C | 27.8 | 4.1 | 2.5 | 4.4 | 6.6 | 3.9 | 6.4 | 7.2 | 3.2 | 2.7 | 2.9 | 3.0 |
| | D | 9.3 | 3.5 | 6.1 | 3.9 | 1.6 | 0.5 | 4.0 | 3.4 | 3.2 | 4.3 | 1.0 | 2.2 |
| | E | 3.1 | 4.1 | 3.8 | 7.5 | 3.4 | 8.4 | 6.2 | 3.3 | 0.4 | 1.5 | 2.9 | 3.0 |
| | F | 10 | 3.5 | 5.3 | 6.8 | 1.8 | 4.0 | 4.1 | 3.1 | 2.7 | 3.7 | 4.3 | 0.4 |
| | G | 0.3 | 2.9 | 4.8 | 5.0 | 2.7 | 3.4 | 2.2 | 2.6 | 4.4 | 5.5 | 6.6 | 3.2 |
| | H | 0.1 | 2.2 | 2.6 | 2.5 | 1.5 | 4.4 | 3.8 | 2.1 | 1.9 | 4.1 | 2.3 | 2.4 |

| | SID | μg/mL | 2 | 3 | 4 | 5 | 6 | 7 | 8 | 9 | 10 | 11 | 12 |
|---|---|---|---|---|---|---|---|---|---|---|---|---|---|
| PCSK9 ELISA | A | 100 | 59.8 | 0.4 | 0.3 | 0.1 | 0.0 | 0.8 | 1.7 | >Max | 267.9 | 243.5 | 34.0 |
| | B | 33 | 147.8 | <Min | 0.3 | <Min | 0.4 | 0.3 | 86.4 | 67.7 | 217.6 | >Max | 49.6 |
| | C | 11.1 | 111.1 | 0.0 | 1.0 | <Min | 0.1 | 2.8 | 309.4 | 74.3 | 252.8 | 797.7 | 32.8 |
| | D | 3.7 | 120.8 | 0.0 | <Min | <Min | <Min | 0.5 | 22.9 | 120.1 | 80.3 | 7.2 | 45.8 |
| | E | 1.2 | 128.3 | 0.1 | 0.2 | <Min | <Min | 0.2 | 53.6 | 0.9 | 26.7 | 181.8 | 231.0 |
| | F | 0.4 | 1370.7 | 22.6 | <Min | <Min | 0.0 | <Min | 55.7 | 85.3 | 87.7 | 371.3 | 0.6 |
| | G | 0.1 | 135.2 | <Min | <Min | <Min | <Min | 1.6 | 105.6 | 463.6 | 195.6 | 585.5 | 118.6 |
| | H | 0.0 | 3353.4 | <Min | <Min | <Min | 0.6 | <Min | 53.6 | 204.8 | 590.3 | 111.7 | 58.1 |

FIG. 7A

BP551-Fc-Sed1p

| | | AX189 Ctrl | Presorted Library | | | | | | Round 2 100nM (S2) Sorted Library | | | | |
|---|---|---|---|---|---|---|---|---|---|---|---|---|---|
| | SID | μg/mL | 2 | 3 | 4 | 5 | 6 | 7 | 8 | 9 | 10 | 11 | 12 |
| Kappa ELISA | A | 250 | 5.0 | 5.4 | 0.9 | 2.3 | 0.3 | 1.4 | 5.9 | 3.6 | 4.3 | 5.0 | 4.9 |
| | B | 83 | 5.1 | 2.4 | 0.1 | 2.9 | 2.0 | 4.5 | 3.2 | 2.9 | 7.9 | 5.9 | 2.8 |
| | C | 27.8 | 4.0 | 4.9 | 1.9 | 3.7 | 3.6 | 3.9 | 3.5 | 0.2 | 0.1 | 8.6 | 0.1 |
| | D | 9.3 | 3.7 | 5.5 | 3.3 | 1.9 | 3.7 | 0.1 | 7.2 | 7.4 | 0.1 | 5.4 | 0.1 |
| | E | 3.1 | 5.0 | 0.3 | 0.2 | 3.0 | 3.8 | 2.8 | 2.9 | 3.9 | 4.8 | 4.4 | 3.5 |
| | F | 10 | 2.7 | 0.1 | 3.2 | 3.8 | 3.5 | 3.9 | 6.4 | 2.8 | 4.7 | 6.3 | 4.3 |
| | G | 0.3 | 2.8 | 0.1 | 1.9 | 2.1 | 2.0 | 3.4 | 3.9 | 3.0 | 2.6 | 2.7 | 3.5 |
| | H | 0.1 | 2.2 | 1.9 | 0.3 | 1.4 | 1.5 | 1.5 | 2.4 | 1.7 | 4.5 | 3.9 | 3.9 |

| | SID | μg/mL | 2 | 3 | 4 | 5 | 6 | 7 | 8 | 9 | 10 | 11 | 12 |
|---|---|---|---|---|---|---|---|---|---|---|---|---|---|
| PCSK9 ELISA | A | 100 | 73.3 | 15.4 | 0.5 | 0.0 | 0.2 | 0.3 | 281.9 | 170.6 | 58.2 | 49.9 | 55.3 |
| | B | 33 | 202.0 | 0.4 | 0.1 | 0.1 | 0.3 | 0.4 | 210.7 | 147.9 | 720.9 | 228.1 | 32.7 |
| | C | 11.1 | 102.6 | 0.5 | 1.3 | 8.1 | 0.0 | 1.6 | 42.9 | 167.5 | 83.7 | 855.9 | 138.5 |
| | D | 3.7 | 143.5 | 0.0 | <Min | 0.1 | 0.0 | 0.1 | 97.3 | >Max | 592.4 | 67.2 | 115.6 |
| | E | 1.2 | 207.1 | 0.1 | 0.2 | 0.0 | 0.6 | 0.2 | 14.1 | 249.2 | 252.6 | 190.0 | 270.1 |
| | F | 0.4 | 173.0 | 0.0 | <Min | <Min | 9.3 | 9.5 | 132.3 | 32.5 | 43.3 | 286.8 | 87.0 |
| | G | 0.1 | 93.3 | 0.2 | 0.1 | 0.1 | 0.2 | 0.9 | 296.2 | 108.8 | 33.6 | 48.6 | 181.1 |
| | H | 0.0 | 95.4 | <Min | <Min | <Min | 0.1 | <Min | 125.6 | 42.8 | 172.3 | 150.6 | 70.5 |

SEQUENCE LISTING

<160> NUMBER OF SEQ ID NOS: 7

<210> SEQ ID NO 1
<211> LENGTH: 226
<212> TYPE: PRT
<213> ORGANISM: Homo sapiens

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 2
<211> LENGTH: 322
<212> TYPE: PRT
<213> ORGANISM: Saccharomyces cerevisiae

<400> SEQUENCE: 2

Val Asp Gln Phe Ser Asn Ser Thr Ser Ala Ser Ser Thr Asp Val Thr
1               5                   10                  15

Ser Ser Ser Ser Ile Ser Thr Ser Ser Gly Ser Val Thr Ile Thr Ser
            20                  25                  30

Ser Glu Ala Pro Glu Ser Asp Asn Gly Thr Ser Thr Ala Ala Pro Thr
        35                  40                  45

Glu Thr Ser Thr Glu Ala Pro Thr Thr Ala Ile Pro Thr Asn Gly Thr
    50                  55                  60

Ser Thr Glu Ala Pro Thr Thr Ala Ile Pro Thr Asn Gly Thr Ser Thr
65                  70                  75                  80

Glu Ala Pro Thr Asp Thr Thr Thr Glu Ala Pro Thr Thr Ala Leu Pro

-continued

```
                85                  90                  95
Thr Asn Gly Thr Ser Thr Glu Ala Pro Thr Asp Thr Thr Glu Ala
            100                 105                 110
Pro Thr Thr Gly Leu Pro Thr Asn Gly Thr Thr Ser Ala Phe Pro Pro
            115                 120                 125
Thr Thr Ser Leu Pro Pro Ser Asn Thr Thr Thr Thr Pro Pro Tyr Asn
    130                 135                 140
Pro Ser Thr Asp Tyr Thr Thr Asp Tyr Thr Val Val Thr Glu Tyr Thr
145                 150                 155                 160
Thr Tyr Cys Pro Glu Pro Thr Thr Phe Thr Thr Asn Gly Lys Thr Tyr
                165                 170                 175
Thr Val Thr Glu Pro Thr Thr Leu Thr Ile Thr Asp Cys Pro Cys Thr
            180                 185                 190
Ile Glu Lys Pro Thr Thr Thr Ser Thr Thr Glu Tyr Thr Val Val Thr
        195                 200                 205
Glu Tyr Thr Thr Tyr Cys Pro Glu Pro Thr Thr Phe Thr Thr Asn Gly
    210                 215                 220
Lys Thr Tyr Thr Val Thr Glu Pro Thr Thr Leu Thr Ile Thr Asp Cys
225                 230                 235                 240
Pro Cys Thr Ile Glu Lys Ser Glu Ala Pro Glu Ser Ser Val Pro Val
                245                 250                 255
Thr Glu Ser Lys Gly Thr Thr Thr Lys Glu Thr Gly Val Thr Thr Lys
            260                 265                 270
Gln Thr Thr Ala Asn Pro Ser Leu Thr Val Ser Thr Val Pro Val
    275                 280                 285
Ser Ser Ser Ala Ser Ser His Ser Val Val Ile Asn Ser Asn Gly Ala
    290                 295                 300
Asn Val Val Val Pro Gly Ala Leu Gly Leu Ala Gly Val Ala Met Leu
305                 310                 315                 320
Phe Leu
```

<210> SEQ ID NO 3
<211> LENGTH: 19
<212> TYPE: PRT
<213> ORGANISM: Homo sapiens

<400> SEQUENCE: 3

```
Met Arg Phe Pro Ser Ile Phe Thr Ala Val Leu Phe Ala Ala Ser Ser
1               5                   10                  15
Ala Leu Ala
```

<210> SEQ ID NO 4
<211> LENGTH: 570
<212> TYPE: PRT
<213> ORGANISM: Artificial Sequence
<220> FEATURE:
<223> OTHER INFORMATION: Homo sapiens and Saccharmomyces cerevisiae

<400> SEQUENCE: 4

```
Met Arg Phe Pro Ser Ile Phe Thr Ala Val Leu Phe Ala Ala Ser Ser
1               5                   10                  15
Ala Leu Ala Asp Lys Thr His Thr Cys Pro Pro Cys Pro Ala Pro Glu
            20                  25                  30
Leu Leu Gly Gly Pro Ser Val Phe Leu Phe Pro Pro Lys Pro Lys Asp
        35                  40                  45
Thr Leu Met Ile Ser Arg Thr Pro Glu Val Thr Cys Val Val Val Asp
```

-continued

```
            50                  55                  60
Val Ser His Glu Asp Pro Glu Val Lys Phe Asn Trp Tyr Val Asp Gly
 65                  70                  75                  80

Val Glu Val His Asn Ala Lys Thr Lys Pro Arg Glu Glu Gln Tyr Asn
                 85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
        130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
210                 215                 220

Ser Val Met His Glu Ala Leu His Asn His Tyr Thr Gln Lys Ser Leu
225                 230                 235                 240

Ser Leu Ser Pro Gly Gly Gly Val Asp Gln Phe Ser Asn Ser Thr
                245                 250                 255

Ser Ala Ser Ser Thr Asp Val Thr Ser Ser Ser Ile Ser Thr Ser
            260                 265                 270

Ser Gly Ser Val Thr Ile Thr Ser Ser Glu Ala Pro Glu Ser Asp Asn
        275                 280                 285

Gly Thr Ser Thr Ala Ala Pro Thr Glu Thr Ser Thr Glu Ala Pro Thr
        290                 295                 300

Thr Ala Ile Pro Thr Asn Gly Thr Ser Thr Glu Ala Pro Thr Thr Ala
305                 310                 315                 320

Ile Pro Thr Asn Gly Thr Ser Thr Glu Ala Pro Thr Asp Thr Thr Thr
                325                 330                 335

Glu Ala Pro Thr Thr Ala Leu Pro Thr Asn Gly Thr Ser Thr Glu Ala
            340                 345                 350

Pro Thr Asp Thr Thr Thr Glu Ala Pro Thr Gly Leu Pro Thr Asn
        355                 360                 365

Gly Thr Thr Ser Ala Phe Pro Pro Thr Thr Ser Leu Pro Pro Ser Asn
        370                 375                 380

Thr Thr Thr Thr Pro Pro Tyr Asn Pro Ser Thr Asp Tyr Thr Thr Asp
385                 390                 395                 400

Tyr Thr Val Val Thr Glu Tyr Thr Thr Tyr Cys Pro Glu Pro Thr Thr
                405                 410                 415

Phe Thr Thr Asn Gly Lys Thr Tyr Thr Val Thr Glu Pro Thr Thr Leu
            420                 425                 430

Thr Ile Thr Asp Cys Pro Cys Thr Ile Glu Lys Pro Thr Thr Thr Ser
        435                 440                 445

Thr Thr Glu Tyr Thr Val Val Thr Glu Tyr Thr Thr Tyr Cys Pro Glu
        450                 455                 460

Pro Thr Thr Phe Thr Thr Asn Gly Lys Thr Tyr Thr Val Thr Glu Pro
465                 470                 475                 480
```

```
Thr Thr Leu Thr Ile Thr Asp Cys Pro Cys Thr Ile Glu Lys Ser Glu
            485                 490                 495

Ala Pro Glu Ser Ser Val Pro Val Thr Glu Ser Lys Gly Thr Thr Thr
        500                 505                 510

Lys Glu Thr Gly Val Thr Thr Lys Gln Thr Thr Ala Asn Pro Ser Leu
        515                 520                 525

Thr Val Ser Thr Val Val Pro Val Ser Ser Ala Ser Ser His Ser
        530                 535                 540

Val Val Ile Asn Ser Asn Gly Ala Asn Val Val Pro Gly Ala Leu
545                 550                 555                 560

Gly Leu Ala Gly Val Ala Met Leu Phe Leu
            565                 570

<210> SEQ ID NO 5
<211> LENGTH: 8640
<212> TYPE: DNA
<213> ORGANISM: Artificial Sequence
<220> FEATURE:
<223> OTHER INFORMATION: Plasmid pGLY3033

<400> SEQUENCE: 5
```

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | gagatctaac | atccaaagac | 420 |
| gaaaggttga | atgaaacctt | tttgccatcc | gacatccaca | ggtccattct | cacacataag | 480 |
| tgccaaacgc | aacaggaggg | gatacactag | cagcagaccg | ttgcaaacgc | aggacctcca | 540 |
| ctcctcttct | cctcaacacc | cacttttgcc | atcgaaaaac | cagcccagtt | attgggcttg | 600 |
| attggagctc | gctcattcca | attccttcta | ttaggctact | aacaccatga | ctttattagc | 660 |
| ctgtctatcc | tggccccct | ggcgaggttc | atgtttgttt | atttccgaat | gcaacaagct | 720 |
| ccgcattaca | cccgaacatc | actccagatg | agggctttct | gagtgtgggg | tcaaatagtt | 780 |
| tcatgttccc | caaatggccc | aaaactgaca | gtttaaacgc | tgtcttggaa | cctaatatga | 840 |
| caaaagcgtg | atctcatcca | agatgaacta | agtttggttc | gttgaaatgc | taacggccag | 900 |
| ttggtcaaaa | agaaacttcc | aaaagtcggc | ataccgtttg | tcttgtttgg | tattgattga | 960 |
| cgaatgctca | aaaataatct | cattaatgct | tagcgcagtc | tctctatcgc | ttctgaaccc | 1020 |
| cggtgcacct | gtgccgaaac | gcaaatgggg | aaacacccgc | tttttggatg | attatgcatt | 1080 |
| gtctccacat | tgtatgcttc | caagattctg | gtgggaatac | tgctgatagc | ctaacgttca | 1140 |
| tgatcaaaat | ttaactgttc | taaccccctac | ttgacagcaa | tatataaaca | gaaggaagct | 1200 |
| gccctgtctt | aaacctttt | ttttatcatc | attattagct | tactttcata | attgcgactg | 1260 |
| gttccaattg | acaagctttt | gattttaacg | acttttaacg | acaacttgag | aagatcaaaa | 1320 |
| aacaactaat | tattcgaaac | ggaattcacg | atggtcgctt | ggtggtcttt | gtttctgtac | 1380 |
| ggtcttcagg | tcgctgcacc | tgctttggct | acttccagat | ggagggatt | gcaatccgaa | 1440 |
| aaccacagat | tgagaatgaa | gatcactgag | ttggacaagg | acttggagga | agttactatg | 1500 |

```
cagttgcagg atgttggtgg ttgtgagcag aagttgatct ccgaagagga tttggtcgac    1560
caattctcta actctacttc cgcttcctct actgacgtta cttcctcctc ctctatttct    1620
acttcctccg gttccgttac tattacttcc tctgaggctc cagaatctga caacggtact    1680
tctactgctg ctccaactga aacttctact gaggctccta ctactgctat tccaactaac    1740
ggaacttcca cagaggctcc aacaacagct atccctacaa acggtacatc cactgaagct    1800
cctactgaca ctactacaga agctccaact actgctttgc ctactaatgg tacatcaaca    1860
gaggctccta cagatacaac aactgaagct ccaacaactg gattgccaac aaacggtact    1920
acttctgctt tcccaccaac tacttccttg ccaccatcca acactactac tactccacca    1980
tacaacccat ccactgacta cactactgac tacacagttg ttactgagta cactacttac    2040
tgtccagagc caactacttt cacaacaaac ggaaagactt acactgttac tgagcctact    2100
actttgacta tcactgactg tccatgtact atcgagaagc caactactac ttccactaca    2160
gagtatactg ttgttacaga atacacaaca tattgtcctg agccaacaac attcactact    2220
aatggaaaaa catacacagt tacagaacca actacattga caattacaga ttgtccttgt    2280
acaattgaga agtccgaggc tcctgaatct tctgttccag ttactgaatc caagggtact    2340
actactaaag aaactggtgt tactactaag cagactactc taacccatc cttgactgtt    2400
tccactgttg ttccagtttc ttcctctgct tcttcccact ccgttgttat caactccaac    2460
ggtgctaacg ttgttgttcc tggtgctttg ggattggctg gtgttgctat gttgttcttg    2520
taatagggcc ggccatttaa atacaggccc cttttccttt gtcgatatca tgtaattagt    2580
tatgtcacgc ttacattcac gccctcctcc cacatccgct ctaaccgaaa aggaaggagt    2640
tagacaacct gaagtctagg tccctattta tttttttttaa tagttatgtt agtattaaga    2700
acgttattta tatttcaaat ttttcttttt tttctgtaca aacgcgtgta cgcatgtaac    2760
attatactga aaaccttgct tgagaaggtt ttgggacgct cgaaggcttt aatttgcaag    2820
ctggatccgc ggccgcttac gcgccgttct tcgcttggtc ttgtatctcc ttacactgta    2880
tcttcccatt tgcgtttagg tggttatcaa aaactaaaag gaaaaatttc agatgtttat    2940
ctctaaggtt ttttcttttt acagtataac acgtgatgcg tcacgtggta ctagattacg    3000
taagttattt tggtccggtg ggtaagtggg taagaataga aagcatgaag gtttacaaaa    3060
acgcagtcac gaattattgc tacttcgagc ttggaaccac cccaaagatt atattgtact    3120
gatgcactac cttctcgatt ttgctcctcc aagaacctac gaaaaacatt tcttgagcct    3180
tttcaaccta gactacacat caagttattt aaggtatgtt ccgttaacat gtaagaaaag    3240
gagaggatag atcgtttatg gggtacgtcg cctgattcaa gcgtgaccat cgaagaata    3300
ggccttcgaa agctgaataa agcaaatgtc agttgcgatt ggtatgctga caaattagca    3360
taaaaagcaa tagactttct aaccacctgt ttttttcctt ttactttatt tatattttgc    3420
caccgtacta acaagttcag acaaattaat taacaccatg tcagaagatc aaaaagtga    3480
aaattccgta ccttctaagg ttaatatggt gaatcgcacc gatatactga ctacgatcaa    3540
gtcattgtca tggcttgact tgatgttgcc atttactata attctctcca taatcattgc    3600
agtaataatt tctgtctatg tgccttcttc ccgtcacact tttgacgctg aaggtcatcc    3660
caatctaatg ggagtgtcca ttcctttgac tgttggtatg attgtaatga tgattccccc    3720
gatctgcaaa gtttcctggg agtctattca caagtacttc tacaggagct atataaggaa    3780
gcaactagcc ctctcgttat ttttgaattg ggtcatcggc cctttgttga tgacagcatt    3840
ggcgtggatg gcgctattcg attataagga ataccgtcaa ggcattatta tgatcggagt    3900
```

```
agctagatgc attgccatgg tgctaatttg gaatcagatt gctggaggag acaatgatct    3960
ctgcgtcgtg cttgttatta caaactcgct tttacagatg gtattatatg caccattgca    4020
gatattttac tgttatgtta tttctcatga ccacctgaat acttcaaata gggtattatt    4080
cgaagaggtt gcaaagtctg tcggagtttt tctcggcata ccactgggaa ttggcattat    4140
catacgtttg ggaagtctta ccatagctgg taaaagtaat tatgaaaaat acattttgag    4200
atttatttct ccatgggcaa tgatcggatt tcattacact ttatttgtta ttttattag    4260 tagaggttat caatttatcc acgaaattgg ttctgcaata ttgtgctttg tcccattggt    4320
gctttacttc tttattgcat ggttttgac cttcgcatta atgaggtact tatcaatatc    4380
taggagtgat acacaaagag aatgtagctg tgaccaagaa ctacttttaa agagggtctg    4440
gggaagaaag tcttgtgaag ctagcttttc tattacgatg acgcaatgtt tcactatggc    4500
ttcaaataat tttgaactat ccctggcaat tgctatttcc ttatatggta acaatagcaa    4560
gcaagcaata gctgcaacat ttgggccgtt gctagaagtt ccaattttat tgattttggc    4620
aatagtcgcg agaatcctta aaccatatta tatatggaac aatagaaatt aattaacagg    4680
ccccttttcc tttgtcgata tcatgtaatt agttatgtca cgcttacatt cacgccctcc    4740
tcccacatcc gctctaaccg aaaaggaagg agttagacaa cctgaagtct aggtccctat    4800 ttatttttt taatagttat gttagtatta agaacgttat ttatatttca aattttctt    4860 ttttttctgt acaaacgcgt gtacgcatgt aacattatac tgaaaacctt gcttgagaag    4920
gttttgggac gctcgaaggc tttaatttgc aagctgcggc ctaaggcgcg ccaggccata    4980
atggcccaaa tgcaagagga cattagaaat gtgtttggta agaacatgaa gccggaggca    5040
tacaaacgat tcacagattt gaaggaggaa acaaaactgc atccaccgga agtgccagca    5100
gccgtgtatg ccaaccttgc tctcaaaggc attcctacgg atctgagtgg gaaatatctg    5160
agattcacag cccactatt ggaacagtac caaacctagt ttggccgatc catgattatg    5220
taatgcatat agttttgtc gatgctcacc cgtttcgagt ctgtctcgta tcgtcttacg    5280
tataagttca agcatgttta ccaggtctgt tagaaactcc tttgtgaggg caggacctat    5340
tcgtctcggt cccgttgttt ctaagagact gtacagccaa gcgcagaatg gtggcattaa    5400
ccataagagg attctgatcg gacttggtct attggctatt ggaaccaccc tttacgggac    5460
aaccaaccct accaagactc ctattgcatt tgtggaacca gccacggaaa gagcgtttaa    5520
ggacggagac gtctctgtga ttttgttct cggaggtcca ggagctggaa aaggtaccca    5580
atgtgccaaa ctagtgagta attacggatt tgttcacctg tcagctggag acttgttacg    5640
tgcagaacag aagagggagg ggtctaagta tggagagatg atttcccagt atatcagaga    5700
tggactgata gtacctcaag aggtcaccat tgcgctcttg gagcaggcca tgaaggaaaa    5760
cttcgagaaa gggaagacac ggttcttgat tgatggattc cctcgtaaga tggaccaggc    5820
caaaactttt gaggaaaaag tcgcaaagtc caaggtgaca ctttctcttg attgtcccga    5880
atcagtgctc cttgagagat tacttaaaag aggacagaca agcggaagag aggatgataa    5940
tgcggagagt atcaaaaaaa gattcaaaac attcgtggaa acttcgatgc ctgtggtgga    6000
ctatttcggg aagcaaggac gcgttttgaa ggtatcttgt gaccaccctg tggatcaagt    6060
gtattcacag gttgtgtcgg tgctaaaaga gaagggatc tttgccgata acgagacgga    6120
gaataaataa acattgtaat aagatttaga ctgtgaatgt tctatgtaat attttttcgag    6180 atactgtatc tatctggtgt accgtatcac tctggacttg caaactcatt gattacttgt    6240
```

```
gcaatgggca agaaggatag ctctagaaag aagaagaaaa aggagccgcc tgaagagctg      6300
gatctttccg aggttgttcc aacttttggt tatgaggaat ttcatgttga gcaagaggag      6360
aatccggtcg atcaagacga acttgacggc cataatggcc tagcttggcg taatcatggt      6420
catagctgtt tcctgtgtga aattgttatc cgctcacaat tccacacaac atacgagccg      6480
gaagcataaa gtgtaaagcc tggggtgcct aatgagtgag ctaactcaca ttaattgcgt      6540
tgcgctcact gcccgctttc cagtcgggaa acctgtcgtg ccagctgcat taatgaatcg      6600
gccaacgcgc ggggagaggc ggtttgcgta ttgggcgctc ttccgcttcc tcgctcactg      6660
actcgctgcg ctcggtcgtt cggctgcggc gagcggtatc agctcactca aaggcggtaa      6720
tacggttatc cacagaatca ggggataacg caggaaagaa catgtgagca aaaggccagc      6780
aaaaggccag gaaccgtaaa aaggccgcgt tgctggcgtt tttccatagg ctccgccccc      6840
ctgacgagca tcacaaaaat cgacgctcaa gtcagaggtg gcgaaacccg acaggactat      6900
aaagatacca ggcgtttccc cctggaagct ccctcgtgcg ctctcctgtt ccgaccctgc      6960
cgcttaccgg atacctgtcc gcctttctcc cttcgggaag cgtggcgctt tctcatagct      7020
cacgctgtag gtatctcagt tcggtgtagg tcgttcgctc caagctgggc tgtgtgcacg      7080
aaccccccgt tcagcccgac cgctgcgcct tatccggtaa ctatcgtctt gagtccaacc      7140
cggtaagaca cgacttatcg ccactggcag cagccactgg taacaggatt agcagagcga      7200
ggtatgtagg cggtgctaca gagttcttga agtggtggcc taactacggc tacactagaa      7260
ggacagtatt tggtatctgc gctctgctga agccagttac cttcggaaaa agagttggta      7320
gctcttgatc cggcaaacaa accaccgctg gtagcggtgg tttttttgtt tgcaagcagc      7380
agattacgcg cagaaaaaaa ggatctcaag aagatccttt gatcttttct acggggtctg      7440
acgctcagtg gaacgaaaac tcacgttaag ggattttggt catgagatta tcaaaaagga      7500
tcttcaccta gatcctttta aattaaaaat gaagttttaa atcaatctaa agtatatatg      7560
agtaaacttg gtctgacagt taccaatgct taatcagtga ggcacctatc tcagcgatct      7620
gtctatttcg ttcatccata gttgcctgac tccccgtcgt gtagataact acgatacggg      7680
agggcttacc atctggcccc agtgctgcaa tgataccgcg agaccacgc tcaccggctc      7740 cagatttatc agcaataaac cagccagccg gaagggccga gcgcagaagt ggtcctgcaa      7800
ctttatccgc ctccatccag tctattaatt gttgccggga agctagagta agtagttcgc      7860
cagttaatag tttgcgcaac gttgttgcca ttgctacagg catcgtggtg tcacgctcgt      7920
cgtttggtat ggcttcattc agctccggtt cccaacgatc aaggcgagtt acatgatccc      7980
ccatgttgtg caaaaaagcg gttagctcct tcggtcctcc gatcgttgtc agaagtaagt      8040
tggccgcagt gttatcactc atggttatgg cagcactgca taattctctt actgtcatgc      8100
catccgtaag atgcttttct gtgactggtg agtactcaac caagtcattc tgagaatagt      8160
gtatgcggcg accgagttgc tcttgcccgg cgtcaatacg ggataatacc gcgccacata      8220
gcagaacttt aaaagtgctc atcattggaa aacgttcttc ggggcgaaaa ctctcaagga      8280
tcttaccgct gttgagatcc agttcgatgt aacccactcg tgcacccaac tgatcttcag      8340
catcttttac tttcaccagc gtttctgggt gagcaaaaac aggaaggcaa aatgccgcaa      8400
aaaagggaat aagggcgaca cggaaatgtt gaatactcat actcttcctt tttcaatatt      8460
attgaagcat ttatcagggt tattgtctca tgagcggata catatttgaa tgtatttaga      8520
aaaataaaca aataggggtt ccgcgcacat ttccccgaaa agtgccacct gacgtctaag      8580
aaaccattat tatcatgaca ttaacctata aaaataggcg tatcacgagg ccctttcgtc      8640
```

<210> SEQ ID NO 6
<211> LENGTH: 9180
<212> TYPE: PRT
<213> ORGANISM: Artificial Sequence
<220> FEATURE:
<223> OTHER INFORMATION: Plasmid pGLY9008

<400> SEQUENCE: 6

```
Thr Cys Gly Cys Gly Cys Gly Thr Thr Cys Gly Gly Thr Gly Ala
1               5                   10                  15

Thr Gly Ala Cys Gly Gly Thr Gly Ala Ala Ala Cys Cys Thr Cys
            20                  25                  30

Thr Gly Ala Cys Ala Cys Ala Thr Gly Cys Ala Gly Cys Thr Cys Cys
            35                  40                  45

Cys Gly Gly Ala Gly Ala Cys Gly Gly Thr Cys Ala Cys Ala Gly Cys
        50                  55                  60

Thr Thr Gly Thr Cys Thr Gly Thr Ala Ala Gly Cys Gly Gly Ala Thr
65                  70                  75                  80

Gly Cys Cys Gly Gly Gly Ala Gly Cys Ala Gly Ala Cys Ala Ala Gly
                85                  90                  95

Cys Cys Cys Gly Thr Cys Ala Gly Gly Gly Cys Gly Cys Gly Thr Cys
                100                 105                 110

Ala Gly Cys Gly Gly Gly Thr Gly Thr Thr Gly Gly Cys Gly Gly Gly
            115                 120                 125

Thr Gly Thr Cys Gly Gly Gly Gly Cys Thr Gly Gly Cys Thr Thr Ala
        130                 135                 140

Ala Cys Thr Ala Thr Gly Cys Gly Gly Cys Ala Thr Cys Ala Gly Ala
145                 150                 155                 160

Gly Cys Ala Gly Ala Thr Thr Gly Thr Ala Cys Thr Gly Ala Gly Ala
                165                 170                 175

Gly Thr Gly Cys Ala Cys Cys Ala Thr Ala Thr Gly Cys Gly Gly Thr
            180                 185                 190

Gly Thr Gly Ala Ala Ala Thr Ala Cys Cys Gly Cys Ala Cys Ala Gly
        195                 200                 205

Ala Thr Gly Cys Gly Thr Ala Ala Gly Gly Ala Gly Ala Ala Ala Ala
            210                 215                 220

Thr Ala Cys Cys Gly Cys Ala Thr Cys Ala Gly Gly Cys Gly Cys Cys
225                 230                 235                 240

Ala Thr Thr Cys Gly Cys Cys Ala Thr Thr Cys Ala Gly Gly Cys Thr
                245                 250                 255

Gly Cys Gly Cys Ala Ala Cys Thr Gly Thr Thr Gly Gly Gly Ala Ala
            260                 265                 270

Gly Gly Gly Cys Gly Ala Thr Cys Gly Gly Thr Gly Cys Gly Gly Gly
        275                 280                 285

Cys Cys Thr Cys Thr Thr Cys Gly Cys Thr Ala Thr Thr Ala Cys Gly
    290                 295                 300

Cys Cys Ala Gly Cys Thr Gly Gly Cys Gly Ala Ala Ala Gly Gly Gly
305                 310                 315                 320

Gly Gly Ala Thr Gly Thr Gly Cys Thr Gly Cys Ala Ala Gly Gly Cys
                325                 330                 335

Gly Ala Thr Thr Ala Ala Gly Thr Thr Gly Gly Gly Thr Ala Ala Cys
            340                 345                 350

Gly Cys Cys Ala Gly Gly Gly Thr Thr Thr Thr Cys Cys Cys Ala Gly
        355                 360                 365
```

```
Thr Cys Ala Cys Gly Ala Cys Gly Thr Thr Gly Thr Ala Ala Ala Ala
    370                 375                 380

Cys Gly Ala Cys Gly Gly Cys Cys Ala Gly Thr Gly Ala Ala Thr Thr
385                 390                 395                 400

Gly Ala Gly Ala Thr Cys Thr Ala Ala Cys Ala Thr Cys Cys Ala Ala
                405                 410                 415

Ala Gly Ala Cys Gly Ala Ala Ala Gly Gly Thr Thr Gly Ala Ala Thr
            420                 425                 430

Gly Ala Ala Ala Cys Cys Thr Thr Thr Thr Thr Gly Cys Cys Ala Thr
        435                 440                 445

Cys Cys Gly Ala Cys Ala Thr Cys Cys Ala Cys Ala Gly Gly Thr Cys
    450                 455                 460

Cys Ala Thr Thr Cys Thr Cys Ala Cys Ala Cys Ala Thr Ala Ala Gly
465                 470                 475                 480

Thr Gly Cys Cys Ala Ala Ala Cys Gly Cys Ala Ala Cys Ala Gly Gly
                485                 490                 495

Ala Gly Gly Gly Gly Ala Thr Ala Cys Ala Cys Thr Ala Gly Cys Ala
            500                 505                 510

Gly Cys Ala Gly Ala Cys Cys Gly Thr Thr Gly Cys Ala Ala Ala Cys
        515                 520                 525

Gly Cys Ala Gly Gly Ala Cys Cys Thr Cys Cys Ala Cys Thr Cys Cys
    530                 535                 540

Thr Cys Thr Thr Cys Thr Cys Cys Thr Cys Ala Ala Cys Ala Cys Cys
545                 550                 555                 560

Cys Ala Cys Thr Thr Thr Thr Gly Cys Cys Ala Thr Cys Gly Ala Ala
                565                 570                 575

Ala Ala Ala Cys Cys Ala Gly Cys Cys Cys Ala Gly Thr Thr Ala Thr
            580                 585                 590

Thr Gly Gly Gly Cys Thr Thr Gly Ala Thr Thr Gly Gly Ala Gly Cys
        595                 600                 605

Thr Cys Gly Cys Thr Cys Ala Thr Thr Cys Cys Ala Ala Thr Thr Cys
    610                 615                 620

Cys Thr Thr Cys Thr Ala Thr Thr Ala Gly Gly Cys Thr Ala Cys Thr
625                 630                 635                 640

Ala Ala Cys Ala Cys Cys Ala Thr Gly Ala Cys Thr Thr Thr Ala Thr
                645                 650                 655

Thr Ala Gly Cys Cys Thr Gly Thr Cys Thr Ala Thr Cys Cys Thr Gly
            660                 665                 670

Gly Cys Cys Cys Cys Cys Cys Thr Gly Gly Cys Gly Ala Gly Gly Thr
        675                 680                 685

Thr Cys Ala Thr Gly Thr Thr Thr Gly Thr Thr Thr Ala Thr Thr Thr
    690                 695                 700

Cys Cys Gly Ala Ala Thr Gly Cys Ala Ala Cys Ala Ala Gly Cys Thr
705                 710                 715                 720

Cys Cys Gly Cys Ala Thr Thr Ala Cys Ala Cys Cys Cys Gly Ala Ala
                725                 730                 735

Cys Ala Thr Cys Ala Cys Thr Cys Cys Ala Gly Ala Thr Gly Ala Gly
            740                 745                 750

Gly Gly Cys Thr Thr Thr Cys Thr Gly Ala Gly Thr Gly Thr Gly Gly
        755                 760                 765

Gly Gly Thr Cys Ala Ala Ala Thr Ala Gly Thr Thr Thr Cys Ala Thr
    770                 775                 780
```

-continued

```
Gly Thr Thr Cys Cys Cys Cys Ala Ala Ala Thr Gly Gly Cys Cys Cys
785                 790                 795                 800

Ala Ala Ala Ala Cys Thr Gly Ala Cys Ala Gly Thr Thr Thr Ala Ala
                805                 810                 815

Ala Cys Gly Cys Thr Gly Thr Cys Thr Thr Gly Gly Ala Ala Cys Cys
                820                 825                 830

Thr Ala Ala Thr Ala Thr Gly Ala Cys Ala Ala Ala Gly Cys Gly Gly
            835                 840                 845

Thr Gly Ala Thr Cys Thr Cys Ala Thr Cys Cys Ala Ala Gly Ala Thr
            850                 855                 860

Gly Ala Ala Cys Thr Ala Ala Gly Thr Thr Gly Gly Thr Thr Cys
865                 870                 875                 880

Gly Thr Thr Gly Ala Ala Ala Thr Gly Cys Thr Ala Ala Cys Gly Gly
                885                 890                 895

Cys Cys Ala Gly Thr Gly Gly Thr Cys Ala Ala Ala Ala Ala Gly
                900                 905                 910

Ala Ala Ala Cys Thr Thr Cys Cys Ala Ala Ala Gly Thr Cys Gly
                915                 920                 925

Gly Cys Ala Thr Ala Cys Cys Gly Thr Thr Gly Thr Cys Thr Thr
        930                 935                 940

Gly Thr Thr Thr Gly Gly Thr Ala Thr Thr Gly Ala Thr Thr Gly Ala
945                 950                 955                 960

Cys Gly Ala Ala Thr Gly Cys Thr Cys Ala Ala Ala Ala Thr Ala
                965                 970                 975

Ala Thr Cys Thr Cys Ala Thr Thr Ala Ala Thr Gly Cys Thr Thr Ala
            980                 985                 990

Gly Cys Gly Cys Ala Gly Thr Cys  Thr Cys Thr Cys Thr  Ala Thr Cys
                995                 1000                1005

Gly Cys  Thr Thr Cys Thr Gly  Ala Ala Cys Cys Cys  Cys Gly Gly
        1010                 1015                  1020

Thr Gly  Cys Ala Cys Cys Thr  Gly Thr Gly Cys Cys  Gly Ala Ala
        1025                 1030                  1035

Ala Cys  Gly Cys Ala Ala Ala  Thr Gly Gly Gly  Ala Ala Ala
        1040                 1045                  1050

Cys Ala  Cys Cys Cys Gly Cys  Thr Thr Thr Thr  Gly Gly Ala
        1055                 1060                  1065

Thr Gly  Ala Thr Thr Ala Thr  Gly Cys Ala Thr  Gly Thr Cys
        1070                 1075                  1080

Thr Cys  Cys Ala Cys Ala Thr  Thr Gly Thr Ala Thr  Gly Cys Thr
        1085                 1090                  1095

Thr Cys  Cys Ala Ala Gly Ala  Thr Thr Cys Thr Gly  Gly Thr Gly
        1100                 1105                  1110

Gly Gly  Ala Ala Thr Ala Cys  Thr Gly Cys Thr Gly  Ala Thr Ala
        1115                 1120                  1125

Gly Cys  Cys Thr Ala Ala Cys  Gly Thr Cys Thr Ala  Thr Gly Ala
        1130                 1135                  1140

Thr Cys  Ala Ala Ala Ala Thr  Thr Thr Ala Ala Cys  Thr Gly Thr
        1145                 1150                  1155

Thr Cys  Thr Ala Ala Cys Cys  Cys Cys Thr Ala Cys  Thr Thr Gly
        1160                 1165                  1170

Ala Cys  Ala Gly Cys Ala Ala  Thr Ala Thr Ala Thr  Ala Ala Ala
        1175                 1180                  1185

Cys Ala  Gly Ala Ala Gly Gly  Ala Ala Gly Cys Thr  Gly Cys Cys
```

```
    1190                1195                1200

Cys Thr  Gly Thr Cys Thr Thr  Ala Ala Ala Cys Cys  Thr Thr Thr
    1205                1210                1215

Thr Thr  Thr Thr Thr Thr Ala  Thr Cys Ala Thr Cys  Ala Thr Thr
    1220                1225                1230

Ala Thr  Thr Ala Gly Cys Thr  Thr Ala Cys Thr Thr  Thr Cys Ala
    1235                1240                1245

Thr Ala  Ala Thr Thr Gly Cys  Gly Ala Cys Thr Gly  Gly Thr Thr
    1250                1255                1260

Cys Cys  Ala Ala Thr Thr Gly  Ala Cys Ala Ala Gly  Cys Thr Thr
    1265                1270                1275

Thr Thr  Gly Ala Thr Thr Thr  Thr Ala Ala Cys Gly  Ala Cys Thr
    1280                1285                1290

Thr Thr  Thr Ala Ala Cys Gly  Ala Cys Ala Ala Cys  Thr Thr Gly
    1295                1300                1305

Ala Gly  Ala Ala Gly Ala Thr  Cys Ala Ala Ala Ala  Ala Ala Cys
    1310                1315                1320

Ala Ala  Cys Thr Ala Ala Thr  Thr Ala Thr Thr Cys  Gly Ala Ala
    1325                1330                1335

Ala Cys  Gly Gly Ala Ala Thr  Thr Cys Ala Cys Gly  Ala Thr Gly
    1340                1345                1350

Ala Gly  Ala Thr Thr Thr Cys  Cys Thr Thr Cys Ala  Ala Thr Thr
    1355                1360                1365

Thr Thr  Thr Ala Cys Thr Gly  Cys Thr Gly Thr Thr  Thr Thr Ala
    1370                1375                1380

Thr Thr  Cys Gly Cys Ala Gly  Cys Ala Thr Cys Cys  Thr Cys Cys
    1385                1390                1395

Gly Cys  Ala Thr Thr Ala Gly  Cys Thr Gly Ala Cys  Ala Ala Gly
    1400                1405                1410

Ala Cys  Ala Cys Ala Thr Ala  Cys Thr Thr Gly Thr  Cys Cys Ala
    1415                1420                1425

Cys Cys  Ala Thr Gly Thr Cys  Cys Ala Gly Cys Thr  Cys Cys Ala
    1430                1435                1440

Gly Ala  Ala Thr Thr Gly Thr  Thr Gly Gly Gly Thr  Gly Gly Thr
    1445                1450                1455

Cys Cys  Ala Thr Cys Cys Gly  Thr Thr Thr Thr Cys  Thr Thr Gly
    1460                1465                1470

Thr Thr  Cys Cys Cys Ala Cys  Cys Ala Ala Ala Gly  Cys Cys Ala
    1475                1480                1485

Ala Ala  Gly Gly Ala Cys Ala  Cys Thr Thr Thr Gly  Ala Thr Gly
    1490                1495                1500

Ala Thr  Cys Thr Cys Cys Ala  Gly Ala Ala Cys Thr  Cys Cys Ala
    1505                1510                1515

Gly Ala  Gly Gly Thr Thr Ala  Cys Ala Thr Gly Thr  Gly Thr Thr
    1520                1525                1530

Gly Thr  Thr Gly Thr Thr Gly  Ala Cys Gly Thr Thr  Thr Cys Thr
    1535                1540                1545

Cys Ala  Cys Gly Ala Gly Gly  Ala Cys Cys Cys Ala  Gly Ala Gly
    1550                1555                1560

Gly Thr  Thr Ala Ala Gly Thr  Thr Cys Ala Ala Cys  Thr Gly Gly
    1565                1570                1575

Thr Ala  Cys Gly Thr Thr Gly  Ala Cys Gly Gly Thr  Gly Thr Thr
    1580                1585                1590
```

-continued

Gly Ala Ala Gly Thr Thr Cys Ala Cys Ala Ala Cys Gly Cys Thr
1595                 1600                1605

Ala Ala Gly Ala Cys Thr Ala Ala Gly Cys Cys Ala Ala Gly Ala
1610                 1615                1620

Gly Ala Ala Gly Ala Gly Cys Ala Gly Thr Ala Cys Ala Ala Cys
1625                 1630                1635

Thr Cys Cys Ala Cys Thr Thr Ala Cys Ala Gly Ala Gly Thr Thr
1640                 1645                1650

Gly Thr Thr Thr Cys Gly Thr Thr Thr Gly Ala Cys Thr
1655                 1660                1665

Gly Thr Thr Thr Thr Gly Cys Ala Cys Cys Ala Gly Gly Ala Cys
1670                 1675                1680

Thr Gly Gly Thr Thr Gly Ala Ala Cys Gly Gly Thr Ala Ala Ala
1685                 1690                1695

Gly Ala Ala Thr Ala Cys Ala Ala Gly Thr Gly Thr Ala Ala Gly
1700                 1705                1710

Gly Thr Thr Thr Cys Ala Ala Cys Ala Ala Gly Gly Cys Gly Thr
1715                 1720                1725

Thr Thr Gly Cys Cys Ala Gly Cys Thr Cys Cys Ala Ala Thr Cys
1730                 1735                1740

Gly Ala Ala Ala Ala Gly Ala Cys Thr Ala Thr Cys Thr Cys Cys
1745                 1750                1755

Ala Ala Gly Gly Cys Thr Ala Ala Gly Gly Gly Thr Cys Ala Ala
1760                 1765                1770

Cys Cys Ala Ala Gly Ala Gly Ala Gly Cys Cys Ala Cys Ala Gly
1775                 1780                1785

Gly Thr Thr Thr Ala Cys Ala Cys Thr Thr Thr Gly Cys Cys Ala
1790                 1795                1800

Cys Cys Ala Thr Cys Thr Ala Gly Ala Gly Ala Ala Gly Ala Gly
1805                 1810                1815

Ala Thr Gly Ala Cys Thr Ala Ala Gly Ala Ala Cys Cys Ala Gly
1820                 1825                1830

Gly Thr Thr Thr Cys Cys Thr Thr Gly Ala Cys Thr Thr Gly Thr
1835                 1840                1845

Thr Thr Gly Gly Thr Thr Ala Ala Ala Gly Gly Ala Thr Thr Cys
1850                 1855                1860

Thr Ala Cys Cys Cys Ala Thr Cys Cys Gly Ala Cys Ala Thr Thr
1865                 1870                1875

Gly Cys Thr Gly Thr Thr Gly Ala Gly Thr Gly Gly Gly Ala Ala
1880                 1885                1890

Thr Cys Thr Ala Ala Cys Gly Gly Thr Cys Ala Ala Cys Cys Ala
1895                 1900                1905

Gly Ala Gly Ala Ala Cys Ala Ala Cys Thr Ala Cys Ala Ala Gly
1910                 1915                1920

Ala Cys Thr Ala Cys Thr Cys Cys Ala Cys Cys Ala Gly Thr Thr
1925                 1930                1935

Thr Thr Gly Gly Ala Thr Thr Cys Thr Gly Ala Thr Gly Gly Thr
1940                 1945                1950

Thr Cys Cys Thr Thr Cys Thr Thr Cys Thr Thr Gly Thr Ala Cys
1955                 1960                1965

Thr Cys Cys Ala Ala Gly Thr Thr Gly Ala Cys Thr Gly Thr Thr
1970                 1975                1980

-continued

```
Gly Ala  Cys Ala Ala Gly Thr  Cys Cys Ala Gly Ala  Thr Gly Gly
    1985                 1990                 1995

Cys Ala  Ala Cys Ala Gly Gly  Gly Thr Ala Ala Cys  Gly Thr Thr
    2000                 2005                 2010

Thr Thr  Cys Thr Cys Cys Thr  Gly Thr Thr Cys Cys  Gly Thr Thr
    2015                 2020                 2025

Ala Thr  Gly Cys Ala Thr Gly  Ala Gly Gly Cys Thr  Thr Thr Gly
    2030                 2035                 2040

Cys Ala  Cys Ala Ala Cys Cys  Ala Cys Thr Ala Cys  Ala Cys Thr
    2045                 2050                 2055

Cys Ala  Ala Ala Ala Gly Thr  Cys Cys Thr Thr Gly  Thr Cys Thr
    2060                 2065                 2070

Thr Thr  Gly Thr Cys Cys Cys  Cys Thr Gly Gly Thr  Gly Gly Thr
    2075                 2080                 2085

Gly Gly  Thr Gly Gly Thr Gly  Thr Cys Gly Ala Cys  Cys Ala Ala
    2090                 2095                 2100

Thr Thr  Cys Thr Cys Thr Ala  Ala Cys Thr Cys Thr  Ala Cys Thr
    2105                 2110                 2115

Thr Cys  Cys Gly Cys Thr Thr  Cys Cys Thr Cys Thr  Ala Cys Thr
    2120                 2125                 2130

Gly Ala  Cys Gly Thr Thr Ala  Cys Thr Thr Cys Cys  Thr Cys Cys
    2135                 2140                 2145

Thr Cys  Cys Thr Cys Thr Ala  Thr Thr Thr Cys Thr  Ala Cys Thr
    2150                 2155                 2160

Thr Cys  Cys Thr Cys Cys Gly  Gly Thr Thr Cys Cys  Gly Thr Thr
    2165                 2170                 2175

Ala Cys  Thr Ala Thr Thr Ala  Cys Thr Thr Cys Cys  Thr Cys Thr
    2180                 2185                 2190

Gly Ala  Gly Gly Cys Thr Cys  Cys Ala Gly Ala Ala  Thr Cys Thr
    2195                 2200                 2205

Gly Ala  Cys Ala Ala Cys Gly  Gly Thr Ala Cys Thr  Thr Cys Thr
    2210                 2215                 2220

Ala Cys  Thr Gly Cys Thr Gly  Cys Thr Cys Cys Ala  Ala Cys Thr
    2225                 2230                 2235

Gly Ala  Ala Ala Cys Thr Thr  Cys Thr Ala Cys Thr  Gly Ala Gly
    2240                 2245                 2250

Gly Cys  Thr Cys Cys Thr Ala  Cys Thr Ala Cys Thr  Gly Cys Thr
    2255                 2260                 2265

Ala Thr  Thr Cys Cys Ala Ala  Cys Thr Ala Ala Cys  Gly Gly Ala
    2270                 2275                 2280

Ala Cys  Thr Thr Cys Cys Ala  Cys Ala Gly Ala Gly  Gly Cys Thr
    2285                 2290                 2295

Cys Cys  Ala Ala Cys Ala Ala  Cys Ala Gly Cys Thr  Ala Thr Cys
    2300                 2305                 2310

Cys Cys  Thr Ala Cys Ala Ala  Ala Cys Gly Gly Thr  Ala Cys Ala
    2315                 2320                 2325

Thr Cys  Cys Ala Cys Thr Gly  Ala Ala Gly Cys Thr  Cys Cys Thr
    2330                 2335                 2340

Ala Cys  Thr Gly Ala Cys Ala  Cys Thr Ala Cys Thr  Ala Cys Ala
    2345                 2350                 2355

Gly Ala  Ala Gly Cys Thr Cys  Cys Ala Ala Cys Thr  Ala Cys Thr
    2360                 2365                 2370

Gly Cys  Thr Thr Thr Gly Cys  Cys Thr Ala Cys Thr  Ala Ala Thr
```

-continued

```
    2375                2380                2385

Gly Gly  Thr Ala Cys Ala Thr  Cys Ala Ala Cys Ala  Gly Ala Gly
    2390                2395                2400

Gly Cys  Thr Cys Cys Thr Ala  Cys Ala Gly Ala Thr  Ala Cys Ala
    2405                2410                2415

Ala Cys  Ala Ala Cys Thr Gly  Ala Ala Gly Cys Thr  Cys Cys Ala
    2420                2425                2430

Ala Cys  Ala Ala Cys Thr Gly  Gly Ala Thr Thr Gly  Cys Cys Ala
    2435                2440                2445

Ala Cys  Ala Ala Ala Cys Gly  Gly Thr Ala Cys Thr  Ala Cys Thr
    2450                2455                2460

Thr Cys  Thr Gly Cys Thr Thr  Thr Cys Cys Cys Ala  Cys Cys Ala
    2465                2470                2475

Ala Cys  Thr Ala Cys Thr Thr  Cys Cys Thr Thr Gly  Cys Cys Ala
    2480                2485                2490

Cys Cys  Ala Thr Cys Cys Ala  Ala Cys Ala Cys Thr  Ala Cys Thr
    2495                2500                2505

Ala Cys  Thr Ala Cys Thr Cys  Cys Ala Cys Cys Ala  Thr Ala Cys
    2510                2515                2520

Ala Ala  Cys Cys Cys Ala Thr  Cys Cys Ala Cys Thr  Gly Ala Cys
    2525                2530                2535

Thr Ala  Cys Ala Cys Thr Ala  Cys Thr Gly Ala Cys  Thr Ala Cys
    2540                2545                2550

Ala Cys  Ala Gly Thr Thr Gly  Thr Thr Ala Cys Thr  Gly Ala Gly
    2555                2560                2565

Thr Ala  Cys Ala Cys Thr Ala  Cys Thr Thr Ala Cys  Thr Gly Thr
    2570                2575                2580

Cys Cys  Ala Gly Ala Gly Cys  Cys Ala Ala Cys Thr  Ala Cys Thr
    2585                2590                2595

Thr Thr  Cys Ala Cys Ala Ala  Cys Ala Ala Ala Cys  Gly Gly Ala
    2600                2605                2610

Ala Ala  Gly Ala Cys Thr Thr  Ala Cys Ala Cys Thr  Gly Thr Thr
    2615                2620                2625

Ala Cys  Thr Gly Ala Gly Cys  Cys Thr Ala Cys Thr  Ala Cys Thr
    2630                2635                2640

Thr Thr  Gly Ala Cys Thr Ala  Thr Cys Ala Cys Thr  Gly Ala Cys
    2645                2650                2655

Thr Gly  Thr Cys Cys Ala Thr  Gly Thr Ala Cys Thr  Ala Thr Cys
    2660                2665                2670

Gly Ala  Gly Ala Ala Gly Cys  Cys Ala Ala Cys Thr  Ala Cys Thr
    2675                2680                2685

Ala Cys  Thr Thr Cys Cys Ala  Cys Thr Ala Cys Ala  Gly Ala Gly
    2690                2695                2700

Thr Ala  Thr Ala Cys Thr Gly  Thr Thr Gly Thr Thr  Ala Cys Ala
    2705                2710                2715

Gly Ala  Ala Thr Ala Cys Ala  Cys Ala Ala Cys Ala  Thr Ala Thr
    2720                2725                2730

Thr Gly  Thr Cys Cys Thr Gly  Ala Gly Cys Cys Ala  Ala Cys Ala
    2735                2740                2745

Ala Cys  Ala Thr Thr Cys Ala  Cys Thr Ala Cys Thr  Ala Ala Thr
    2750                2755                2760

Gly Gly  Ala Ala Ala Ala Ala  Cys Ala Thr Ala Cys  Ala Cys Ala
    2765                2770                2775
```

-continued

```
Gly Thr Thr Ala Cys Ala Gly Ala Ala Cys Cys Ala Ala Cys Thr
            2780            2785            2790
Ala Cys Ala Thr Thr Gly Ala Cys Ala Ala Thr Ala Cys Ala
    2795            2800            2805
Gly Ala Thr Thr Gly Thr Cys Cys Thr Thr Gly Thr Ala Cys Ala
            2810            2815            2820
Ala Thr Thr Gly Ala Gly Ala Ala Gly Thr Cys Cys Gly Ala Gly
    2825            2830            2835
Gly Cys Thr Cys Cys Thr Gly Ala Ala Thr Cys Thr Thr Cys Thr
            2840            2845            2850
Gly Thr Thr Cys Cys Ala Gly Thr Thr Ala Cys Thr Gly Ala Ala
    2855            2860            2865
Thr Cys Cys Ala Ala Gly Gly Thr Ala Cys Thr Ala Cys Thr
            2870            2875            2880
Ala Cys Thr Ala Ala Ala Gly Ala Ala Ala Cys Thr Gly Gly Thr
    2885            2890            2895
Gly Thr Thr Ala Cys Thr Ala Cys Thr Ala Ala Gly Cys Ala Gly
            2900            2905            2910
Ala Cys Thr Ala Cys Thr Gly Cys Thr Ala Ala Cys Cys Cys Ala
    2915            2920            2925
Thr Cys Cys Thr Thr Gly Ala Cys Thr Gly Thr Thr Cys Cys
            2930            2935            2940
Ala Cys Thr Gly Thr Thr Gly Thr Thr Cys Cys Ala Gly Thr Thr
    2945            2950            2955
Thr Cys Thr Thr Cys Cys Thr Cys Thr Gly Cys Thr Thr Cys Thr
            2960            2965            2970
Thr Cys Cys Cys Ala Cys Thr Cys Cys Gly Thr Thr Gly Thr Thr
    2975            2980            2985
Ala Thr Cys Ala Ala Cys Thr Cys Cys Ala Ala Cys Gly Gly Thr
            2990            2995            3000
Gly Cys Thr Ala Ala Cys Gly Thr Thr Gly Thr Thr Gly Thr Thr
    3005            3010            3015
Cys Cys Thr Gly Gly Thr Gly Cys Thr Thr Thr Gly Gly Gly Ala
            3020            3025            3030
Thr Thr Gly Gly Cys Thr Gly Gly Thr Gly Thr Thr Gly Cys Thr
    3035            3040            3045
Ala Thr Gly Thr Thr Gly Thr Cys Thr Thr Gly Thr Ala Ala
            3050            3055            3060
Thr Ala Gly Gly Gly Cys Cys Gly Gly Cys Cys Ala Thr Thr Thr
    3065            3070            3075
Ala Ala Ala Thr Ala Cys Ala Gly Gly Cys Cys Cys Thr Thr
            3080            3085            3090
Thr Thr Cys Cys Thr Thr Thr Gly Thr Cys Gly Ala Thr Ala Thr
    3095            3100            3105
Cys Ala Thr Gly Thr Ala Ala Thr Thr Ala Gly Thr Thr Ala Thr
            3110            3115            3120
Gly Thr Cys Ala Cys Gly Cys Thr Thr Ala Cys Ala Thr Thr Cys
    3125            3130            3135
Ala Cys Gly Cys Cys Cys Thr Cys Cys Thr Cys Cys Cys Ala Cys
            3140            3145            3150
Ala Thr Cys Cys Gly Cys Thr Cys Thr Ala Ala Cys Cys Gly Ala
    3155            3160            3165
```

```
Ala Ala  Ala Gly Gly Ala Ala  Gly Gly Ala Gly  Thr Ala Gly
    3170             3175             3180

Ala Cys  Ala Ala Cys Cys Thr  Gly Ala Ala Gly  Cys Thr Ala
    3185             3190             3195

Gly Gly  Thr Cys Cys Thr Ala  Thr Thr Thr Ala  Thr Thr Thr
    3200             3205             3210

Thr Thr  Thr Thr Thr Ala Ala  Thr Ala Gly Thr  Ala Thr Gly
    3215             3220             3225

Thr Thr  Ala Gly Thr Ala Thr  Thr Ala Ala Gly Ala  Ala Cys Gly
    3230             3235             3240

Thr Thr  Ala Thr Thr Thr Ala  Thr Ala Thr Thr  Cys Ala Ala
    3245             3250             3255

Ala Thr  Thr Thr Thr Thr Cys  Thr Thr Thr Thr  Thr Thr Thr
    3260             3265             3270

Cys Thr  Gly Thr Ala Cys Ala  Ala Ala Cys Gly Cys  Gly Thr Gly
    3275             3280             3285

Thr Ala  Cys Gly Cys Ala Thr  Gly Thr Ala Ala  Cys Ala Thr Thr
    3290             3295             3300

Ala Thr  Ala Cys Thr Gly Ala  Ala Ala Ala Cys Cys  Thr Thr Gly
    3305             3310             3315

Cys Thr  Thr Gly Ala Gly Ala  Ala Gly Gly Thr Thr  Thr Thr Gly
    3320             3325             3330

Gly Gly  Ala Cys Gly Cys Thr  Cys Gly Ala Ala Gly  Gly Cys Thr
    3335             3340             3345

Thr Thr  Ala Ala Thr Thr Thr  Gly Cys Ala Ala Gly  Cys Thr Gly
    3350             3355             3360

Gly Ala  Thr Cys Cys Gly Cys  Gly Gly Cys Cys Gly  Cys Thr Thr
    3365             3370             3375

Ala Cys  Gly Cys Gly Cys Cys  Gly Thr Thr Cys Thr  Thr Cys Gly
    3380             3385             3390

Cys Thr  Thr Gly Gly Thr Cys  Thr Thr Gly Thr Ala  Thr Cys Thr
    3395             3400             3405

Cys Cys  Thr Thr Ala Cys Ala  Cys Thr Gly Thr Ala  Thr Cys Thr
    3410             3415             3420

Thr Cys  Cys Cys Ala Thr Thr  Thr Gly Cys Gly Thr  Thr Thr Ala
    3425             3430             3435

Gly Gly  Thr Gly Gly Thr Thr  Ala Thr Cys Ala Ala  Ala Ala Ala
    3440             3445             3450

Cys Thr  Ala Ala Ala Ala Gly  Gly Ala Ala Ala Ala  Ala Thr Thr
    3455             3460             3465

Thr Cys  Ala Gly Ala Thr Gly  Thr Thr Ala Thr  Cys Thr Cys
    3470             3475             3480

Thr Ala  Ala Gly Gly Thr Thr  Thr Thr Thr Thr Cys  Thr Thr Thr
    3485             3490             3495

Thr Thr  Ala Cys Ala Gly Thr  Ala Thr Ala Cys  Ala Cys Gly
    3500             3505             3510

Thr Gly  Ala Thr Gly Cys Gly  Thr Cys Ala Cys Gly  Thr Gly Gly
    3515             3520             3525

Thr Ala  Cys Thr Ala Gly Ala  Thr Thr Ala Cys Gly  Thr Ala Ala
    3530             3535             3540

Gly Thr  Thr Ala Thr Thr Thr  Thr Gly Gly Thr Cys  Cys Gly Gly
    3545             3550             3555

Thr Gly  Gly Gly Thr Ala Ala  Gly Thr Gly Gly Gly  Thr Ala Ala
```

-continued

```
             3560                3565                3570

Gly Ala  Ala Thr Ala Gly Ala  Ala Ala Gly Cys Ala  Thr Gly Ala
     3575                3580                3585

Ala Gly  Gly Thr Thr Thr Ala  Cys Ala Ala Ala Ala  Ala Cys Gly
     3590                3595                3600

Cys Ala  Gly Thr Cys Ala Cys  Gly Ala Ala Thr Thr  Ala Thr Thr
     3605                3610                3615

Gly Cys  Thr Ala Cys Thr Thr  Cys Gly Ala Gly Cys  Thr Thr Gly
     3620                3625                3630

Gly Ala  Ala Cys Cys Ala Cys  Cys Cys Ala Ala  Ala Gly Ala
     3635                3640                3645

Thr Thr  Ala Thr Ala Thr Thr  Gly Thr Ala Cys Thr  Gly Ala Thr
     3650                3655                3660

Gly Cys  Ala Cys Thr Ala Cys  Cys Thr Thr Cys Thr  Cys Gly Ala
     3665                3670                3675

Thr Thr  Thr Thr Gly Cys Thr  Cys Cys Thr Cys Cys  Ala Ala Gly
     3680                3685                3690

Ala Ala  Cys Cys Thr Ala Cys  Gly Ala Ala Ala  Ala Cys Ala
     3695                3700                3705

Thr Thr  Thr Cys Thr Thr Gly  Ala Gly Cys Cys Thr  Thr Thr Thr
     3710                3715                3720

Cys Ala  Ala Cys Cys Thr Ala  Gly Ala Cys Thr Ala  Cys Ala Cys
     3725                3730                3735

Ala Thr  Cys Ala Ala Gly Thr  Thr Ala Thr Thr Thr  Ala Ala Gly
     3740                3745                3750

Gly Thr  Ala Thr Gly Thr Thr  Cys Cys Gly Thr Thr  Ala Ala Cys
     3755                3760                3765

Ala Thr  Gly Thr Ala Ala Gly  Ala Ala Ala Gly  Gly Ala Gly
     3770                3775                3780

Ala Gly  Gly Ala Thr Ala Gly  Ala Thr Cys Gly Thr  Thr Thr Ala
     3785                3790                3795

Thr Gly  Gly Gly Gly Thr Ala  Cys Gly Thr Cys Gly  Cys Cys Thr
     3800                3805                3810

Gly Ala  Thr Thr Cys Ala Ala  Gly Cys Gly Thr Gly  Ala Cys Cys
     3815                3820                3825

Ala Thr  Thr Cys Gly Ala Ala  Gly Ala Ala Thr Ala  Gly Gly Cys
     3830                3835                3840

Cys Thr  Thr Cys Gly Ala Ala  Ala Gly Cys Thr Gly  Ala Ala Thr
     3845                3850                3855

Ala Ala  Ala Gly Cys Ala Ala  Ala Thr Gly Thr Cys  Ala Gly Thr
     3860                3865                3870

Thr Gly  Cys Gly Ala Thr Thr  Gly Gly Thr Ala Thr  Gly Cys Thr
     3875                3880                3885

Gly Ala  Cys Ala Ala Ala Thr  Thr Ala Gly Cys Ala  Thr Ala Ala
     3890                3895                3900

Ala Ala  Ala Gly Cys Ala Ala  Thr Ala Gly Ala Cys  Thr Thr Thr
     3905                3910                3915

Cys Thr  Ala Ala Cys Cys Ala  Cys Cys Thr Gly Thr  Thr Thr Thr
     3920                3925                3930

Thr Thr  Thr Cys Cys Thr Thr  Thr Thr Ala Cys Thr  Thr Thr Ala
     3935                3940                3945

Thr Thr  Thr Ala Thr Ala Thr  Thr Thr Thr Gly Cys  Cys Ala Cys
     3950                3955                3960
```

```
Cys Gly  Thr Ala Cys Thr Ala  Ala Cys Ala Ala Gly  Thr Thr Cys
    3965                 3970                 3975

Ala Gly  Ala Cys Ala Ala Ala  Thr Thr Ala Ala Thr  Thr Ala Ala
    3980                 3985                 3990

Cys Ala  Cys Cys Ala Thr Gly  Thr Cys Ala Gly Ala  Ala Gly Ala
    3995                 4000                 4005

Thr Cys  Ala Ala Ala Ala Ala  Ala Gly Thr Gly Ala  Ala Ala Ala
    4010                 4015                 4020

Thr Thr  Cys Cys Gly Thr Ala  Cys Cys Thr Thr Cys  Thr Ala Ala
    4025                 4030                 4035

Gly Gly  Thr Thr Ala Ala Thr  Ala Thr Gly Gly Thr  Gly Ala Ala
    4040                 4045                 4050

Thr Cys  Gly Cys Ala Cys Cys  Gly Ala Thr Ala Thr  Ala Cys Thr
    4055                 4060                 4065

Gly Ala  Cys Thr Ala Cys Gly  Ala Thr Cys Ala Ala  Gly Thr Cys
    4070                 4075                 4080

Ala Thr  Thr Gly Thr Cys Ala  Thr Gly Gly Cys Thr  Thr Gly Ala
    4085                 4090                 4095

Cys Thr  Thr Gly Ala Thr Gly  Thr Thr Gly Cys Cys  Ala Thr Thr
    4100                 4105                 4110

Thr Ala  Cys Thr Ala Thr Ala  Ala Thr Thr Cys Thr  Cys Thr Cys
    4115                 4120                 4125

Cys Ala  Thr Ala Ala Thr Cys  Ala Thr Thr Gly Cys  Ala Gly Thr
    4130                 4135                 4140

Ala Ala  Thr Ala Ala Thr Thr  Thr Cys Thr Gly Thr  Cys Thr Ala
    4145                 4150                 4155

Thr Gly  Thr Gly Cys Cys Thr  Thr Cys Thr Thr Cys  Cys Cys Gly
    4160                 4165                 4170

Thr Cys  Ala Cys Ala Cys Thr  Thr Thr Thr Gly Ala  Cys Gly Cys
    4175                 4180                 4185

Thr Gly  Ala Ala Gly Gly Thr  Cys Ala Thr Cys Cys  Cys Ala Ala
    4190                 4195                 4200

Thr Cys  Thr Ala Ala Thr Gly  Gly Gly Ala Gly Thr  Gly Thr Cys
    4205                 4210                 4215

Cys Ala  Thr Thr Cys Cys Thr  Thr Thr Gly Ala Cys  Thr Gly Thr
    4220                 4225                 4230

Thr Gly  Gly Thr Ala Thr Gly  Ala Thr Thr Gly Thr  Ala Ala Thr
    4235                 4240                 4245

Gly Ala  Thr Gly Ala Thr Thr  Cys Cys Cys Cys Cys  Gly Ala Thr
    4250                 4255                 4260

Cys Thr  Gly Cys Ala Ala Ala  Gly Thr Thr Thr Cys  Cys Thr Gly
    4265                 4270                 4275

Gly Gly  Ala Gly Thr Cys Thr  Ala Thr Thr Cys Ala  Cys Ala Ala
    4280                 4285                 4290

Gly Thr  Ala Cys Thr Thr Cys  Thr Ala Cys Ala Gly  Gly Ala Gly
    4295                 4300                 4305

Cys Thr  Ala Thr Ala Thr Ala  Ala Gly Gly Ala Ala  Gly Cys Ala
    4310                 4315                 4320

Ala Cys  Thr Ala Gly Cys Cys  Cys Thr Cys Thr Cys  Gly Thr Thr
    4325                 4330                 4335

Ala Thr  Thr Thr Thr Thr Gly  Ala Ala Thr Thr Gly  Gly Gly Thr
    4340                 4345                 4350
```

-continued

```
Cys Ala Thr Cys Gly Gly Thr Cys Cys Thr Thr Thr Gly Thr Thr
    4355            4360                4365
Gly Ala Thr Gly Ala Cys Ala Gly Cys Ala Thr Gly Gly Cys
    4370            4375                4380
Gly Thr Gly Gly Ala Thr Gly Gly Cys Gly Cys Thr Ala Thr Thr
    4385            4390                4395
Cys Gly Ala Thr Thr Ala Thr Ala Ala Gly Gly Ala Ala Thr Ala
    4400            4405                4410
Cys Cys Gly Thr Cys Ala Ala Gly Gly Cys Ala Thr Thr Ala Thr
    4415            4420                4425
Thr Ala Thr Gly Ala Thr Cys Gly Gly Ala Gly Thr Ala Gly Cys
    4430            4435                4440
Thr Ala Gly Ala Thr Gly Cys Ala Thr Thr Gly Cys Cys Ala Thr
    4445            4450                4455
Gly Gly Thr Gly Cys Thr Ala Ala Thr Thr Gly Gly Ala Ala
    4460            4465                4470
Thr Cys Ala Gly Ala Thr Thr Gly Cys Thr Gly Gly Ala Gly Gly
    4475            4480                4485
Ala Gly Ala Cys Ala Ala Thr Gly Ala Thr Cys Thr Cys Thr Gly
    4490            4495                4500
Cys Gly Thr Cys Gly Thr Gly Cys Thr Thr Gly Thr Thr Ala Thr
    4505            4510                4515
Thr Ala Cys Ala Ala Ala Cys Thr Cys Gly Cys Thr Thr Thr Thr
    4520            4525                4530
Ala Cys Ala Gly Ala Thr Gly Gly Thr Ala Thr Thr Ala Thr Ala
    4535            4540                4545
Thr Gly Cys Ala Cys Cys Ala Thr Thr Gly Cys Ala Gly Ala Thr
    4550            4555                4560
Ala Thr Thr Thr Thr Ala Cys Thr Gly Thr Thr Ala Thr Gly Thr
    4565            4570                4575
Thr Ala Thr Thr Thr Cys Thr Cys Ala Thr Gly Ala Cys Cys Ala
    4580            4585                4590
Cys Cys Thr Gly Ala Ala Thr Ala Cys Thr Thr Cys Ala Ala Ala
    4595            4600                4605
Thr Ala Gly Gly Gly Thr Ala Thr Thr Ala Thr Cys Gly Ala
    4610            4615                4620
Ala Gly Ala Gly Gly Thr Thr Gly Cys Ala Ala Ala Gly Thr Cys
    4625            4630                4635
Thr Gly Thr Cys Gly Gly Ala Gly Thr Thr Thr Thr Cys Thr
    4640            4645                4650
Cys Gly Gly Cys Ala Thr Ala Cys Cys Ala Cys Thr Gly Gly Gly
    4655            4660                4665
Ala Ala Thr Thr Gly Gly Cys Ala Thr Ala Thr Cys Ala Thr
    4670            4675                4680
Ala Cys Gly Thr Thr Thr Gly Gly Gly Ala Ala Gly Thr Cys Thr
    4685            4690                4695
Thr Ala Cys Cys Ala Thr Ala Gly Cys Thr Gly Gly Thr Ala Ala
    4700            4705                4710
Ala Ala Gly Thr Ala Thr Thr Ala Thr Gly Ala Ala Ala Ala
    4715            4720                4725
Ala Thr Ala Cys Ala Thr Thr Thr Gly Ala Gly Ala Thr Thr
    4730            4735                4740
Thr Ala Thr Thr Thr Cys Thr Cys Cys Ala Thr Gly Gly Gly Cys
```

-continued

```
                4745                4750                4755
Ala Ala Thr Gly Ala Thr Cys Gly Gly Ala Thr Thr Thr Cys Ala
        4760                4765                4770
Thr Thr Ala Cys Ala Cys Thr Thr Thr Ala Thr Thr Thr Gly Thr
        4775                4780                4785
Thr Ala Thr Thr Thr Thr Thr Ala Thr Ala Gly Thr Ala Gly
        4790                4795                4800
Ala Gly Gly Thr Thr Ala Thr Cys Ala Ala Thr Thr Ala Thr
        4805                4810                4815
Cys Cys Ala Cys Gly Ala Ala Thr Thr Gly Gly Thr Thr Cys
        4820                4825                4830
Thr Gly Cys Ala Ala Thr Ala Thr Thr Gly Thr Gly Cys Thr Thr
        4835                4840                4845
Thr Gly Thr Cys Cys Cys Ala Thr Thr Gly Gly Thr Gly Cys Thr
        4850                4855                4860
Thr Thr Ala Cys Thr Thr Cys Thr Thr Thr Ala Thr Thr Gly Cys
        4865                4870                4875
Ala Thr Gly Gly Thr Thr Thr Thr Thr Gly Ala Cys Cys Thr Thr
        4880                4885                4890
Cys Gly Cys Ala Thr Thr Ala Ala Thr Gly Ala Gly Gly Thr Ala
        4895                4900                4905
Cys Thr Thr Ala Thr Cys Ala Ala Thr Ala Thr Cys Thr Ala Gly
        4910                4915                4920
Gly Ala Gly Thr Gly Ala Thr Ala Cys Ala Cys Ala Ala Ala Gly
        4925                4930                4935
Ala Gly Ala Ala Thr Gly Thr Ala Gly Cys Thr Gly Thr Gly Ala
        4940                4945                4950
Cys Cys Ala Ala Gly Ala Ala Cys Thr Ala Cys Thr Thr Thr Thr
        4955                4960                4965
Ala Ala Ala Gly Ala Gly Gly Gly Thr Cys Thr Gly Gly Gly Gly
        4970                4975                4980
Ala Ala Gly Ala Ala Ala Gly Thr Cys Thr Thr Gly Thr Gly Ala
        4985                4990                4995
Ala Gly Cys Thr Ala Gly Cys Thr Thr Thr Thr Cys Thr Ala Thr
        5000                5005                5010
Thr Ala Cys Gly Ala Thr Gly Ala Cys Gly Cys Ala Ala Thr Gly
        5015                5020                5025
Thr Thr Thr Cys Ala Cys Thr Ala Thr Gly Gly Cys Thr Thr Cys
        5030                5035                5040
Ala Ala Ala Thr Ala Ala Thr Thr Thr Gly Ala Ala Cys Thr
        5045                5050                5055
Ala Thr Cys Cys Cys Thr Gly Gly Cys Ala Ala Thr Thr Gly Cys
        5060                5065                5070
Thr Ala Thr Thr Thr Cys Cys Thr Thr Ala Thr Ala Thr Gly Gly
        5075                5080                5085
Thr Ala Ala Cys Ala Ala Thr Ala Gly Cys Ala Ala Gly Cys Ala
        5090                5095                5100
Ala Gly Cys Ala Ala Thr Ala Gly Cys Thr Gly Cys Ala Ala Cys
        5105                5110                5115
Ala Thr Thr Gly Gly Gly Cys Cys Gly Thr Thr Gly Cys Thr
        5120                5125                5130
Ala Gly Ala Ala Gly Thr Thr Cys Cys Ala Ala Thr Thr Thr Thr
        5135                5140                5145
```

```
Ala Thr Thr Gly Ala Thr Thr Thr Thr Gly Gly Cys Ala Ala Thr
        5150            5155            5160

Ala Gly Thr Cys Gly Cys Gly Ala Gly Ala Ala Thr Cys Cys Thr
        5165            5170            5175

Thr Ala Ala Ala Cys Cys Ala Thr Ala Thr Thr Ala Thr Ala Thr
        5180            5185            5190

Ala Thr Gly Gly Ala Ala Cys Ala Ala Thr Ala Gly Ala Ala Ala
        5195            5200            5205

Thr Thr Ala Ala Thr Thr Ala Ala Cys Ala Gly Gly Cys Cys Cys
        5210            5215            5220

Cys Thr Thr Thr Thr Cys Cys Thr Thr Thr Gly Thr Cys Gly Ala
        5225            5230            5235

Thr Ala Thr Cys Ala Thr Gly Thr Ala Ala Thr Thr Ala Gly Thr
        5240            5245            5250

Thr Ala Thr Gly Thr Cys Ala Cys Gly Cys Thr Thr Ala Cys Ala
        5255            5260            5265

Thr Thr Cys Ala Cys Gly Cys Cys Cys Thr Cys Cys Thr Cys Cys
        5270            5275            5280

Cys Ala Cys Ala Thr Cys Cys Gly Cys Thr Cys Thr Ala Ala Cys
        5285            5290            5295

Cys Gly Ala Ala Ala Ala Gly Gly Ala Ala Gly Gly Ala Gly Thr
        5300            5305            5310

Thr Ala Gly Ala Cys Ala Ala Cys Cys Thr Gly Ala Ala Gly Thr
        5315            5320            5325

Cys Thr Ala Gly Gly Thr Cys Cys Cys Thr Ala Thr Thr Thr Ala
        5330            5335            5340

Thr Thr Thr Thr Thr Thr Thr Thr Ala Ala Thr Ala Gly Thr Thr
        5345            5350            5355

Ala Thr Gly Thr Thr Ala Gly Thr Ala Thr Thr Ala Ala Gly Ala
        5360            5365            5370

Ala Cys Gly Thr Thr Ala Thr Thr Ala Thr Ala Thr Thr Thr Thr
        5375            5380            5385

Cys Ala Ala Ala Thr Thr Thr Thr Thr Cys Thr Thr Thr Thr Thr
        5390            5395            5400

Thr Thr Thr Cys Thr Gly Thr Ala Cys Ala Ala Ala Cys Gly Cys
        5405            5410            5415

Gly Thr Gly Thr Ala Cys Gly Cys Ala Thr Gly Thr Ala Ala Cys
        5420            5425            5430

Ala Thr Thr Ala Thr Ala Cys Thr Gly Thr Ala Ala Ala Ala Cys
        5435            5440            5445

Thr Thr Gly Cys Ala Ala Thr Gly Ala Ala Ala Thr Ala Ala Ala
        5450            5455            5460

Thr Thr Gly Gly Thr Thr Thr Gly Thr Thr Cys Gly Gly Thr Thr
        5465            5470            5475

Thr Ala Cys Thr Gly Thr Cys Gly Gly Cys Cys Ala Ala Gly Cys
        5480            5485            5490

Thr Gly Ala Cys Thr Ala Cys Thr Thr Gly Ala Ala Ala Gly Cys
        5495            5500            5505

Cys Ala Ala Cys Thr Thr Thr Thr Ala Thr Ala Thr Ala Thr Ala
        5510            5515            5520

Thr Thr Thr Ala Cys Cys Ala Ala Ala Ala Thr Ala Ala Thr Ala
        5525            5530            5535
```

-continued

```
Gly Ala  Cys Ala Thr Thr Ala  Gly Ala Ala Ala Thr  Gly Thr Gly
    5540                 5545                 5550

Thr Thr  Thr Gly Gly Thr Ala  Ala Gly Ala Ala Cys  Ala Thr Gly
    5555                 5560                 5565

Ala Ala  Gly Cys Cys Gly Gly  Ala Gly Gly Cys Ala  Thr Ala Cys
    5570                 5575                 5580

Ala Ala  Ala Cys Gly Ala Thr  Thr Cys Ala Cys Ala  Gly Ala Thr
    5585                 5590                 5595

Thr Thr  Gly Ala Ala Gly Gly  Ala Gly Gly Ala Ala  Ala Ala Cys
    5600                 5605                 5610

Ala Ala  Ala Cys Thr Gly Cys  Ala Thr Cys Cys Ala  Cys Cys Gly
    5615                 5620                 5625

Gly Ala  Ala Gly Thr Gly Cys  Cys Ala Gly Cys Ala  Gly Cys Cys
    5630                 5635                 5640

Gly Thr  Gly Thr Ala Thr Gly  Cys Cys Ala Ala Cys  Cys Thr Thr
    5645                 5650                 5655

Gly Cys  Thr Cys Thr Cys Ala  Ala Ala Gly Gly Cys  Ala Thr Thr
    5660                 5665                 5670

Cys Cys  Thr Ala Cys Gly Gly  Ala Thr Cys Thr Gly  Ala Gly Thr
    5675                 5680                 5685

Gly Gly  Gly Ala Ala Ala Thr  Ala Thr Cys Thr Gly  Ala Gly Ala
    5690                 5695                 5700

Thr Thr  Cys Ala Cys Ala Gly  Ala Cys Cys Cys Ala  Cys Thr Ala
    5705                 5710                 5715

Thr Thr  Gly Gly Ala Ala Cys  Ala Gly Thr Ala Cys  Cys Ala Ala
    5720                 5725                 5730

Ala Cys  Cys Thr Ala Gly Thr  Thr Thr Gly Gly Cys  Cys Gly Ala
    5735                 5740                 5745

Thr Cys  Cys Ala Thr Gly Ala  Thr Thr Ala Thr Gly  Thr Ala Ala
    5750                 5755                 5760

Thr Gly  Cys Ala Thr Ala Thr  Ala Gly Thr Thr Thr  Thr Thr Gly
    5765                 5770                 5775

Thr Cys  Gly Ala Thr Gly Cys  Thr Cys Ala Cys Cys  Cys Gly Thr
    5780                 5785                 5790

Thr Thr  Cys Gly Ala Gly Thr  Cys Thr Gly Thr Cys  Thr Cys Gly
    5795                 5800                 5805

Thr Ala  Thr Cys Gly Thr Cys  Thr Thr Ala Cys Gly  Thr Ala Thr
    5810                 5815                 5820

Ala Ala  Gly Thr Thr Cys Ala  Ala Gly Cys Ala Thr  Gly Thr Thr
    5825                 5830                 5835

Thr Ala  Cys Cys Ala Gly Gly  Thr Cys Thr Gly Thr  Thr Ala Gly
    5840                 5845                 5850

Ala Ala  Ala Cys Thr Cys Cys  Thr Thr Thr Gly Thr  Gly Ala Gly
    5855                 5860                 5865

Gly Gly  Cys Ala Gly Gly Ala  Cys Cys Thr Ala Thr  Thr Cys Gly
    5870                 5875                 5880

Thr Cys  Thr Cys Gly Gly Thr  Cys Cys Cys Gly Thr  Thr Gly Thr
    5885                 5890                 5895

Thr Thr  Cys Thr Ala Ala Gly  Ala Gly Ala Cys Thr  Gly Thr Ala
    5900                 5905                 5910

Cys Ala  Gly Cys Cys Ala Ala  Gly Cys Gly Cys Ala  Gly Ala Ala
    5915                 5920                 5925

Thr Gly  Gly Thr Gly Gly Cys  Ala Thr Thr Ala Ala  Cys Cys Ala
```

5930                5935                5940

Thr Ala Ala Gly Ala Gly Gly Ala Thr Thr Cys Thr Gly Ala Thr
            5945                5950                5955

Cys Gly Gly Ala Cys Thr Thr Gly Gly Thr Cys Thr Ala Thr Thr
            5960                5965                5970

Gly Gly Cys Thr Ala Thr Thr Gly Gly Ala Ala Cys Cys Ala Cys
            5975                5980                5985

Cys Cys Thr Thr Thr Ala Cys Gly Gly Ala Cys Ala Ala Cys
            5990                5995                6000

Cys Ala Ala Cys Cys Cys Thr Ala Cys Cys Ala Gly Ala Cys
            6005                6010                6015

Thr Cys Cys Thr Ala Thr Thr Gly Cys Ala Thr Thr Thr Gly Thr
            6020                6025                6030

Gly Gly Ala Ala Cys Cys Ala Gly Cys Cys Ala Cys Gly Gly Ala
            6035                6040                6045

Ala Ala Gly Ala Gly Cys Gly Thr Thr Ala Ala Gly Gly Ala
            6050                6055                6060

Cys Gly Gly Ala Gly Ala Cys Gly Thr Cys Thr Cys Thr Gly Thr
            6065                6070                6075

Gly Ala Thr Thr Thr Thr Thr Gly Thr Thr Cys Thr Cys Gly Gly
            6080                6085                6090

Ala Gly Gly Thr Cys Cys Ala Gly Gly Ala Gly Cys Thr Gly Gly
            6095                6100                6105

Ala Ala Ala Ala Gly Gly Thr Ala Cys Cys Cys Ala Ala Thr Gly
            6110                6115                6120

Thr Gly Cys Cys Ala Ala Ala Cys Thr Ala Gly Thr Gly Ala Gly
            6125                6130                6135

Thr Ala Ala Thr Thr Ala Cys Gly Gly Ala Thr Thr Thr Gly Thr
            6140                6145                6150

Thr Cys Ala Cys Cys Thr Gly Thr Cys Ala Gly Cys Thr Gly Gly
            6155                6160                6165

Ala Gly Ala Cys Thr Thr Gly Thr Thr Ala Cys Gly Thr Gly Cys
            6170                6175                6180

Ala Gly Ala Ala Cys Ala Gly Ala Ala Gly Ala Gly Gly Gly Ala
            6185                6190                6195

Gly Gly Gly Gly Thr Cys Thr Ala Ala Gly Thr Ala Thr Gly Gly
            6200                6205                6210

Ala Gly Ala Gly Ala Thr Gly Ala Thr Thr Thr Cys Cys Cys Ala
            6215                6220                6225

Gly Thr Ala Thr Ala Thr Cys Ala Gly Ala Gly Ala Thr Gly Gly
            6230                6235                6240

Ala Cys Thr Gly Ala Thr Ala Gly Thr Ala Cys Cys Thr Cys Ala
            6245                6250                6255

Ala Gly Ala Gly Gly Thr Cys Ala Cys Cys Ala Thr Thr Gly Cys
            6260                6265                6270

Gly Cys Thr Cys Thr Thr Gly Gly Ala Gly Cys Ala Gly Gly Cys
            6275                6280                6285

Cys Ala Thr Gly Ala Ala Gly Gly Ala Ala Ala Ala Cys Thr Thr
            6290                6295                6300

Cys Gly Ala Gly Ala Ala Ala Gly Gly Gly Ala Ala Gly Ala Cys
            6305                6310                6315

Ala Cys Gly Gly Thr Thr Cys Thr Thr Gly Ala Thr Thr Gly Ala
            6320                6325                6330

```
Thr Gly Gly Ala Thr Thr Cys Cys Cys Thr Cys Gly Thr Ala Ala
        6335            6340                6345
Gly Ala Thr Gly Gly Ala Cys Cys Ala Gly Gly Cys Cys Ala Ala
        6350            6355                6360
Ala Ala Cys Thr Thr Thr Thr Gly Ala Gly Gly Ala Ala Ala Ala
        6365            6370                6375
Ala Gly Thr Cys Gly Cys Ala Ala Ala Gly Thr Cys Cys Ala Ala
        6380            6385                6390
Gly Gly Thr Gly Ala Cys Ala Cys Thr Thr Thr Cys Thr Thr
        6395            6400                6405
Thr Gly Ala Thr Thr Gly Thr Cys Cys Cys Gly Ala Ala Thr Cys
        6410            6415                6420
Ala Gly Thr Gly Cys Thr Cys Cys Thr Thr Gly Ala Gly Ala Gly
        6425            6430                6435
Ala Thr Thr Ala Cys Thr Thr Ala Ala Ala Ala Gly Ala Gly Gly
        6440            6445                6450
Ala Cys Ala Gly Ala Cys Ala Ala Gly Cys Gly Gly Ala Ala Gly
        6455            6460                6465
Ala Gly Ala Gly Gly Ala Thr Gly Ala Thr Ala Ala Thr Gly Cys
        6470            6475                6480
Gly Gly Ala Gly Ala Gly Thr Ala Thr Cys Ala Ala Ala Ala Ala
        6485            6490                6495
Ala Ala Gly Ala Thr Thr Cys Ala Ala Ala Ala Cys Ala Thr Thr
        6500            6505                6510
Cys Gly Thr Gly Gly Ala Ala Ala Cys Thr Thr Cys Gly Ala Thr
        6515            6520                6525
Gly Cys Cys Thr Gly Thr Gly Gly Thr Gly Gly Ala Cys Thr Ala
        6530            6535                6540
Thr Thr Thr Cys Gly Gly Gly Ala Ala Gly Cys Ala Ala Gly Gly
        6545            6550                6555
Ala Cys Gly Cys Gly Thr Thr Thr Thr Gly Ala Ala Gly Gly Thr
        6560            6565                6570
Ala Thr Cys Thr Thr Gly Thr Gly Ala Cys Cys Ala Cys Cys Cys
        6575            6580                6585
Thr Gly Thr Gly Gly Ala Thr Cys Ala Ala Gly Thr Gly Thr Ala
        6590            6595                6600
Thr Thr Cys Ala Cys Ala Gly Gly Thr Thr Gly Thr Gly Thr Cys
        6605            6610                6615
Gly Gly Thr Gly Cys Thr Ala Ala Ala Ala Gly Ala Gly Ala Ala
        6620            6625                6630
Gly Gly Gly Gly Ala Thr Cys Thr Thr Thr Gly Cys Cys Gly Ala
        6635            6640                6645
Thr Ala Ala Cys Gly Ala Gly Ala Cys Gly Gly Ala Gly Ala Ala
        6650            6655                6660
Thr Ala Ala Ala Thr Ala Ala Ala Cys Ala Thr Thr Gly Thr Ala
        6665            6670                6675
Ala Thr Ala Ala Gly Ala Thr Thr Ala Gly Ala Cys Thr Gly
        6680            6685                6690
Thr Gly Ala Ala Thr Gly Thr Thr Cys Thr Ala Thr Gly Thr Ala
        6695            6700                6705
Ala Thr Ala Thr Thr Thr Thr Thr Cys Gly Ala Gly Ala Thr Ala
        6710            6715                6720
```

```
Cys Thr Gly Thr Ala Thr Cys Thr Ala Thr Cys Thr Gly Gly Thr
    6725                6730                6735

Gly Thr Ala Cys Cys Gly Thr Ala Thr Cys Ala Cys Thr Cys Thr
    6740                6745                6750

Gly Gly Ala Cys Thr Thr Gly Cys Ala Ala Cys Thr Cys Ala
    6755                6760                6765

Thr Thr Gly Ala Thr Thr Ala Cys Thr Gly Thr Gly Cys Ala
    6770                6775                6780

Ala Thr Gly Gly Gly Cys Ala Ala Gly Ala Ala Gly Gly Ala Thr
    6785                6790                6795

Ala Gly Cys Thr Cys Thr Ala Gly Ala Ala Gly Ala Ala Gly
    6800                6805                6810

Ala Ala Gly Ala Ala Ala Ala Ala Gly Gly Ala Gly Cys Cys Gly
    6815                6820                6825

Cys Cys Thr Gly Ala Ala Gly Ala Gly Cys Thr Gly Gly Ala Thr
    6830                6835                6840

Cys Thr Thr Thr Cys Cys Gly Ala Gly Gly Thr Thr Gly Thr Thr
    6845                6850                6855

Cys Cys Ala Ala Cys Thr Thr Thr Thr Gly Gly Thr Thr Ala Thr
    6860                6865                6870

Gly Ala Gly Gly Ala Ala Thr Thr Thr Cys Ala Thr Gly Thr Thr
    6875                6880                6885

Gly Ala Gly Cys Ala Ala Gly Ala Gly Cys Ala Gly Ala Ala Thr
    6890                6895                6900

Cys Cys Gly Gly Thr Cys Gly Ala Thr Cys Ala Ala Gly Ala Cys
    6905                6910                6915

Gly Ala Ala Cys Thr Thr Gly Ala Cys Gly Gly Cys Cys Ala Thr
    6920                6925                6930

Ala Ala Thr Gly Gly Cys Cys Thr Ala Gly Cys Thr Thr Gly Gly
    6935                6940                6945

Cys Gly Thr Ala Ala Thr Cys Ala Thr Gly Gly Thr Cys Ala Thr
    6950                6955                6960

Ala Gly Cys Thr Gly Thr Thr Thr Cys Cys Thr Gly Thr Gly Thr
    6965                6970                6975

Gly Ala Ala Ala Thr Thr Gly Thr Thr Ala Thr Cys Cys Gly Cys
    6980                6985                6990

Thr Cys Ala Cys Ala Ala Thr Thr Cys Cys Ala Cys Ala Cys Ala
    6995                7000                7005

Ala Cys Ala Thr Ala Cys Gly Ala Gly Cys Cys Gly Gly Ala Ala
    7010                7015                7020

Gly Cys Ala Thr Ala Ala Ala Gly Thr Gly Thr Ala Ala Ala Gly
    7025                7030                7035

Cys Cys Thr Gly Gly Gly Gly Thr Gly Cys Cys Thr Ala Ala Thr
    7040                7045                7050

Gly Ala Gly Thr Gly Ala Gly Cys Thr Ala Ala Cys Thr Cys Ala
    7055                7060                7065

Cys Ala Thr Thr Ala Ala Thr Thr Gly Cys Gly Thr Thr Gly Cys
    7070                7075                7080

Gly Cys Thr Cys Ala Cys Thr Gly Cys Cys Cys Gly Cys Thr Thr
    7085                7090                7095

Thr Cys Cys Ala Gly Thr Cys Gly Gly Gly Ala Ala Ala Cys Cys
    7100                7105                7110

Thr Gly Thr Cys Gly Thr Gly Cys Cys Ala Gly Cys Thr Gly Cys
```

-continued

```
              7115                7120                7125
Ala Thr Thr Ala Ala Thr Gly Ala Ala Thr Cys Gly Gly Cys Cys
              7130                7135                7140
Ala Ala Cys Gly Cys Gly Cys Gly Gly Gly Ala Gly Ala Gly
              7145                7150                7155
Gly Cys Gly Gly Thr Thr Thr Gly Cys Gly Thr Ala Thr Thr Gly
              7160                7165                7170
Gly Gly Cys Gly Cys Thr Cys Thr Thr Cys Cys Gly Cys Thr Thr
              7175                7180                7185
Cys Cys Thr Cys Gly Cys Thr Cys Ala Cys Thr Gly Ala Cys Thr
              7190                7195                7200
Cys Gly Cys Thr Gly Cys Gly Cys Thr Cys Gly Gly Thr Cys Gly
              7205                7210                7215
Thr Thr Cys Gly Gly Cys Thr Gly Cys Gly Gly Cys Gly Ala Gly
              7220                7225                7230
Cys Gly Gly Thr Ala Thr Cys Ala Gly Cys Thr Cys Ala Cys Thr
              7235                7240                7245
Cys Ala Ala Ala Gly Gly Cys Gly Gly Thr Ala Ala Thr Ala Cys
              7250                7255                7260
Gly Gly Thr Thr Ala Thr Cys Cys Ala Cys Ala Gly Ala Ala Thr
              7265                7270                7275
Cys Ala Gly Gly Gly Gly Ala Thr Ala Ala Cys Gly Cys Ala Gly
              7280                7285                7290
Gly Ala Ala Ala Gly Ala Ala Cys Ala Thr Gly Thr Gly Ala Gly
              7295                7300                7305
Cys Ala Ala Ala Ala Gly Gly Cys Cys Ala Gly Cys Ala Ala Ala
              7310                7315                7320
Ala Gly Gly Cys Cys Ala Gly Gly Ala Ala Cys Cys Gly Thr Ala
              7325                7330                7335
Ala Ala Ala Ala Gly Gly Cys Cys Gly Cys Gly Thr Thr Gly Cys
              7340                7345                7350
Thr Gly Gly Cys Gly Thr Thr Thr Thr Thr Cys Cys Ala Thr Ala
              7355                7360                7365
Gly Gly Cys Thr Cys Cys Gly Cys Cys Cys Cys Cys Cys Thr Gly
              7370                7375                7380
Ala Cys Gly Ala Gly Cys Ala Thr Cys Ala Cys Ala Ala Ala Ala
              7385                7390                7395
Ala Thr Cys Gly Ala Cys Gly Cys Thr Cys Ala Ala Gly Thr Cys
              7400                7405                7410
Ala Gly Ala Gly Gly Thr Gly Gly Cys Gly Ala Ala Ala Cys Cys
              7415                7420                7425
Cys Gly Ala Cys Ala Gly Gly Ala Cys Thr Ala Thr Ala Ala Ala
              7430                7435                7440
Gly Ala Thr Ala Cys Cys Ala Gly Gly Cys Gly Thr Thr Thr Cys
              7445                7450                7455
Cys Cys Cys Cys Thr Gly Gly Ala Ala Gly Cys Thr Cys Cys Cys
              7460                7465                7470
Thr Cys Gly Thr Gly Cys Gly Cys Thr Cys Thr Cys Cys Thr Gly
              7475                7480                7485
Thr Thr Cys Cys Gly Ala Cys Cys Thr Gly Cys Cys Gly Cys
              7490                7495                7500
Thr Thr Ala Cys Cys Gly Gly Ala Thr Ala Cys Cys Thr Gly Thr
              7505                7510                7515
```

-continued

```
Cys Cys Gly Cys Cys Thr Thr Thr Cys Thr Cys Cys Thr Thr
7520            7525                7530
Cys Gly Gly Gly Ala Ala Gly Cys Gly Thr Gly Gly Cys Gly Cys
7535            7540                7545
Thr Thr Thr Cys Thr Cys Ala Thr Ala Gly Cys Thr Cys Ala Cys
7550            7555                7560
Gly Cys Thr Gly Thr Ala Gly Gly Thr Ala Thr Cys Thr Cys Ala
7565            7570                7575
Gly Thr Thr Cys Gly Gly Thr Gly Thr Ala Gly Thr Cys Gly
7580            7585                7590
Thr Thr Cys Gly Cys Thr Cys Cys Ala Ala Gly Cys Thr Gly Gly
7595            7600                7605
Gly Cys Thr Gly Thr Gly Thr Gly Cys Ala Cys Gly Ala Ala Cys
7610            7615                7620
Cys Cys Cys Cys Cys Gly Thr Thr Cys Ala Gly Cys Cys Cys Gly
7625            7630                7635
Ala Cys Cys Gly Cys Thr Gly Cys Gly Cys Cys Thr Thr Ala Thr
7640            7645                7650
Cys Cys Gly Gly Thr Ala Ala Cys Thr Ala Thr Cys Gly Thr Cys
7655            7660                7665
Thr Thr Gly Ala Gly Thr Cys Cys Ala Ala Cys Cys Cys Gly Gly
7670            7675                7680
Thr Ala Ala Gly Ala Cys Ala Cys Gly Ala Cys Thr Thr Ala Thr
7685            7690                7695
Cys Gly Cys Cys Ala Cys Thr Gly Gly Cys Ala Gly Cys Ala Gly
7700            7705                7710
Cys Cys Ala Cys Thr Gly Gly Thr Ala Ala Cys Ala Gly Gly Ala
7715            7720                7725
Thr Thr Ala Gly Cys Ala Gly Ala Gly Cys Gly Ala Gly Gly Thr
7730            7735                7740
Ala Thr Gly Thr Ala Gly Gly Cys Gly Gly Thr Gly Cys Thr Ala
7745            7750                7755
Cys Ala Gly Ala Gly Thr Thr Cys Thr Thr Gly Ala Ala Gly Thr
7760            7765                7770
Gly Gly Thr Gly Gly Cys Cys Thr Ala Ala Cys Thr Ala Cys Gly
7775            7780                7785
Gly Cys Thr Ala Cys Ala Cys Thr Ala Gly Ala Ala Gly Gly Ala
7790            7795                7800
Cys Ala Gly Thr Ala Thr Thr Thr Gly Gly Thr Ala Thr Cys Thr
7805            7810                7815
Gly Cys Gly Cys Thr Cys Thr Gly Cys Thr Gly Ala Ala Gly Cys
7820            7825                7830
Cys Ala Gly Thr Thr Ala Cys Cys Thr Thr Cys Gly Gly Ala Ala
7835            7840                7845
Ala Ala Ala Gly Ala Gly Thr Thr Gly Gly Thr Ala Gly Cys Thr
7850            7855                7860
Cys Thr Thr Gly Ala Thr Cys Cys Gly Gly Cys Ala Ala Ala Cys
7865            7870                7875
Ala Ala Ala Cys Cys Ala Cys Cys Gly Cys Thr Gly Gly Thr Ala
7880            7885                7890
Gly Cys Gly Gly Thr Gly Gly Thr Thr Thr Thr Thr Thr Thr Gly
7895            7900                7905
```

-continued

| | | | | | | | | | | | |
|---|---|---|---|---|---|---|---|---|---|---|---|
| Thr | Thr | Thr | Gly | Cys | Ala | Ala | Gly | Cys | Ala | Gly | Cys | Ala | Gly | Ala |
| | | 7910 | | | | 7915 | | | | 7920 | |
| Thr | Thr | Ala | Cys | Gly | Cys | Gly | Cys | Ala | Gly | Ala | Ala | Ala | Ala | Ala |
| | | 7925 | | | | 7930 | | | | 7935 | |
| Ala | Ala | Gly | Gly | Ala | Thr | Cys | Thr | Cys | Ala | Ala | Gly | Ala | Ala | Gly |
| | | 7940 | | | | 7945 | | | | 7950 | |
| Ala | Thr | Cys | Cys | Thr | Thr | Thr | Gly | Ala | Thr | Cys | Thr | Thr | Thr | Thr |
| | | 7955 | | | | 7960 | | | | 7965 | |
| Cys | Thr | Ala | Cys | Gly | Gly | Gly | Thr | Cys | Thr | Gly | Ala | Cys | Gly |
| | | 7970 | | | | 7975 | | | | 7980 | |
| Cys | Thr | Cys | Ala | Gly | Thr | Gly | Gly | Ala | Ala | Cys | Gly | Ala | Ala | Ala |
| | | 7985 | | | | 7990 | | | | 7995 | |
| Ala | Cys | Thr | Cys | Ala | Cys | Gly | Thr | Thr | Ala | Ala | Gly | Gly | Gly | Ala |
| | | 8000 | | | | 8005 | | | | 8010 | |
| Thr | Thr | Thr | Thr | Gly | Gly | Thr | Cys | Ala | Thr | Gly | Ala | Gly | Ala | Thr |
| | | 8015 | | | | 8020 | | | | 8025 | |
| Thr | Ala | Thr | Cys | Ala | Ala | Ala | Ala | Ala | Gly | Gly | Ala | Thr | Cys | Thr |
| | | 8030 | | | | 8035 | | | | 8040 | |
| Thr | Cys | Ala | Cys | Cys | Thr | Ala | Gly | Ala | Thr | Cys | Cys | Thr | Thr | Thr |
| | | 8045 | | | | 8050 | | | | 8055 | |
| Thr | Ala | Ala | Ala | Thr | Thr | Ala | Ala | Ala | Ala | Thr | Gly | Ala | Ala | Gly |
| | | 8060 | | | | 8065 | | | | 8070 | |
| Thr | Thr | Thr | Thr | Ala | Ala | Ala | Thr | Cys | Ala | Ala | Thr | Cys | Thr |
| | | 8075 | | | | 8080 | | | | 8085 | |
| Ala | Ala | Ala | Gly | Thr | Ala | Thr | Ala | Thr | Ala | Thr | Gly | Ala | Gly | Thr |
| | | 8090 | | | | 8095 | | | | 8100 | |
| Ala | Ala | Ala | Cys | Thr | Thr | Gly | Gly | Thr | Cys | Thr | Gly | Ala | Cys | Ala |
| | | 8105 | | | | 8110 | | | | 8115 | |
| Gly | Thr | Thr | Ala | Cys | Cys | Ala | Ala | Thr | Gly | Cys | Thr | Thr | Ala | Ala |
| | | 8120 | | | | 8125 | | | | 8130 | |
| Thr | Cys | Ala | Gly | Thr | Gly | Ala | Gly | Gly | Cys | Ala | Cys | Cys | Thr | Ala |
| | | 8135 | | | | 8140 | | | | 8145 | |
| Thr | Cys | Thr | Cys | Ala | Gly | Cys | Gly | Ala | Thr | Cys | Thr | Gly | Thr | Cys |
| | | 8150 | | | | 8155 | | | | 8160 | |
| Thr | Ala | Thr | Thr | Thr | Cys | Gly | Thr | Thr | Cys | Ala | Thr | Cys | Cys | Ala |
| | | 8165 | | | | 8170 | | | | 8175 | |
| Thr | Ala | Gly | Thr | Thr | Gly | Cys | Cys | Thr | Gly | Ala | Cys | Thr | Cys | Cys |
| | | 8180 | | | | 8185 | | | | 8190 | |
| Cys | Cys | Gly | Thr | Cys | Gly | Thr | Gly | Thr | Ala | Gly | Ala | Thr | Ala | Ala |
| | | 8195 | | | | 8200 | | | | 8205 | |
| Cys | Thr | Ala | Cys | Gly | Ala | Thr | Ala | Cys | Gly | Gly | Gly | Ala | Gly | Gly |
| | | 8210 | | | | 8215 | | | | 8220 | |
| Gly | Cys | Thr | Thr | Ala | Cys | Cys | Ala | Thr | Cys | Thr | Gly | Gly | Cys | Cys |
| | | 8225 | | | | 8230 | | | | 8235 | |
| Cys | Cys | Ala | Gly | Thr | Gly | Cys | Thr | Gly | Cys | Ala | Ala | Thr | Gly | Ala |
| | | 8240 | | | | 8245 | | | | 8250 | |
| Thr | Ala | Cys | Cys | Gly | Cys | Gly | Ala | Gly | Ala | Cys | Cys | Ala | Cys | Gly |
| | | 8255 | | | | 8260 | | | | 8265 | |
| Cys | Thr | Cys | Ala | Cys | Cys | Gly | Gly | Cys | Thr | Cys | Cys | Ala | Gly | Ala |
| | | 8270 | | | | 8275 | | | | 8280 | |
| Thr | Thr | Thr | Ala | Thr | Cys | Ala | Gly | Cys | Ala | Ala | Thr | Ala | Ala | Ala |
| | | 8285 | | | | 8290 | | | | 8295 | |
| Cys | Cys | Ala | Gly | Cys | Cys | Ala | Gly | Cys | Cys | Gly | Gly | Ala | Ala |

```
                    8300              8305              8310

Gly Gly Gly Cys Cys Gly Ala Gly Cys Gly Cys Ala Gly Ala Ala
        8315              8320              8325

Gly Thr Gly Gly Thr Cys Cys Thr Gly Cys Ala Ala Cys Thr Thr
        8330              8335              8340

Thr Ala Thr Cys Cys Gly Cys Cys Thr Cys Cys Ala Thr Cys Cys
        8345              8350              8355

Ala Gly Thr Cys Thr Ala Thr Thr Ala Thr Thr Gly Thr Thr
        8360              8365              8370

Gly Cys Cys Gly Gly Gly Ala Ala Gly Cys Thr Ala Gly Ala Gly
        8375              8380              8385

Thr Ala Ala Gly Thr Ala Gly Thr Thr Cys Gly Cys Cys Ala Gly
        8390              8395              8400

Thr Thr Ala Ala Thr Ala Gly Thr Thr Thr Gly Cys Gly Cys Ala
        8405              8410              8415

Ala Cys Gly Thr Thr Gly Thr Thr Gly Cys Cys Ala Thr Thr Gly
        8420              8425              8430

Cys Thr Ala Cys Ala Gly Gly Cys Ala Thr Cys Gly Thr Gly Gly
        8435              8440              8445

Thr Gly Thr Cys Ala Cys Gly Cys Thr Cys Gly Thr Cys Gly Thr
        8450              8455              8460

Thr Thr Gly Gly Thr Ala Thr Gly Gly Cys Thr Thr Cys Ala Thr
        8465              8470              8475

Thr Cys Ala Gly Cys Thr Cys Cys Gly Gly Thr Thr Cys Cys Cys
        8480              8485              8490

Ala Ala Cys Gly Ala Thr Cys Ala Ala Gly Gly Cys Gly Ala Gly
        8495              8500              8505

Thr Thr Ala Cys Ala Thr Gly Ala Thr Cys Cys Cys Cys Cys Ala
        8510              8515              8520

Thr Gly Thr Thr Gly Thr Gly Cys Ala Ala Ala Ala Ala Ala Gly
        8525              8530              8535

Cys Gly Gly Thr Thr Ala Gly Cys Thr Cys Cys Thr Thr Cys Gly
        8540              8545              8550

Gly Thr Cys Cys Thr Cys Cys Gly Ala Thr Cys Gly Thr Thr Gly
        8555              8560              8565

Thr Cys Ala Gly Ala Ala Gly Thr Ala Ala Gly Thr Thr Gly Gly
        8570              8575              8580

Cys Cys Gly Cys Ala Gly Thr Gly Thr Thr Ala Thr Cys Ala Cys
        8585              8590              8595

Thr Cys Ala Thr Gly Gly Thr Thr Ala Thr Gly Gly Cys Ala Gly
        8600              8605              8610

Cys Ala Cys Thr Gly Cys Ala Thr Ala Ala Thr Thr Cys Thr Cys
        8615              8620              8625

Thr Thr Ala Cys Thr Gly Thr Cys Ala Thr Gly Cys Cys Ala Thr
        8630              8635              8640

Cys Cys Gly Thr Ala Ala Gly Ala Thr Gly Cys Thr Thr Thr Thr
        8645              8650              8655

Cys Thr Gly Thr Gly Ala Cys Thr Gly Gly Thr Gly Ala Gly Thr
        8660              8665              8670

Ala Cys Thr Cys Ala Ala Cys Cys Ala Ala Gly Thr Cys Ala Thr
        8675              8680              8685

Thr Cys Thr Gly Ala Gly Ala Ala Thr Ala Gly Thr Gly Thr Ala
        8690              8695              8700
```

```
Thr Gly Cys Gly Gly Cys Gly Ala Cys Gly Ala Gly Thr Thr
    8705                8710                8715

Gly Cys Thr Cys Thr Thr Gly Cys Cys Cys Gly Gly Cys Gly Thr
    8720                8725                8730

Cys Ala Ala Thr Ala Cys Gly Gly Gly Ala Thr Ala Ala Thr Ala
    8735                8740                8745

Cys Cys Gly Cys Gly Cys Ala Cys Ala Thr Ala Gly Cys Ala
    8750                8755                8760

Gly Ala Ala Cys Thr Thr Ala Ala Ala Gly Thr Gly Cys
    8765                8770                8775

Thr Cys Ala Thr Cys Ala Thr Gly Gly Ala Ala Ala Ala Cys
    8780                8785                8790

Gly Thr Thr Cys Thr Thr Cys Gly Gly Gly Gly Cys Gly Ala Ala
    8795                8800                8805

Ala Ala Cys Thr Cys Thr Cys Ala Ala Gly Gly Ala Thr Cys Thr
    8810                8815                8820

Thr Ala Cys Cys Gly Cys Thr Gly Thr Thr Gly Ala Gly Ala Thr
    8825                8830                8835

Cys Cys Ala Gly Thr Thr Cys Gly Ala Thr Gly Thr Ala Ala Cys
    8840                8845                8850

Cys Cys Ala Cys Thr Cys Gly Thr Gly Cys Ala Cys Cys Cys Ala
    8855                8860                8865

Ala Cys Thr Gly Ala Thr Cys Thr Thr Cys Ala Gly Cys Ala Thr
    8870                8875                8880

Cys Thr Thr Thr Thr Ala Cys Thr Thr Thr Cys Ala Cys Cys Ala
    8885                8890                8895

Gly Cys Gly Thr Thr Thr Cys Thr Gly Gly Gly Thr Gly Ala Gly
    8900                8905                8910

Cys Ala Ala Ala Ala Cys Ala Gly Gly Ala Ala Gly Gly Cys
    8915                8920                8925

Ala Ala Ala Ala Thr Gly Cys Cys Gly Cys Ala Ala Ala Ala Ala
    8930                8935                8940

Ala Gly Gly Gly Ala Ala Thr Ala Ala Gly Gly Gly Cys Gly Ala
    8945                8950                8955

Cys Ala Cys Gly Gly Ala Ala Ala Thr Gly Thr Thr Gly Ala Ala
    8960                8965                8970

Thr Ala Cys Thr Cys Ala Thr Ala Cys Thr Cys Thr Thr Cys Cys
    8975                8980                8985

Thr Thr Thr Thr Thr Cys Ala Ala Thr Ala Thr Thr Ala Thr Thr
    8990                8995                9000

Gly Ala Ala Gly Cys Ala Thr Thr Thr Ala Thr Cys Ala Gly Gly
    9005                9010                9015

Gly Thr Thr Ala Thr Thr Gly Thr Cys Thr Cys Ala Thr Gly Ala
    9020                9025                9030

Gly Cys Gly Gly Ala Thr Ala Cys Ala Thr Ala Thr Thr Thr Gly
    9035                9040                9045

Ala Ala Thr Gly Thr Ala Thr Thr Thr Ala Gly Ala Ala Ala Ala
    9050                9055                9060

Ala Thr Ala Ala Ala Cys Ala Ala Ala Thr Ala Gly Gly Gly Gly
    9065                9070                9075

Thr Thr Cys Cys Gly Cys Gly Cys Ala Cys Ala Thr Thr Thr Cys
    9080                9085                9090
```

-continued

```
Cys Cys Cys Gly Ala Ala Ala  Ala Gly Thr Gly Cys  Cys Ala Cys
    9095              9100              9105

Cys Thr Gly Ala Cys Gly Thr  Cys Thr Ala Ala Gly  Ala Ala Ala
    9110              9115              9120

Cys Cys Ala Thr Thr Ala Thr  Thr Ala Thr Cys Ala  Thr Gly Ala
    9125              9130              9135

Cys Ala Thr Thr Ala Ala Cys  Cys Thr Ala Thr Ala  Ala Ala Ala
    9140              9145              9150

Ala Thr Ala Gly Gly Cys Gly  Thr Ala Thr Cys Ala  Cys Gly Ala
    9155              9160              9165

Gly Gly Cys Cys Cys Thr Thr  Thr Cys Gly Thr Cys
    9170              9175              9180

<210> SEQ ID NO 7
<211> LENGTH: 4
<212> TYPE: PRT
<213> ORGANISM: Artificial sequence
<220> FEATURE:
<223> OTHER INFORMATION: Linker

<400> SEQUENCE: 7

Gly Gly Gly Gly
1
```

SURFACE, ANCHORED FC-BAIT ANTIBODY DISPLAY SYSTEM

This application is a divisional application of U.S. patent application Ser. No. 15/164,773, filed May 25, 2016; which is a divisional application of U.S. patent application Ser. No. 13/990,941, filed Aug. 6, 2013, and which is U.S. Pat. No. 9,365,846; which is the national phase of international patent application no. PCT/US2011/062286 filed Nov. 29, 2011, which claims the benefit of U.S. provisional patent application No. 61/458,771, filed Dec. 1, 2010; each of which is herein incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "23002_US_DIV2_SEQTXT_05MAY2020.txt", creation date of May 5, 2020, and a size of 102 Kb. This sequence listing submitted via EFS-Web is part of the specification and is herein incorporated by reference in its entirety.

FIELD OF THE INVENTION

The field of the invention relates to antibody display systems and methods of use for identifying antibodies that bind specifically to an antigen.

BACKGROUND OF THE INVENTION

A technique for constructing and screening antibody libraries is phage display, whereby the protein of interest is expressed as a polypeptide fusion to a bacteriophage coat protein and subsequently screened by binding to immobilized or soluble biotinylated ligand.

Phage display, however, has several shortcomings. For example, some eukaryotic secreted proteins and cell surface proteins require post-translational modifications such as glycosylation or extensive disulfide isomerization, which are unavailable in bacterial cells.

Current yeast surface antibody display systems, such as cold capture, also suffer from various drawbacks. In the cold capture antibody display system, at low temperatures, the process of antibody release from host cell transport vesicles is delayed, so that the secreted antibody can be assayed on the cell surface for antigen binding. The cold capture method suffers from a low signal-to-noise ratio and identification of an antibody with specificity for the target antigen depends heavily on cellular expression levels of the antibody.

The affinity matrix system couples antibodies to the host cell surface, e.g., by biotin, where they can be assayed for antigen binding. The affinity matrix system exhibits a high incidence of cross-contamination between antibody clones. Antibodies may become decoupled from the host cell and, thus lose their link to the polynucleotides encoding their immunoglobulin chains.

Full length antibody display systems tether the full length antibody on the host cell surface by binding an immunoglobulin binding protein, such as protein A, that is fused to a cell surface anchor protein. The host cell contains polynucleotides encoding the antibody immunoglobulin chains. Typically, binding of the antibody occurs after the immunoglobulin binding protein is expressed on the cell surface. This system, thus, leads to some erroneous binding of the antibody to host cells that do not express the antibody.

SUMMARY OF THE INVENTION

The present invention provides, in part, an antibody display system that does not suffer from shortcomings of currently available systems. The present invention also allows coupling of antibody display to production strain selection. The strain discovered by surface display screening can be turned into the production strain while preserving the antibody sequence and integrity. This method enables screening for parameters such as antibody folding and expression.

The present invention provides an antibody display system comprising: (a) an isolated eukaryotic host cell (e.g., a *Pichia* cell such as *Pichia pastoris*); (b) a bait comprising a Fc immunoglobulin domain or functional fragment thereof (e.g., comprising a CH3, CH2-CH3 or VH—CH1 polypeptide) (e.g., human) fused to a surface anchor polypeptide or functional fragment thereof (e.g., wherein the cell comprises a polynucleotide encoding the bait); (c) one or more polynucleotides encoding an immunoglobulin light chain variable region; and (d) one or more polynucleotides encoding an immunoglobulin heavy chain variable region. Optionally, the antibody display system further comprises a non-tethered full antibody comprising said immunoglobulin light and heavy chains; and/or monovalent antibody fragment which is complexed with the Fc moiety of the bait. In an embodiment of the invention, said one or more polynucleotides encoding an immunoglobulin light chain variable region is from a genetically diverse population of immunoglobulin light chain variable regions (e.g., an immunoglobulin library); and/or, wherein said one or more polynucleotides encoding an immunoglobulin heavy chain variable region is from a genetically diverse population of immunoglobulin heavy chain variable regions (e.g., an immunoglobulin library). In an embodiment of the invention, the host cell comprises a polynucleotide encoding the bait which is operably associated with a regulatable promoter (e.g., a GUT1 promoter, a GADPH promoter or a PCK1 promoter).

The present invention also provides an isolated bait polypeptide, e.g., comprising an Fc immunoglobulin domain or functional fragment thereof (e.g., wherein the Fc is derived from an IgG1, IgG2, IgG3 or IgG4 immunoglobulin; e.g., human, e.g., comprising a VH—CH1, a CH2-CH3 or a CH3 polypeptide) fused to a surface anchor polypeptide (e.g., SED1) or functional fragment thereof. Any isolated polynucleotide encoding such a polypeptide; vectors including the polynucleotides and isolated host cells comprising the polynucleotides and vectors form part of the present invention. The scope of the present invention includes an isolated host cell (e.g., a eukaryotic host cell such as *Pichia*, e.g., *Pichia pastoris*) further comprising one or more polynucleotides encoding an immunoglobulin light chain variable region (e.g., from a library); and/or one or more polynucleotides encoding an immunoglobulin heavy chain variable region (e.g., from a library). In an embodiment of the invention, a host cell of the present invention includes the polypeptide located on the surface of the cell, e.g., on the cell membrane.

The present invention comprises an isolated host cell (e.g., *Pichia* such as *Pichia pastoris*) comprising a bait polypeptide complexed with an Fc/antigen-binding fragment, e.g., located at the host cell surface by a cell surface anchor (such as SED1) that is part of the bait; optionally wherein the Fc/antigen-binding fragment is bound to an antigen; optionally comprising an antibody or antigen-binding fragment thereof that comprises the light and heavy chain immunoglobulins of the Fc/antigen-binding fragment; for example, wherein the host cell comprises one or more polynucleotides encoding e.g., the bait, the light chain immunoglobulin and/or the heavy chain immunoglobulin.

The present invention also provides a composition comprising the host cell of the present invention (see e.g., above), further comprising a non-tethered full antibody comprising said immunoglobulin light and heavy chains; and/or an Fc/antigen-binding fragment of an antibody (e.g., a monovalent antibody fragment) which is complexed with the Fc moiety of the bait. In an embodiment of the invention, said full antibody or Fc/antigen-binding fragment is complexed with an antigen.

The present invention provides a method for determining if an antibody or antigen-binding fragment thereof specifically binds to an antigen comprising contacting an antibody display system with said antigen; wherein the antibody display system comprises: (a) an isolated eukaryotic host cell (e.g., *Pichia* such as *Pichia pastoris*) comprising a polynucleotide encoding an immunoglobulin light chain (e.g., from a library); and a polynucleotide encoding an immunoglobulin heavy chain (e.g., from a library); and (b) a bait comprising an Fc immunoglobulin domain or functional fragment thereof (e.g., human, e.g., comprising a VH—CH1, CH2-CH3 or CH3 polypeptide) fused to a surface anchor polypeptide or functional fragment thereof (e.g., SED1) on the surface of said eukaryotic host cell; wherein the Fc of said bait complexes with an Fc/antigen-binding fragment (e.g., a monovalent antibody fragment) comprising said immunoglobulin heavy and immunoglobulin light chains on the surface of the host cell; and determining if said Fc/antigen-binding fragment (e.g., monovalent antibody fragment) specifically binds to said antigen; wherein the antibody is determined to specifically bind said antigen if the monovalent antibody fragment specifically binds to said antigen. In an embodiment of the invention, the method further comprises isolating the polynucleotide(s) and, optionally, determining the nucleotide sequence. In an embodiment of the invention, the method further comprises inhibiting expression of said bait, then determining the affinity of said identified antibody or antigen-binding fragment thereof for said antigen. In an embodiment of the invention, the method further comprises recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

The present invention also provides a method for identifying: (i) an antibody or antigen-binding fragment thereof that binds specifically to an antigen; or (ii) a polynucleotide encoding an immunoglobulin heavy chain of said antibody or fragment (e.g., from a library) and/or a polynucleotide encoding an immunoglobulin light chain of said antibody or fragment (e.g., from a library); comprising contacting an antibody display system with said antigen wherein the antibody display system comprises: (a) an isolated eukaryotic host cell (e.g., *Pichia* such as *Pichia pastoris*) comprising a polynucleotide encoding an immunoglobulin light chain; and a polynucleotide encoding an immunoglobulin heavy chain; and
(b) a bait comprising an Fc immunoglobulin domain or functional fragment thereof (e.g., human; e.g., comprising a VH—CH1, CH2-CH3 or CH3 polypeptide) fused to a surface anchor polypeptide or functional fragment thereof (e.g., SED1) on the surface of said eukaryotic host cell; wherein the Fc of said bait complexes with an Fc/antigen-binding fragment (e.g., a monovalent antibody fragment) comprising said immunoglobulin heavy and immunoglobulin light chains on the surface of the host cell; and determining if said Fc/antigen-binding fragment (e.g., monovalent antibody fragment) specifically binds to said antigen; wherein the antibody or fragment or polynucleotide is identified if said specific binding to said antigen is observed. In an embodiment of the invention, the method further comprises isolating the polynucleotide(s) and, optionally, determining the nucleotide sequence. In an embodiment of the invention, the method further comprises inhibiting expression of said bait, then determining the affinity of said identified antibody or antigen-binding fragment thereof for said antigen. In an embodiment of the invention, the method further comprises recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

The present invention also provides a method for making an antibody display system comprising: (a) an isolated eukaryotic host cell (e.g., *Pichia* such as *Pichia pastoris*); (b) a bait comprising a human Fc immunoglobulin domain or functional fragment thereof (e.g., human; e.g., comprising a VH—CH1, CH2-CH3 or CH3 polypeptide) fused to a surface anchor polypeptide or functional fragment thereof (e.g., SEDT); (c) one or more polynucleotides encoding an immunoglobulin light chain variable region (e.g., from a library); (d) one or more polynucleotides encoding an immunoglobulin heavy chain variable region (e.g., from a library); comprising introducing, into said eukaryotic host cell, a polynucleotide encoding said bait, said one or more polynucleotides encoding an immunoglobulin light chain variable region; and said one or more polynucleotides encoding an immunoglobulin heavy chain variable region.

The present invention also provides a method for making an antibody or antigen-binding fragment thereof comprising introducing, into an isolated eukaryotic host cell (e.g., *Pichia* such as *Pichia pastoris*) comprising a bait that includes a human Fc immunoglobulin domain or functional fragment thereof (e.g., human; e.g., comprising a VH—CH1, CH2-CH3 or CH3 polypeptide) fused to a surface anchor polypeptide or functional fragment thereof (e.g., SED1), one or more polynucleotides encoding an immunoglobulin light chain variable region; and/or one or more polynucleotides encoding an immunoglobulin heavy chain variable region; and culturing the host cell under condition whereby the polynucleotides encoding the immunoglobulin chains are expressed and an antibody or antigen-binding fragment thereof is formed from said chains; wherein said bait is operably associated with a regulatable promoter (e.g., a GUT1 promoter, a GADPH promoter or a PCK1 promoter) and bait expression is inhibited when said immunoglobulin chains are expressed.

The present invention further comprises a method for making an antibody or antigen binding fragment thereof comprising culturing an isolated eukaryotic host cell (e.g., *Pichia pastoris*) in a growth medium under conditions allowing expression of an immunoglobulin light chain and an immunoglobulin heavy chain of said antibody or fragment; wherein the eukaryotic host cell comprises: (i) a polynucleotide encoding said immunoglobulin light chain;

and a polynucleotide encoding said immunoglobulin heavy chain of said antibody or fragment (e.g., wherein said chains are encoded by one common polynucleotide or two separate polynucleotides; and/or, wherein said one or both of said polynucleotides were obtained from a library or from a single clonal source); and (ii) a bait comprising an Fc immunoglobulin domain or functional fragment thereof (e.g., human; e.g., comprising a VH—CH1, CH2-CH3 or CH3 polypeptide) fused to a surface anchor polypeptide or functional fragment thereof on the surface of said eukaryotic host cell; wherein the Fc of said bait complexes with an Fc/antigen-binding fragment (e.g., an monovalent antibody fragment) comprising said immunoglobulin heavy and immunoglobulin light chains on the surface of the host cell; and wherein the expression of the bait is optionally inhibited; wherein said antibody or fragment is optionally secreted from said eukaryotic host cell; optionally comprising isolating said antibody or fragment from said eukaryotic host cell and medium.

The present invention further provides a method for determining the effect of a sugar (e.g., an O-glycan and/or an N-glycan, e.g., any of those discussed herein) on an antibody or antigen-binding fragment thereof which specifically binds to an antigen comprising contacting an antibody display system with said antigen; wherein the antibody display system comprises:
(a) an isolated eukaryotic controlled glycosylation host cell (e.g., *Pichia pastoris*) comprising a polynucleotide encoding an immunoglobulin light chain; and a polynucleotide encoding an immunoglobulin heavy chain; and (b) a bait comprising an Fc immunoglobulin domain or functional fragment thereof (e.g., human; e.g., comprising a VH—CH1, CH2-CH3 or CH3 polypeptide) comprising said sugar fused to a surface anchor polypeptide or functional fragment thereof on the surface of said host cell;
wherein the Fc of said bait complexes with the Fc/antigen-binding fragment comprising said immunoglobulin heavy and immunoglobulin light chains on the surface of the host cell; wherein said heavy and/or light chain comprises said sugar;
determining if said Fc/antigen-binding fragment specifically binds to said antigen; determining the binding affinity of the antibody or antigen-binding fragment thereof comprising said sugar for the antigen; and comparing the affinity of the antibody or antigen-binding fragment thereof for the antigen with affinity for the antigen of an otherwise identical antibody or antigen-binding fragment thereof which lacks said sugar; wherein the sugar is determined to increase affinity for the antigen if the affinity of the antibody or antigen-binding fragment thereof comprising said sugar is higher than the affinity of the antibody or antigen-binding fragment thereof which lacks the sugar, and/or wherein the sugar is determined to decrease affinity for the antigen if the affinity of antibody or antigen-binding fragment thereof comprising said sugar is lower than the affinity of the antibody or antigen-binding fragment thereof which lacks the sugar.

BRIEF DESCRIPTION OF THE FIGURES

FIG. 3A shows an ELISA measuring the concentration of Kappa light chain was used to determine the concentration of secreted antibodies from the strains explained in Table 1. Lane 1 was serially diluted ELISA standard; Lanes 2-3 contained material generated by strains in Table 1 without the surface anchored Fc bait (SAFE); Lanes 5-10 contained the same strains plus SAFE. Y8316 did not express antibodies and was used as a negative control. FIG. 3B shows supernatants generated by the strains shown in FIG. 3A run on Protein A columns to capture secreted antibodies. In FIG. 3C eluted IgGs were run on (c) non-reducing SDS-PAGE.

FIG. 4A shows parental strains expressing anti-HER2 and anti-PCSK9 with no Fc-SEDT bait; FIG. 4B shows anti-Her2 displaying cells with and without the bait; FIG. 4C shows anti-PCSK9 displaying cells with and without bait

FIG. 7A and FIG. 7B show PCSK9 and Kappa ELISA analysis of presorted BP550 and BP551 library and round 2 sorted pools thereof, respectively.

DETAILED DESCRIPTION OF THE INVENTION

Figure 1:
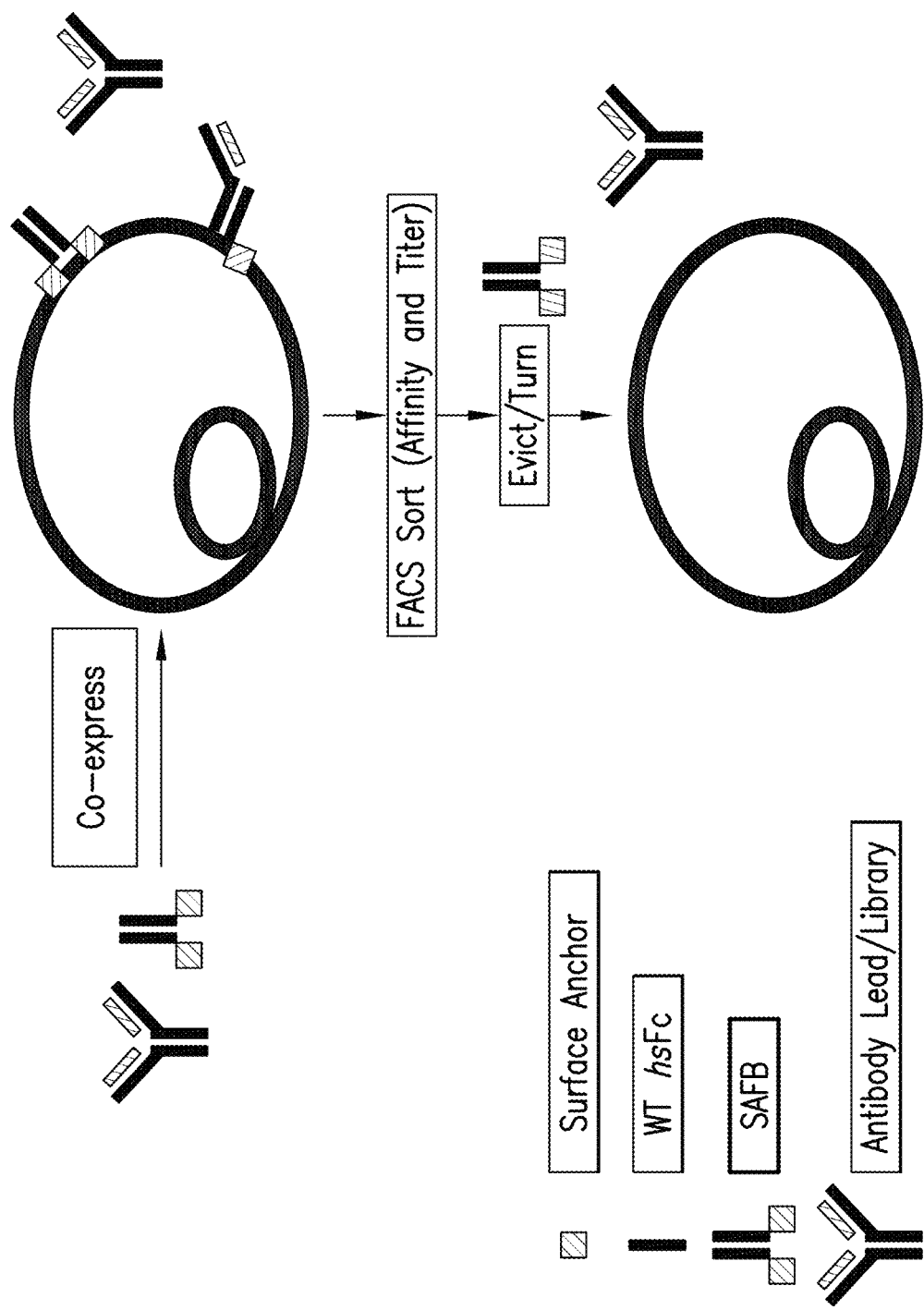
FIG. 1 shows the antibody display system of the present invention and a method of use thereof. Polynucleotide encoding an antibody and bait are co-expressed in *Pichia pastoris*. The polynucleotide encoding one or both of the antibody immunoglobulin chains can be from a library or can be from a single clonal source. The *Pichia* cell expresses the bait on the cell surface, some of such baits are bound by a monovalent antibody fragment (comprising one heavy and one light chain) of the antibody that is also expressed. Some expressed antibody escapes bait binding and is, thus, soluble. Expression of the antibody on the cell can be confirmed by FACS analysis and a titer of the cellular antibody expression level can also be determined. The bait expression is turned off or the polynucleotide encoding the bait is evicted (or knocked-out) from the cell. The resulting cell expresses only the polynucleotide encoding the antibody heavy and light chains and produces only full soluble antibody. Cellular expression levels of the antibody can then be confirmed and a determination of the antibody affinity can also be performed.

The present invention provides a method and system for antibody surface display that simultaneously features a display mode and full antibody secretion mode. Host cells secrete full antibody and display Fc/antigen-binding fragments on the cell surface. This method utilizes an Fc fusion (e.g., fused at the N- or C-terminus) with a cell surface protein as "bait" that is covalently coupled to the cell surface (e.g., the cell wall) or embedded (partially or fully) in the cell membrane (e.g., as a transmembrane protein) and that is co-expressed with an antibody (e.g., a single specific antibody from a clonal source or an antibody from a library). In the endoplasmic reticulum, where antibody molecules normally dimerize to form the full antibody molecule, a surface anchored Fc fusion "bait" heterodimerizes with a monovalent antibody fragment creating a complex that is displayed on the cell surface. Monovalent antibody fragments on the cell surface can bind antigen.

The antibody system of the present invention can be employed in any host cell (e.g., yeast, mammalian cells, bacteria) wherein a bait can be expressed on the host cell surface and an Fc/antigen-binding fragment can bind to the bait.

Homodimerization of full antibody still occurs allowing secretion of full antibody molecules into the culture supernatant. The secreted full antibody can be used, e.g., for preclinical studies, e.g., after isolation.

If desired, bait can be knocked-out or mutated or its expression can be turned off to create a strain producing only the full antibody.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); Oligonucleotide Synthesis (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A library is, typically, a collection of related but diverse polynucleotides that are, in general, in a common vector backbone. For example, a light chain or heavy chain immunoglobulin library may contain polynucleotides, in a common vector backbone, that encode light and/or heavy chain immunoglobulins which are diverse but related in their nucleotide sequence; for example, which immunoglobulins are functionally diverse in their abilities to form complexes with other immunoglobulins, e.g., in an antibody display system of the present invention, and bind a particular antigen.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be spliced (if it contains introns) and translated into a protein encoded by the coding sequence. Thus, a bait gene can be operably associated with a promoter, such as a regulatable promoter or a constitutive promoter.

Polynucleotides discussed herein form part of the present invention. A "polynucleotide", "nucleic acid" or "nucleic acid molecule" include DNA and RNA, single or double stranded.

Polynucleotides e.g., encoding an immunoglobulin chain or component of the antibody display system of the present invention (e.g., a bait), may, in an embodiment of the invention, be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

Polynucleotides e.g., encoding an immunoglobulin chain or component of the antibody display system of the present invention, may be operably associated with a promoter. A "promoter" or "promoter sequence" is, in an embodiment of the invention, a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

The terms "vector", "cloning vector" and "expression vector" include a vehicle (e.g., a plasmid) by which a DNA or RNA sequence can be introduced into a host cell, so as to transform the host and, optionally, promote expression and/or replication of the introduced sequence. Polynucleotides encoding an immunoglobulin chain or component of the antibody display system of the present invention (e.g., a bait) may, in an embodiment of the invention, be in a vector.

A host cell that may be used in a composition or method of the present invention, as is discussed herein, includes eukaryotes such a lower and higher eukaryotic cells as well as prokaryotics. Higher eukaryote cells include mammalian, insect (e.g., *Spodoptera frugiperda* cells), and plant cells (e.g., *Protalix* cells). In an embodiment of the invention, the host cell is a lower eukaryote such as a yeast or filamentous fungi cell, which, for example, is selected from the group consisting of any *Pichia* cell, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia, Saccharomyces cerevisiae, Saccharomyces, Hansβnula polymorpha, Kluyveromyces, Kluyveromyces lactis, Candida albicans, Aspergillus nidulans, Aspergillus niger, Aspergillus oryzae, Trichoderma reesei, Chrysosporium lucknowense, Fusarium, Fusańum gramineum, Fusarium venenatum* and *Neuraspora crassa*. A higher eukaryotic host cell includes a mammalian host cell for example a Chinese hamster ovary (CHO) cell, a BHK cell, or an NSO cell. A prokaryotic host cell can be, for example, a bacterial cell such as *Escherichia, Enterobacter, Azotobacter, Erwinia, Bacillus, Pseudomonas, Klebsiella, Proteus, Salmonella, Serratia, Shigella, Rhizobia, Vitreoscilla,* and *Paracoccus*. *E. coli* host cells include DHB4, BL21 (which are deficient in both Lon (Phillips et al. (1984) J. Bacteriol. 159: 283) and OmpT proteases), HB101, BL21 DE3, *E. coli* AD494, *E. coli* W3110 (ATCC 27,325), *E. coli* 294 (ATCC 31,446), *E. coli* B, and *E. coli* X1776 (ATCC 31,537). Other strains include *E. coli* B834 which are methionine deficient (Leahy et al. (1992) Science 258, 987); other strains include the BLR strain, and the K-12 strains HMS174 and NovaBlue, which are recA-derivative that improve plasmid monomer yields and may help stabilize target plasmids containing repetitive sequences (these strains can be obtained from Novagen). See also U.S. Pat. Nos. 4,952,496, 5,693,489 and 5,869,320 and in Davanloo, P., et al., (1984) Proc. Natl. Acad. Sci. USA 81, 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259. Prokaryotic cells can also be cultured, for example, in a medium under conditions allowing for recombinant expression of a polypeptide, such as an immunoglobulin polypeptide and/or a bait. Such methods and host cells comprising such genes and proteins are part of the present invention. A prokaryotic host cell can also be used as a host cell in the antibody display system of the present invention, as discussed herein.

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. Predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)).

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core", often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms." "PNGase", or "glycanase" or "glucosidase" refer to peptide N-glycosidase F (EC 3.2.2.18).

In an embodiment of the invention, O-glycosylation of glycoproteins in a "eukaryotic host cell" is controlled. The scope of the present invention includes isolated eukaryotic host cells (e.g., *Pichia pastoris*) wherein O-glycosylation is controlled (as discussed herein) as well as antibody display systems comprising such eukaryotic host cells and methods of use thereof (as discussed herein). For example, wherein O-glycan occupancy and mannose chain length are reduced. In lower eukaryote host cells such as yeast, O-glycosylation can be controlled by deleting the genes encoding one or more protein O-mannosyltransferases (Dol-PMan: Protein (Ser/Thr) Mannosyl Transferase genes) (PMTs) or by growing the host in a medium containing one or more Pmtp inhibitors. Thus, the present invention includes isolated eukaryotic host cells, antibody display systems and methods of use thereof (as is discussed herein), e.g., comprising a deletion of one or more of the genes encoding PMTs, and/or, e.g., wherein the host cell can be cultivated in a medium that includes one or more Pmtp inhibitors. Pmtp inhibitors include but are not limited to a benzylidene thiazolidinedione. Examples of benzylidene thiazolidinediones are 5-[[3,4bis(phenylmethoxy) phenyl]methylene]-4-oxo-2-thioxo-3-thiazolidineacetic Acid; 5-[[3-(1-25 Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo3-thiazolidineacetic acid.

In an embodiment of the invention, a "eukaryotic host cell" includes a nucleic acid that encodes an alpha-1,2-mannosidase that has a signal peptide that directs it for secretion. For example, in an embodiment of the invention, the host cell is engineered to express an exogenous alpha-1,2-mannosidase enzyme having an optimal pH between 5.1 and 8.0, preferably between 5.9 and 7.5. In an embodiment of the invention, the exogenous enzyme is targeted to the endoplasmic reticulum or Golgi apparatus of the host cell, where it trims N-glycans such as $Man_8GlcNAc_2$ to yield $Man_5GlcNAc_2$. See U.S. Pat. No. 7,029,872.

The scope of the present invention includes such an isolated eukaryotic host cell (e.g., *Pichia pastoris*) as well as antibody display systems comprising such eukaryotic host cells and methods of use thereof (as discussed herein).

"Eukaryotic host cells" are, in an embodiment of the invention, lower eukaryote cells (e.g., yeast such as *Pichia pastoris*) that are genetically engineered to eliminate glycoproteins having alpha-mannosidase-resistant N-glycans by deleting or disrupting one or more of the beta-mannosyltransferasegenes (e.g., BMT1, BMT2, BMT3, and BMT4) (See, U.S. Published Patent Application No. 2006/0211085) or abrogating translation of RNAs encoding one or more of the beta-mannosyltransferasesusinginterfering RNA, anti-sense RNA, or the like. The scope of the present invention includes such an isolated eukaryotic host cell (e.g., *Pichia pastoris*) as well as antibody display systems comprising such eukaryotic host cells and methods of use thereof (as discussed herein).

"Eukaryotic host cells" also include lower eukaryote cells (e.g., yeast and filamentous fungi such as *Pichia pastoris*) that are genetically engineered to eliminate glycoproteins having phosphomannose residues, e.g., by deleting or disrupting one or both of the phosphomannosyl transferase genes PNO1 and MNN4B (See for example, U.S. Pat. Nos. 7,198,921 and 7,259,007), which can include deleting or disrupting the MNN4A gene or abrogating translation of RNAs encoding one or more of the phosphomannosyltransferases using interfering RNA, antisense RNA, or the like. In an embodiment of the invention, a "eukaryotic host cell" has been genetically modified to produce glycoproteins that have predominantly an N-glycan selected from the group consisting of complex N-glycans, hybrid N-glycans, and high mannose N-glycans wherein complex N-glycans are, in an embodiment of the invention, selected from the group consisting of $Man_3GlcNAc_2$, $GlcNAC_{(1-4)}Man_3GlcNAc_2$, $NANA_{(1-4)}GlcNAc_{(1-4)}Man_3GlcNAc_2$, and $NANA_{(1-4)}Gal_{(1-4)}Man_3GlcNAc_2$; hybrid N-glycans are, in an embodiment of the invention, selected from the group consisting of $Man_5GlcNAc_2$, $GlcNAcMan_5GlcNAc_2$, $GalGlcNAcMan_5GlcNAc_2$, and $NANAGalGlcNAcMan_5GlcNAc_2$; and high mannose N-glycans are, in an embodiment of the invention, selected from the group consisting of $Man_6GlcNAc_2$, $Man_7GlcNAc_2$, $Man_8GlcNAc_2$, and $Man_9GlcNAc_2$. The scope of the present invention includes such an isolated eukaryotic host cell (e.g., *Pichia pastoris*) as well as antibody display systems comprising such eukaryotic host cells and methods of use thereof (as discussed herein).

As used herein, the term "essentially free of" as it relates to lack of a particular sugar residue, such as fucose, or galactose or the like, on a glycoprotein, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent.

As used herein, a glycoprotein composition "lacks" or "is lacking" a particular sugar residue, such as fucose or galactose, when no detectable amount of such sugar residue is present on the N-glycan structures. For example, in preferred embodiments of the present invention, the glycoprotein compositions are produced by lower eukaryotic organisms, as discussed herein, and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

For example, a host cell which introduces, eliminates or modifies sugar residues on an immunoglobulin expressed in the host cell, e.g., as is discussed herein, may, in certain instances, be referred to herein as a "controlled glycosylation host cell."

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. During the cell sorting process, the cell suspension is entrained in the center of a narrow, rapidly flowing stream of liquid. The flow is arranged so that there is a separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately-prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off. The present invention encompasses methods of using the antibody display system of the present invention, e.g., as discussed herein, wherein the eukaryotic host cells that are bound to an antigen of interest (by the Fc/antigen-binding fragment) are sorted from unbound cells or cells without sufficient levels of binding, by FACS sorting, based on whether the cells are labeled with a detectable fluorescent label (e.g., wherein the antigen itself or a secondary antibody is labeled). Such sorted labeled host cells and compositions comprising such sorted labeled host cells are also part of the present invention.

A regulatable promoter is a promoter whose expression can be induced or inhibited. Embodiments of the invention include the antibody display system wherein expression of the bait is controlled by a regulatable promoter as well as methods of use thereof as discussed herein. Polynucleotides encoding the bait, operably associated with a regulatable promoter also form part of the present invention along with isolated eukaryotic host cells including the polynucleotides. Examples of regulatable promoters that occur in yeast include the GUT1 promoter, GADPH promoter and the PCK1 promoter.

In an embodiment of the invention, expression of a polynucleotide (e.g., the bait) in a eukaryotic host cell (e.g., a bait) is inhibited by exposing the cells to anti-sense RNA or by RNA interference (e.g., microRNA (miRNA) or small interfering RNA (siRNA)). Embodiments of the invention include methods of using antibody display system (e.g., as discussed herein) wherein expression of the bait is inhibited by RNA interference or anti-sense RNA. Isolated eukaryotic host cells of the present invention (e.g., as discussed herein) comprising bait and further comprising an anti-sense or RNA interference molecule that inhibits bait expression are part of the present invention.

Antibodies

Antibodies or antigen-binding fragments thereof identified in connection with use of the present invention (e.g., use of the antibody display system of the present invention) may be reformatted into any suitable form. For example, CDRs from a full antibody isolated using the antibody display system can be incorporated into a different framework (e.g., a human framework) to generate a distinct antibody or antigen-binding fragment comprising the CDRs isolated from the antibody display system of the present invention. Methods for producing chimeric, humanized and human antibodies are well known in the art. See, e.g., U.S. Pat. No. 5,530,101, issued to Queen et al., U.S. Pat. No. 5,225,539, issued to Winter et al., U.S. Pat. No. 4,816,397 issued to Boss et al. Such methods for reformatting an antibody or antigen-binding fragment or for relocating CDRs from one framework to another are conventional and well known in the art. For example, the CDRs of an antibody or antigen-binding fragment can be used to generate monoclonal antibodies, polyclonal antibodies, bispecific antibodies, chimeric antibodies, recombinant antibodies, anti-idiotypic antibodies, humanized antibodies and bispecific antibodies; or antigen-binding fragments thereof such as nanobodies, Fab, Fab', F(ab')$_2$, Fv fragments; dsFv; (dsFv)$_2$, ds diabodies; dsFv-dsFv'; single-chain antibody molecules, e.g., sc-Fv, sc-Fv dimers (bivalent diabodies); and bispecific diabodies.

A full antibody comprises a tetramer of subunits. Each tetramer has two identical pairs of polypeptide chains, each pair having one "light" chain (LC) (about 25 kDa) and one "heavy" chain (HC) (about 50-70 kDa). The amino-terminal portion of each chain includes a variable region of about 100 to 110 or more amino acids primarily responsible for antigen recognition. The carboxy-terminal portion of each chain defines a constant domain, in part, responsible for effector function. Light chains (LCs) are classified as either kappa or lambda based on the type of constant domain in the light chain. Heavy chains (HCs) are classified as gamma, mu, alpha, delta, or epsilon, based on the type of constant domain in the heavy chain, and define the antibody's isotype as IgG (e.g., IgG1, IgG2, IgG2a, IgG2b, IgG3 or IgG4), IgM, IgA (e.g., IgA1 or IgA2), IgD or IgE, respectively.

The present invention encompasses methods for making an antibody or antigen-binding fragment thereof comprising introducing, into an isolated host cell (e.g., a eukaryotic host cell such as Pichia, e.g., Pichia pastoris) comprising a bait that includes a human Fc immunoglobulin domain or functional fragment thereof (e.g., human; e.g., comprising a VH—CH1, CH2-CH3 or CH3 polypeptide) fused to a surface anchor polypeptide or functional fragment thereof, one or more polynucleotides encoding an immunoglobulin light chain variable region; and/or one or more polynucleotides encoding an immunoglobulin heavy chain variable region and culturing the host cell under condition whereby the polynucleotides encoding the immunoglobulin chains are expressed and an antibody or antigen-binding fragment thereof is formed from said chains.

In an embodiment of the invention, said bait is operably associated with a regulatable promoter and the bait expression is inhibited when said immunoglobulin chains are expressed. In an embodiment of the invention, bait expression is inhibited with anti-sense RNA or by RNA interference.

The present invention also provides a method for determining the quantity of an antibody or antigen-binding fragment thereof, e.g., by enzyme linked immunosorbent assay (ELISA). For example, in an embodiment of the invention, the method comprises culturing a eukaryotic host cell comprising an isolated polypeptide comprising a bait polypeptide (Fc immunoglobulin domain or functional fragment thereof (e.g., human; e.g., comprising a VH—CH1, CH2-CH3 or CH3 polypeptide) fused to a surface anchor polypeptide or functional fragment thereof); wherein the host cell secretes full antibody or antigen-binding fragment thereof (optionally, the antibody or fragment is isolated from the host cell and/or culture medium); and determining the quantity of the antibody or antigen-binding fragment thereof by ELISA. In an embodiment of the invention, expression of the bait is inhibited before quantitation such that the host cell expresses and secretes only full antibody. Bait polynucleotide can be operably associated with a regulatable promoter which is inhibited so as to inhibit bait expression. For example, in an embodiment of the invention, ELISA comprises coating the antigen on a solid substrate; binding the antibody or antigen-binding fragment thereof to the antigen; binding a detectably labeled secondary antibody to the antibody or fragment; and detecting the secondary antibody. In an embodiment of the invention, the secondary antibody is labeled with alkaline phosphatase or horse radish peroxidase. In an embodiment of the invention, the label is detected by binding the alkaline phosphatase (AP) or horse radish peroxidase (HRP) with substrate and measuring absorbance of the plate (e.g., HRP substrate 3,3',5,5'-tetramethylbenzidine (TMB); HRP substrate 3,3'-diaminobenzidine (DAB); or HRP substrate 2,2'-azino-bis(3-ethylbenzthiazoline-6-sulphonic acid) (ABTS); or AP substrate para-nitrophenylphosphate).

The present invention also provides a method for determining the affinity of an antibody or antigen-binding fragment thereof, that is secreted from a eukaryotic host cell in the antibody display system of the present invention, for an antigen. For example, the affinity can be determined by standard affinity ELISA, Biacore analysis or competition assays.

Antibody Display System

The present invention provides an antibody display system, composition or kit comprising (1) a eukaryotic host cell and (2) a bait comprising an Fc (e.g., a human Fc, e.g., comprising a VH—CH1, a CH3, or a CH2-CH3 polypeptide) fused, at the N- or C-terminus, (optionally, by a peptide linker such as GGG) to a surface anchor which bait is optionally linked to a signal sequence (e.g., an alpha mating factor signal sequence, e.g., from Saccharomyces cerevisiae); which system may be used, for example, in the identification of antibodies. Thus, in an embodiment of the invention, the host cell in the system expresses one or more immunoglobulin chains (e.g., light and heavy chains, e.g., wherein one or more of the chains are from a library source) of an antibody and/or of an Fc/antigen-binding fragment thereof. In an embodiment of the invention, the immunoglobulin chains of an antibody and/or of an Fc/antigen-binding fragment thereof comprises an identical or different CH2-CH3 polypeptide from that of the bait.

An Fc/antigen-binding fragment of an antibody (1) complexes with the Fc moiety of the bait (e.g., a human Fc, e.g., comprising a VH—CH1, CH3 or CH2-CH3 polypeptide) and (2) binds to an antigen when complexed with the bait on the surface of the host cell. An example of an Fc/antigen-binding fragment is a monovalent fragment of a full antibody (i.e., a monovalent antibody fragment). In an embodiment of the invention, the bait comprises a CH2-CH3 polypeptide or functional fragment thereof that differs at one or more residues from the CH2-CH3 of the Fc/antigen-binding fragment of an antibody. In such an embodiment of the invention, when the bait and the Fc/antigen-binding fragment of an antibody bind, a heterodimeric Fc domain is formed.

A "monovalent antibody fragment" comprises one half of an antibody, i.e., the antibody heavy chain (VH—CH1-CH2-CH3) bound to the antibody light chain (VL-CL) comprising three paired CDRs, e.g., wherein CH1 and CL are bound by a disulfide bridge, which monovalent antibody fragment is capable of detectably binding an antigen.

The "bait" comprises an Fc domain (e.g., human, rat, rabbit, goat or mouse Fc, e.g., any part of the heavy chain (e.g., human, rat, rabbit, goat or mouse) such as, for example, a CH3 polypeptide, a VH—CH1 polypeptide or a CH2-CH3 polypeptide) fused, e.g., at the amino-terminus or carboxy-terminus, to a surface anchor, which bait possesses functional properties described herein (e.g., as set forth below) that enable the bait to function in the antibody display system of the present invention. The Fc domain can, in an embodiment of the invention, be mutated so as to improve its ability to function in the antibody display system of the present invention, for example, cysteines or other residues may be added or moved to allow for more extensive disulfide bridges to form when complexed with a human IgG Fc or Fc/antigen-binding fragment. An Fc suitable for use in the bait comprises an Fc (i.e., comprising the CH1 and/or CH2 and/or CH3 domains) or functional fragment thereof (e.g., from an IgG1, IgG2, IgG3 or IgG4 or a mutant thereof) that is capable of dimerizing, when fused to a surface anchor protein, with, for example, a human IgG Fc or with the Fc/antigen-binding fragment on the surface of a eukaryotic host cell. In an embodiment of the invention, the term "Fc" refers to the "fragment crystallized" C-terminal region of an antibody containing the CH2 and CH3 domains. In an embodiment of the invention, dimerization between the bait Fc and the Fc/antigen-binding fragment occurs intracellularly, prior to routing to the cell surface, wherein the Fc and an Fc/antigen-binding fragment remain associated once at the cell surface. In general, in the absence of the Fc/antigen-binding fragment, the bait homodimerizes; thus comprising two surface anchors and two Fc domains. In an embodiment of the invention, a full antibody that is co-expressed with the bait comprises light and heavy chains capable of dimerizing with each other to form a monovalent antibody fragment, which monovalent antibody fragment dimerizes with the Fc of the bait.

An antigen can be any immunogenic molecule or substance, for example, a polypeptide (e.g., an oligopeptide), a cell membrane, cell extract or a whole cell. Polypeptide antigens include, for example, the following polypeptides: chemokines, cytokines (e.g., inflammatory cytokines or chemokines), receptors, PCSK9, granulocyte-CSF; coagulation factors such as factor VIII, factor IX, and human protein C; soluble IgE receptor alpha-chain; urokinase; chymase and urea trypsin inhibitor; IGF-binding protein; insulin-like growth factor-1 receptor, vascular epidermal growth factor, epidermal growth factor; growth hormone-releasing factor; GITR (glucocorticoid-induced TNFR-related protein), annexin V fusion protein; IL-23p19, IL-23p40, IL-23R, IL12R-beta 1, TNF alpha (tumor necrosis factor alpha), TGF beta (transforming growth factor beta), IL-10, IL-17, TSLP (Thymic stromal lymphopoietin), angiostatin; vascular endothelial growth factor-2; myeloid progenitor inhibitory factor-1; osteoprotegerin (OPG), RANK (receptor activator for nuclear factor kappa B) or RANKL (receptor activator for nuclear factor kappa B ligand); any of which can be, in an embodiment of the invention, human.

A "surface anchor" is any polypeptide that, when fused with an Fc or functional fragment thereof, is expressed and located to the cell surface where an Fc/antigen-binding fragment can complex with the Fc or functional fragment thereof. An example of a cell surface anchor is a protein such as, but not limited to, SED-1, α-agglutinin, Cwp1, Cwp2, GasI, Yap3, FIoIp1 Crh2, Pir1, Pir4, Tip1, Wpi, Hpwp1, Als3, and Rbt5; for example, *Saccharomyces cerevisiae* CWP1, CWP2, SED1, or GAS1; *Pichia pastoris* SP1 or GAS1; or *H. polymorpha* TIP1. In an embodiment of the invention, the surface anchor is any glycosylphosphatidylinositol-anchored (GPI) protein. A functional fragment of a surface anchor comprises a fragment of a full surface anchor polypeptide that is capable of forming a functional bait when fused to an Fc or functional fragment thereof; e.g., wherein the fragment, when expressed in a eukaryotic host cell as a Fc fusion, is located on the cell surface wherein the Fc is capable of forming a complex with an Fc/antigen-binding fragment (e.g., a monovalent antibody fragment).

As discussed herein, a suitable eukaryotic host cell for use in the antibody display system of the present invention is a *Pichia* cell such as *Pichia pastoris*.

The scope of the present invention encompasses an isolated eukaryotic host cell (e.g., *Pichia pastoris*) comprising a bait (i.e., comprising the human Fc domain or functional fragment thereof fused, e.g., at the amino-terminus or carboxy-terminus, to the surface anchor or functional fragment thereof) on the cell surface wherein the bait is dimerized with an Fc/antigen-binding fragment, e.g., by binding between the bait Fc and the heavy chain of a monovalent antibody fragment (e.g., between the CH2-CH3 polypeptides in the bait and the Fc/antigen-binding fragment). The present invention also includes a composition comprising a eukaryotic host cell comprising a bait and secreted antibody or antigen-binding fragment thereof and/or Fc/antigen-binding fragment thereof, e.g., in a liquid culture medium.

The present invention provides, for example, a method for identifying (i) an antibody or Fc/antigen-binding fragment thereof that binds specifically to an antigen of interest and/or (ii) a polynucleotide encoding an immunoglobulin heavy chain of said antibody or fragment and/or a polynucleotide encoding an immunoglobulin light chain of said antibody or fragment. The method comprises, in an embodiment of the invention:

(a) co-expressing a bait (e.g., comprising a polypeptide comprising a CH3, VH—CH1 or CH2-CH3 polypeptide that is linked to a cell surface anchor, such as SEDT) and one or more heavy and light immunoglobulin chains (e.g., wherein one or more of such chains are encoded by a polynucleotide from a library source) in an isolated eukaryotic host cell (e.g., *Pichia pastoris*) such that a complex between the Fc moiety of the bait (e.g., comprising a VH—CH1, CH3 or CH2-CH3 polypeptide) and an Fc/antigen-binding fragment (e.g., a monovalent antibody fragment) comprising the immunoglobulin chains forms, and is located at the cell surface; for example, wherein the host cell is transformed with one or more polynucleotides encoding the bait and the immunoglobulin chains;

(b) identifying a eukaryotic host cell expressing the bait, dimerized with the Fc/antigen-binding fragment of the antibody (e.g., a monovalent antibody fragment), which has detectable affinity (e.g., acceptable affinity) for the antigen (e.g., which detectably binds to the antigen); for example, wherein the bait, and light and heavy chain immunoglobulins are encoded by the polynucleotides in the eukaryotic host cell;

In an embodiment of the invention, non-tethered, secreted full antibodies comprising light and heavy chain immunoglobulin variable domains identical to those complexed with the bait (e.g., immunoglobulins that are expressed from the host cell) are analyzed to determine if they possess detectable affinity.

In an embodiment of the invention, the full antibodies are secreted from the host cell into the medium. In an embodiment of the invention, the full antibodies are isolated from the host cell.

In an embodiment of the invention, after step (b), expression of the bait in the host cell is inhibited, but expression of the full antibodies is not inhibited. In this embodiment of the invention, the host cell expresses only the full antibody but does not express the bait at any significant quantity. Once expression of the bait is inhibited, in an embodiment of the invention, the full antibody produced from the host cell is analyzed to determine if it possesses detectable affinity (e.g., acceptable affinity); and, (c) identifying said antibodies or antigen-binding fragments or polynucleotides if detectable binding of the Fc/antigen-binding fragment is observed, e.g., wherein one or more of the polynucleotides encoding the light and/or heavy chain immunoglobulin are optionally isolated from the host cell. In an embodiment of the invention, the nucleotide sequence of the polynucleotide is determined.

In an embodiment of the invention, a population of host cells express a common bait and a common immunoglobulin heavy chain as well a variety of different light chain immunoglobulins, e.g., from a library source, wherein individual light chain immunoglobulins that form Fc/antigen-binding fragments and full antibodies that are tethered to the bait and which exhibit antigen binding can be identified. Similarly, in an embodiment of the invention, a population of host cells express a common bait and a common immunoglobulin light chain as well a variety of different heavy chain immunoglobulins, e.g., from a library source, wherein individual heavy chain immunoglobulins that form Fc/antigen-binding fragments and full antibodies that are tethered to the bait and which exhibit antigen binding can be identified.

In an embodiment of the invention, the host cell possessing polynucleotides encoding the heavy and light chain immunoglobulins can be further used to express the secreted non-tethered antibody (e.g., full antibody) or an antigen-binding fragment thereof in culture. For example, in this embodiment of the invention, expression of the bait is optionally inhibited so that bait expression at significant quantities does not occur. The host cell is then cultured in a culture medium under conditions whereby secreted, non-tethered antibody (e.g., full antibody) or antigen-binding fragment thereof is expressed and secreted from the host cell. The non-tethered antibody or antigen-binding fragment thereof can optionally be isolated from the host cell and culture medium. In an embodiment of the invention, the immunoglobulin chains are transferred to a separate host cell (e.g., lacking the antibody display system components) for recombinant expression.

The present invention provides, for example, a method for identifying (i) an antibody or Fc/antigen-binding fragment thereof that binds specifically to an antigen of interest which comprises a second CH2-CH3 that differs from a first CH2-CH3 of a bait at one or more residues or (ii) a polynucleotide encoding an immunoglobulin heavy chain of said antibody or fragment and/or a polynucleotide encoding an immunoglobulin light chain of said antibody or fragment. The method comprises, in an embodiment of the invention:

(a) co-expressing a bait comprising a first CH2-CH3 polypeptide; along with a heavy immunoglobulin chain comprising said second CH2-CH3 polypeptide (e.g., wherein said heavy immunoglobulin chain is from a library source) and a light immunoglobulin chain (e.g., VL-CL), in an isolated eukaryotic host cell (e.g., *Pichia pastoris*) such that a complex between the first CH2-CH3 polypeptide of the bait and the second CH2-CH3 polypeptide of a Fc/antigen-binding fragment binds and is located at the cell surface; for example, wherein the host cell is transformed with one or more polynucleotides encoding the bait and the immunoglobulin chains;

(b) identifying a eukaryotic host cell expressing the bait, dimerized with the Fc/antigen-binding fragment which has detectable affinity (e.g., acceptable affinity) for the antigen; for example, wherein the bait, and light and heavy chain immunoglobulins are encoded by the polynucleotides in the eukaryotic host cell; and, optionally, (c) identifying said antibodies or antigen-binding fragments or polynucleotides if detectable binding of the Fc/antigen-binding fragment is observed, e.g., wherein one or more of the polynucleotides encoding the light and/or heavy chain immunoglobulin are optionally isolated from the host cell. In an embodiment of the invention, the nucleotide sequence of the polynucleotide is determined.

The antibody display system of the present invention may be use to evaluate the effects of a given glycosylation pattern on the affinity of an antibody or antigen-binding fragment thereof for an antigen. In general, the ability of the Fc/antigen-binding fragment comprising an altered glyosylation pattern may be evaluated for binding to the antigen, after which affinity of the full antibody or antigen-binding fragment thereof can be evaluated. Glycosylation patterns can be modified on the immunoglobulin chains expressed in the antibody display system, for example, by using a host cell, e.g., as is discussed herein, that modifies the glycosylation patterns when the chains are expressed and/or by culturing a host under conditions whereby the glycosylation pattern is modified, e.g., as discussed herein. For example, in an embodiment of the invention, the method comprise contacting an antibody display system with said antigen; wherein the antibody display system comprises: (a) an isolated eukaryotic controlled glycosylation host cell comprising a polynucleotide encoding an immunoglobulin light chain; and a polynucleotide encoding an immunoglobulin heavy chain; and (b) a bait comprising an Fc immunoglobulin domain or functional fragment thereof fused to a surface anchor polypeptide or functional fragment thereof on the surface of said eukaryotic host cell; wherein the Fc of said bait complexes with an Fc/antigen-binding fragment comprising said immunoglobulin heavy and immunoglobulin light chains on the surface of the host cell; wherein said heavy or light chain comprises said sugar; determining if said Fc/antigen-binding fragment specifically binds to said antigen; determining the binding affinity of the antibody or antigen-binding fragment thereof comprising said sugar for the antigen; and comparing the affinity of the antibody or antigen-binding fragment thereof with affinity of an otherwise identical antibody or antigen-binding fragment thereof which lacks said sugar; wherein the sugar is determined to increase affinity for the antigen if the affinity of the antibody or antigen-binding fragment thereof comprising said sugar is higher than the affinity of the antibody or antigen-binding fragment thereof which lacks the sugar, and/or wherein the sugar is determined to decrease affinity for the antigen if the affinity of antibody or antigen-binding fragment thereof comprising said sugar is lower than the affinity of the antibody or antigen-binding fragment thereof which lacks the sugar. For example, the affinity of the antibody or antigen-binding fragment thereof lacking the sugar can be determined in a similar manner in the antibody display system of the present invention or the affinity or it can be determined directly by measuring affinity by a known method such as ELISA, biacore assay or a competition assay.

Bait expression can be inhibited by any of several acceptable means. For example, the polynucleotides encoding the bait (e.g., the surface anchor and/or Fc) can be expressed by a regulatable promoter whose expression can be inhibited in the host cell. In an embodiment of the invention, bait expression is inhibited by RNA interference, anti-sense RNA, mutation or removal of the polynucleotide encoding the bait (e.g., surface anchor and/or Fc) from the host cell or genetic mutation of the polynucleotide so that the host cell does not express a functional bait.

"Acceptable affinity" refers to antibody or antigen-binding fragment affinity for the antigen which is at least $10^{-3}$ M or a greater affinity (lower number), e.g., $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M or $10^{-12}$ M.

In an embodiment of the present invention, polynucleotides encoding the antibody or Fc/antigen-binding fragment (e.g., monovalent antibody fragment) heavy and light chain are in one or more libraries of polynucleotides that encode light and/or heavy chain immunoglobulins (e.g., one library encoding light chains and one library encoding heavy chains). The particular immunoglobulin chains of interest are, in this embodiment, distinguished from the other chains in the library when the surface-anchored Fc/antigen-binding fragment on the host cell surface is observed to bind to an antigen of interest.

In an embodiment of the invention, the heavy or light chain immunoglobulin expressed in the antibody display system is from a library source and the other immunoglobulin chain is known (i.e., a single chain from a clonal source). In this embodiment of the invention, the antibody display system can be used, as discussed herein, to identify a new library chain that forms desirable antibodies or antigen-binding fragments thereof when coupled with the known chain. Alternatively, the antibody display system can be used to analyze expression and binding characteristics of an antibody or antigen-binding fragment thereof comprising two known immunoglobulin chains.

In an embodiment of the invention, cells expressing Fc/antigen-binding fragments tethered to the cell by an anchor such as SEDT that bind to an antigen can be detected by incubating the cells with fluorescently labeled antigen (e.g., biotin label) and sorting/selecting cells that specifically bind the antigen by fluorescence-activated cell sorting (FACS).

In an embodiment of the invention, the eukaryotic host cells expressing the bait dimerized with the Fc/antigen-binding fragment are identified and sorted using fluorescence-activated cell sorting (FACS). For example, in an embodiment of the invention, cells expressing the bait dimerized with the Fc/antigen-binding fragment on the cell surface are labeled with a fluorescent antigen or fluorescent secondary antibody that also binds to the antigen. The fluorescent label is detected during the FACS sorting and used as the signal for sorting. Labeled cells indicate the presence of a cell surface expressed bait/Fc/antigen-binding fragment/antigen complex and are collected in one vessel whereas cells not expressing signal are collected in a separate vessel. The present invention, accordingly, includes the a method comprising the following steps for determining if an antibody or antigen-binding fragment thereof from a library specifically binds to an antigen:

(1) Transform:
  (i) one or more immunoglobulin libraries, containing polynucleotides encoding light and heavy chain immunoglobulins;
  (ii) one or more immunoglobulin libraries, containing polynucleotides encoding light chain immunoglobulins and a single clonal heavy chain immunoglobulin; or
  (iii) one or more immunoglobulin libraries, containing polynucleotides encoding heavy chain immunoglobulins and a single clonal light chain immunoglobulin;
  wherein, said chains are capable of forming an antibody or antigen-binding fragment thereof, into a eukaryotic host cell comprising polynucleotides encoding the bait (e.g., *Pichia pastoris*);
(2) Grow transformed cells in a liquid culture medium;
(3) Allow expression of the bait on the surface of the cells;
(4) Label the cells with fluorescently labeled antigen or antigen bound to a fluorescently labeled secondary antibody;
(5) Sort and isolate fluorescently labeled cells using FACS for one round;
(6) Regrow the labeled, sorted cells;
(7) Allow expression of the bait in the cells;
(8) Label the cells with fluorescently labeled antigen or antigen bound to a fluorescently labeled secondary antibody;
(9) Sort and isolate fluorescently labeled cells using FACS for a second round;
(10) Regrow the labeled, sorted cells on solid culture medium so that individual cellular clones grow into discrete cellular colonies;
(11) Identify colonies with affinity for the antigen;
(12) Grow cells from identified colonies in a liquid culture medium and isolate supernatant containing full, non-tethered antibody or antigen-binding fragment thereof comprising the immunoglobulin light and heavy chains; wherein, expression of the bait is optionally inhibited;
(13) Determine affinity of non-tethered antibodies or antigen-binding fragments thereof, from the supernatant, for the antigen and identify clones with acceptable affinity (e.g., by Biacore analysis);
(14) Determine the nucleotide sequence of polynucleotides in the identified clones encoding the heavy and light chain immunoglobulins.

The scope of the present invention also includes a method for identifying polynucleotides encoding a heavy chain and light chain immunoglobulin of an antibody or for identifying an antibody which exhibits high stability. Such a method comprises the following steps:

(a) co-expressing the bait and the polynucleotides encoding the heavy and light chains in a eukaryotic host cell (e.g., *Pichia pastoris*) while subjecting antibodies comprising said chains to a denaturant;

In an embodiment of the invention, a denaturant is present in a concentration or amount or magnitude (e.g., at a sufficiently high temperature) that a practitioner of ordinary skill in the art would expect to, at least partially, denature an antibody and, thus, inhibit its ability to bind to an antigen. For example, possible denaturants include urea (e.g., 2, 3, 4, 5 or 6 M or more), detergent such as triton X-100 (e.g., 1% or more), dithiothreitol (DTT) (e.g., 250 mM or 500 mM or more), guanidine hydrochloride, light (e.g., ultraviolet or visible), extreme pH (e.g., 1, 2, 3, 14, 13 or 12) or a temperature above about 4° C., such as 37° C. (e.g., 42° C., 48° C. or 50° C.) or any combination thereof (e.g., 500 mM DTT/6 M urea).

(b) identifying a eukaryotic host cell expressing the bait, dimerized with the Fc/antigen-binding fragment (e.g., a monovalent antibody fragment), which fragment has detectable affinity (e.g., acceptable affinity) for the antigen;

In an embodiment of the invention, full antibodies comprising light and heavy chain variable regions identical to those complexed with the bait are also analyzed to determine if they possess detectable affinity.

In an embodiment of the invention, the full antibodies are secreted from the host cell. In an embodiment of the invention, the full antibodies are isolated from the host cell.

In an embodiment of the invention, expression of the bait in the host cell is inhibited, but expression of the full antibodies is not inhibited. In this embodiment of the invention, the host cell expresses only the full antibody but does not express the bait at any significant quantity. Once expression of the bait is inhibited, in an embodiment of the invention, the full antibody produced from the host cell is analyzed to determine if it possesses detectable affinity (e.g., acceptable affinity).

; and, (c) identifying said antibodies or polynucleotides encoding the heavy and light chains from the cell wherein one or more of the polynucleotides are optionally isolated from the host cell; wherein antibodies exhibiting affinity for the antigen in the presence of denaturant are determined to exhibit high stability. In an embodiment of the invention, the nucleotide sequence of the polynucleotide is determined.

In an embodiment of the invention, a human Fc immunoglobulin domain for use in a bait comprises the following amino acid sequence:

(SEQ ID NO: 1)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPG

In an embodiment of the invention, SED1 comprises the following amino acid sequence:

(SEQ ID NO: 2)
VDQFSNSTSASSTDVTSSSSISTSSGSVTITSSEAPESDNGTSTAAPTET

STEAPTTAIPTNGTSTEAPTTAIPTNGTSTEAPTDTTTEAPTTALPTNGT

STEAPTDTTTEAPTTGLPTNGTTSAFPPTTSLPPSNTTTTPPYNPSTDYT

TDYTVVTEYTTYCPEPTTFTTNGKTYTVTEPTTLTITDCPCTIEKPTTTS

-continued
TTEYTVVTEYTTYCPEPTTFTTNGKTYTVTEPTTLTITDCPCTIEKSEAP

ESSVPVTESKGTTTKETGVTTKQTTANPSLTVSTVVPVSSSASSHSVVIN

SNGANVVVPGALGLAGVAMLFL

In an embodiment of the invention, the human Fc immunoglobulin fused to the SED1 polypeptide is linked to a signal sequence such as an alpha mating factor signal sequence (e.g., MRFPSIFTAVLFAASSALA (SEQ ID NO: 3))

In an embodiment of the invention, the bait comprising the human Fc immunoglobulin domain fused to a SED1 polypeptide comprise the amino acid sequence:

(SEQ ID NO: 4)
MRFPSIFTAVLFAASSALADKTHTCPPCPAPELLGGPSVFLFPPKPKDTL

MISRTPEVICVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLICLVKGFYPSDIAVEWESNGQPENNYKTIPPVLDSD

GSFFLYSKLTVDKSRWQQGNVFSCSVMHEALHNHYTQKSLSLSPGGGGVD

QFSNSTSASSTDVISSSSISTSSGSVTITSSEAPESDNGTSTAAPTETST

EAPTTAIPTNGTSTEAPTTAIPTNGTSTEAPTDTTTEAPTTALPTNGTST

EAPTDTTTEAPTTGLPTNGTTSAFPPTTSLPPSNTTTTPPYNPSTDYTTD

YTVVTEYTTYCPEPTTFTTNGKTYTVTEPTTLTITDCPCTIEKPTTTSTT

EYTVVTEYTTYCPEPTTFTTNGKTYTVTEPTTLTITDCPCTIEKSEAPES

SVPVTESKGTTTKETGVTTKQTTANPSLTVSTVVPVSSSASSHSVVINSN

GANVVVPGALGLAGVAMLFL.

The Fc immunoglobulin domain is underscored and the linked is in bold face font. The SED1 polypeptide follows the linker and an alpha mating factor signal peptide is before the Fc.

EXAMPLES

The present invention is intended to exemplify the present invention and not to be a limitation thereof. The methods and compositions (e.g., polypeptides, polynucleotides, plasmids, yeast cells) disclosed below fall within the scope of the present invention.

Example 1: Construction and Use of Antibody Display System

Construction of Antibody Display Bait

Expression cassettes were constructed as follows. A polynucleotide encoding the N-terminus of a cell surface anchoring protein that inherently contains an attached glycophosphotidylinositol (GPI) post-translational modification that anchors the protein on the yeast cell wall was linked to a nucleic acid sequence that encodes the human IgG1 Fc region. The specific cell surface anchoring protein we used was *S. cerevisiae* Sed1 protein, which had been identified by screening a panel of cell wall of plasma membrane proteins that had been identified using GPI protein prediction software (described in international publication no. WO09/111183).

Figure 2:
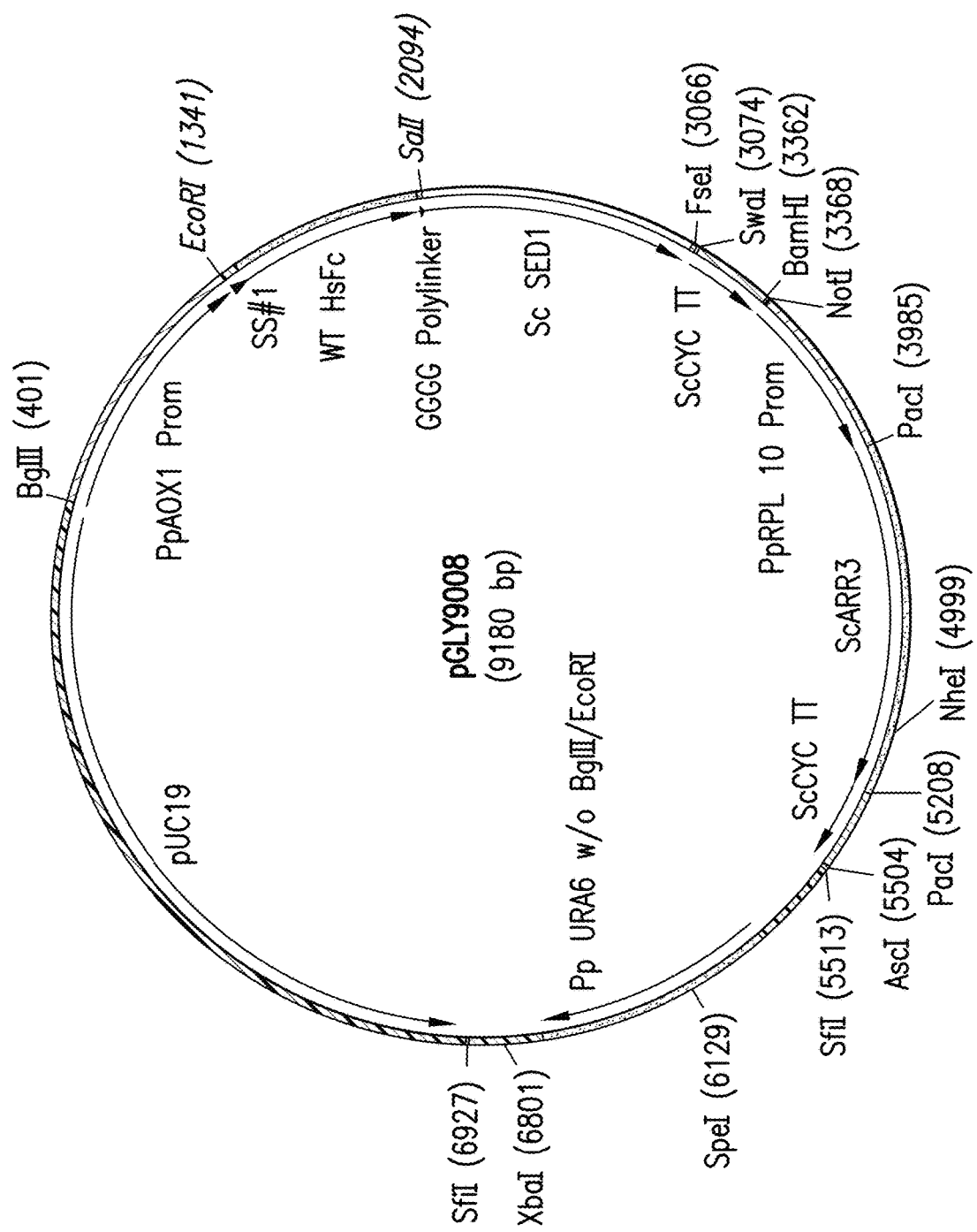
FIG. 2 shows a map of plasmid pGLY9008. The *Homo sapiens* Fc fused to *Saccharomyces cerevisiae* SED1 is driven by a *Pichia pastoris* AOX1 promoter.

To create the plasmid containing bait cassette, a codon optimized sequence of human IgG1 Fc fragment was synthesized using an EcoRI forward PCR primer containing the nucleic acid sequence of *S. cerevisiae* α-mating factor signal sequence fused upstream of the sequence encoding the IgG1 Fc N-terminus, and a SalI reverse primer encoding the C-terminus of IgG1 Fc that terminates in a sequence encoding a GGGG (SEQ ID NO: 7) linker. A plasmid containing the anti-Her2 gene sequence was used as a PCR template for amplification of an EcoRI-α-mating factor signal sequence-Fc-GGGG (SEQ ID NO: 7)-SalI fragment. Both PCR product and pGLY3033 (described in international publication no. WO09/111183) were digested using EcoRI and SalI endonucleases. The EcoRI-SalI fragment encoding the Fc was ligated in frame to EcoRI-SalI pGLY3033 backbone to generate plasmid pGLY9008 (FIG. 2). This plasmid enables delivery of the Fc-SEDT cassette under the control of the *Pichia pastoris* AOX1 promoter sequence. Like the parent plasmid it contains, the *Pichia pastoris* URA6 gene sequence, which serves as an integration locus in the genome, and the arsenite resistance gene, to allow selection on media containing sodium arsenite.

The pGLY3033 plasmid sequence comprises the nucleotide sequence:

```
                                                              (SEQ ID NO: 5)
TCGCGCGTTTCGGTGATGACGGTGAAAACCTCTGACACATGCAGCTCCCGGAGACGGTCACAGCTTGTCT

GTAAGCGGATGCCGGGAGCAGACAAGCCCGTCAGGGCGCGTCAGCGGGTGTTGGCGGGTGTCGGGGCTGG

CTTAACTATGCGGCATCAGAGCAGATTGTACTGAGAGTGCACCATATGCGGTGTGAAATACCGCACAGAT

GCGTAAGGAGAAAATACCGCATCAGGCGCCATTCGCCATTCAGGCTGCGCAACTGTTGGGAAGGGCGATC

GGTGCGGGCCTCTTCGCTATTACGCCAGCTGGCGAAAGGGGGATGTGCTGCAAGGCGATTAAGTTGGGTA

ACGCCAGGGTTTTCCCAGTCACGACGTTGTAAAACGACGGCCAGTGAATTGAGATCTAACATCCAAAGAC

GAAAGGTTGAATGAAACCTTTTTGCCATCCGACATCCACAGGTCCATTCTCACACATAAGTGCCAAACGC

AACAGGAGGGGATACACTAGCAGCAGACCGTTGCAAACGCAGGACCTCCACTCCTCTTCTCCTCAACACC

CACTTTTGCCATCGAAAAACCAGCCCAGTTATTGGGCTTGATTGGAGCTCGCTCATTCCAATTCCTTCTA

TTAGGCTACTAACACCATGACTTTATTAGCCTGTCTATCCTGGCCCCCCTGGCGAGGTTCATGTTTGTTT

ATTTCCGAATGCAACAAGCTCCGCATTACACCCGAACATCACTCCAGATGAGGGCTTTCTGAGTGTGGGG

TCAAATAGTTTCATGTTCCCCAAATGGCCCAAAACTGACAGTTTAAACGCTGTCTTGGAACCTAATATGA

CAAAAGCGTGATCTCATCCAAGATGAACTAAGTTTGGTTCGTTGAAATGCTAACGGCCAGTTGGTCAAAA

AGAAACTTCCAAAAGTCGGCATACCGTTTGTCTTGTTTGGTATTGATTGACGAATGCTCAAAAATAATCT

CATTAATGCTTAGCGCAGTCTCTCTATCGCTTCTGAACCCCGGTGCACCTGTGCCGAAACGCAAATGGGG

AAACACCCGCTTTTTGGATGATTATGCATTGTCTCCACATTGTATGCTTCCAAGATTCTGGTGGGAATAC

TGCTGATAGCCTAACGTTCATGATCAAAATTTAACTGTTCTAACCCCTACTTGACAGCAATATATAAACA

GAAGGAAGCTGCCCTGTCTTAAACCTTTTTTTTATCATCATTATTAGCTTACTTTCATAATTGCGACTG

GTTCCTATTGACTAGCTTTTGATTTTAACGACTTTTTACGACAACTTGAGAAGATCAAAAAACAACTAAT

TATTCGAAACGGAATTCacgatggtcgcttggtggtctttgtttctgtacggtcttcaggtcgctgcacc tgctttggctACTTCCAGATTGGAGGGATTGCAATCCGAAAACCACAGATTGAGAATGAAGATCACTGAG

TTGGACAAGGACTTGGAGGAAGTTACTATGCAGTTGCAGGATGTTGGTGGTTGTGAGCAGAAGTTGATCT

CCGAAGAGGATTTGGTCGACCAATTCTCTAACTCTACTTCCGCTTCCTCTACTGACGTTACTTCCTCCTC

CTCTATTTCTACTTCCTCCGGTTCCGTTACTATTACTTCCTCTGAGGCTCCAGAATCTGACAACGGTACT

TCTACTGCTGCTCCAACTGAAACTTCTACTGAGGCTCCTACTACTGCTATTCCAACTAACGGAACTTCCA

CAGAGGCTCCAACAACAGCTATCCCTACAAACGGTACATCCACTGAAGCTCCTACTGACACTACTACAGA

AGCTCCAACTACTGCTTTGCCTACTAATGGTACATCAACAGAGGCTCCTACAGATACAACAACTGAAGCT

CCAACAACTGGATTGCCAACAAACGGTACTACTTCTGCTTTCCCACCAACTACTTCCTTGCCACCATCCA

ACACTACTACTACTCCACCATACACCCCATCCACTGACTACACTACTGACTACACAGTTGTTACTGAGTA

CACTACTTACTGTCCAGAGCCAACTACTTTCACAACAAACGGAAAGACTTACACTGTTACTGAGCCTACT

ACTTTGACTATCACTGACTGTCCATGTACTATCGAGAAGCCAACTACTACTTCCACTACAGAGTATACTG

TTGTTACAGAATACACAACATATTGTCCTGAGCCAACAACATTCACTACTAATGGAAAAACATACACAGT

TACAGAACCAACTACATTGACAATTACAGATTGTCCTTGTACAATTGAGAAGTCCGAGGCTCCTGAATCT
```

-continued

```
TCTGTTCCAGTTACTGAATCCAAGGGTACTACTACTAAAGAAACTGGTGTTACTACTAAGCAGACTACTG
CTAACCCATCCTTGACTGTTTCCACTGTTGTTCCAGTTTCTTCCTCTGCTTCTTCCCACTCCGTTGTTAT
CAACTCCAACGGTGCTAACGTTGTTGTTCCTGGTGCTTTGGGATTGGCTGGTGTTGCTATGTTGTTCTTG
TTATAGGGCCGGCCATTTAAATACAGGCCCCTTTTCCTTTGTCGATATCATGTAATTAGTTATGTCACGC
TTACATTCACGCCCTCCTCCCACATCCGCTCTAACCGAAAAGGAAGGAGTTAGACAACCTGAAGTCTAGG
TCCCTATTTATTTTTTTAATAGTTATGTTAGTATTAAGAACGTTATTTATATTTCAAATTTTTCTTTTT
TTTCTGTACAAACGCGTGTACGCATGTAACATTATACTGAAAACCTTGCTTGAGAAGGTTTTGGGACGCT
CGAAGGCTTTAATTTGCAAGCTGGATCCGCGGCCGCTTACGCGCCGTTCTTCGCTTGGTCTTGTATCTCC
TTACACTGTATCTTCCCATTTGCGTTTAGGTGGTTATCAAAAACTAAAAGGAAAAATTTCAGATGTTTAT
CTCTAAGGTTTTTCTTTTTACAGTATAACACGTGATGCGTCACGTGGTACTAGATTACGTAAGTTATTT
TGGTCCGGTGGGTAAGTGGGTAAGTATAGAAAGCATGTAGGTTTACAAAAACGCAGTCACGAATTATTGC
TACTTCGAGCTTGGAACCACCCCAAAGATTATATTGTACTGATGCACTACCTTCTCGATTTTGCTCCTCC
AAGAACCTACGAAAACATTTCTTGAGCCTTTTCAACCTAGACTACACATCAAGTTATTTAAGGTATGTT
CCGTTAACATGTAAGAAAAGGAGAGGATAGATCGTTTATGGGGTACGTCGCCTGATTCAAGCGTGACCAT
TCGAAGAATAGGCCTTCGAAAGCTGAATAAAGCAAATGTCAGTTGCGATTGGTATGCTGACAAATTAGCA
TAAAAAGCAATAGACTTTCTAACCACCTGTTTTTTTCCTTTTACTTTATTTATATTTTGCCACCGTACTA
ACAAGTTCAGACAAATTAATTAACACCATGTCAGAAGATCAAAAAAGTGAAAATTCCGTACCTTCTAAGG
TTAATATGGTGAATCGCACCGATATACTGACTACGATCAAGTCATTGTCATGGCTTGACTTGATGTTGCC
ATTTACTATAATTCTCTCCATAATCATTGCAGTAATAATTTCTGTCTATGTGCCTTCTTCCCGTCACACT
TTTGACGCTGAAGGTCATCCCAATCTAATGGGAGTGTCCATTCCTTTGACTGTTGGTATGATTGTAATGA
TGATTCCCCCGATCTGCAAAGTTTCCTGGGAGTCTATTCACAAGTACTTCTACAGGAGCTATATAAGGAA
GCAACTAGCCCTCTCGTTATTTTTGAATTGGGTCATCGGTCCTTTGTTGATGACAGCATTGGCGTGGATG
GCGCTATTCGATTATAAGGAATACCGTCAAGGCATTATTATGATCGGAGTAGCTAGATGCATTGCCATGG
TGCTAATTTGGAATCAGATTGCTGGAGGAGACAATGATCTCTGCGTCGTGCTTGTTATTACAAACTCGCT
TTTACAGATGGTATTATATGCACCATTGCAGATATTTTACTGTTATGTTATTTCTCATGACCACCTGAAT
ACTTCAAATAGGGTATTATTCGAAGAGGTTGCAAAGTCTGTCGGAGTTTTTCTCGGCATACCACTGGGAA
TTGGCATTATCATACGTTTGGGAAGTCTTACCATAGCTGGTAAAAGTAATTATGAAAAATACATTTTGAG
ATTTATTTCTCCATGGGCAATGATCGGATTTCATTACACTTTATTTGTTATTTTTATTAGTAGAGGTTAT
CAATTTATCCACGAAATTGGTTCTGCAATATTGTGCTTTGTCCCATTGGTGCTTTACTTCTTTATTGCAT
GGTTTTTGACCTTCGCATTAATGAGGTACTTATCAATATCTAGGAGTGATACACAAAGAGAATGTAGCTG
TGACCAAGAACTACTTTTAAAGAGGGTCTGGGGAAGAAAGTCTTGTGAAGCTAGCTTTTCTATTACGATG
ACGCAATGTTTCACTATGGCTTCAAATAATTTTGAACTATCCCTGGCAATTGCTATTTCCTTATATGGTA
ACAATAGCAAGCAAGCAATAGCTGCAACATTTGGGCCGTTGCTAGAAGTTCCAATTTTATTGATTTTGGC
AATAGTCGCGAGAATCCTTAAACCATATTATATATGGAACAATAGAAATTAATTAACAGGCCCCTTTTCC
TTTGTCGATATCATGTAATTAGTTATGTCACGCTTACATTCACGCCCTCCTCCCACATCCGCTCTAACCG
AAAAGGAAGGAGTTAGACAACCTGAAGTCTAGGTCCCTATTTATTTTTTTAATAGTTATGTTAGTATTA
AGAACGTTATTTATATTTCAAATTTTTCTTTTTTTCTGTACAAACGCGTGTACGCATGTAACATTATAC
TGAAAACCTTGCTTGAGTAGGTTTTGGGACGCTCGTAGGCTTTTATTTGCAAGCTGCGGCCTAAGGCGCG
CCAGGCCATAATGGCCCAAATGCAAGAGGACATTAGAAATGTGTTTGGTAAGAACATGAAGCCGGAGGCA
TACAAACGATTCACAGATTTGAAGGAGGAAAACAAACTGCATCCACCGGAAGTGCCAGCAGCCGTGTATG
```

-continued

```
CCAACCTTGCTCTCAAAGGCATTCCTACGGATCTGAGTGGGAAATATCTGAGATTCACAGACCCACTATT
GGAACAGTACCAAACCTAGTTTGGCCGATCCATGATTATGTAATGCATATAGTTTTTGTCGATGCTCACC
CGTTTCGAGTCTGTCTCGTATCGTCTTACGTATAAGTTCAAGCATGTTTACCAGGTCTGTTAGAAACTCC
TTTGTGAGGGCAGGACCTATTCGTCTCGGTCCCGTTGTTTCTAAGAGACTGTACAGCCAAGCGCAGAATG
GTGGCATTAACCATAAGAGGATTCTGATCGGACTTGGTCTATTGGCTATTGGAACCACCCTTTACGGGAC
AACCAACCCTACCAAGACTCCTATTGCATTTGTGGAACCAGCCACGGAAAGAGCGTTTAAGGACGGAGAC
GTCTCTGTGATTTTTGTTCTCGGAGGTCCAGGAGCTGGAAAAGGTACCCAATGTGCCAAACTAGTGAGTA
ATTACGGATTTGTTCACCTGTCAGCTGGAGACTTGTTACGTGCAGAACAGAAGAGGGAGGGGTCTAAGTA
TGGAGAGATGATTTCCCAGTATATCAGAGATGGACTGATAGTACCTCAAGAGGTCACCATTGCGCTCTTG
GAGCAGGCCATGTAGGAAAACTTCGAGAAAGGGAAGACACGGTTCTTGATTGATGGATTCCCTCGTAAGA
TGGACCAGGCCAAAACTTTTGAGGAAAAAGTCGCAAAGTCCAAGGTGACACTTTTCTTTGATTGTCCCGA
ATCAGTGCTCCTTGAGAGATTACTTAAAAGAGGACAGACAAGCGGAAGAGAGGATGATAATGCGGAGAGT
ATCAAAAAAGATTCAAAACATTCGTGGTAACTTCGATGCCTGTGGTGGACTATTTCGGGAAGCAAGGAC
GCGTTTTGAAGGTATCTTGTGACCACCCTGTGGATCAAGTGTATTCACAGGTTGTGTCGGTGCTAAAAGA
GAAGGGGATCTTTGCCGATAACGAGACGGAGAATAAATAAACATTGTAATAAGATTTAGACTGTGAATGT
TCTATGTAATATTTTTCGAGATACTGTATCTATCTGGTGTACCGTATCACTCTGGACTTGCAAACTCATT
GATTACTTGTGCAATGGGCAAGAAGGATAGCTCTAGAAAGAAGAAGAAAAAGGAGCCGCCTGAAGAGCTG
GATCTTTCCGAGGTTGTTCCAACTTTTGGTTATGAGGAATTTCATGTTGAGCAAGAGGAGAATCCGGTCG
ATCAAGACGAACTTGACGGCCATAATGGCCTAGCTTGGCGTAATCATGGTCATAGCTGTTTCCTGTGTGA
AATTGTTATCCGCTCACAATTCCACACAACATACGAGCCGGAAGCATAAAGTGTAAAGCCTGGGGTGCCT
AATGAGTGAGCTAACTCACATTAATTGCGTTGCGCTCACTGCCCGCTTTCCAGTCGGGAAACCTGTCGTG
CCAGCTGCATTAATGAATCGGCCAACGCGCGGGGAGAGGCGGTTTGCGTATTGGGCGCTCTTCCGCTTCC
TCGCTCACTGACTCGCTGCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGGTATGTAGG
CGGTGCTACAGAGTTCTTGAAGTGGTGGCCTAACTACGGCTACACTAGAAGGACAGTATTTGGTATCTGC
GCTCTGCTGAAGCCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAAGAAGATCCTTT
GATCTTTTCTACGGGGTCTGACGCTCAGTGGAACGAAAACTCACGTTAAGGGATTTTGGTCATGAGATTA
TCAAAAAGGATCTTCACCTAGATCCTTTTAAATTAAAAATGAAGTTTTAAATCAATCTAAAGTATATATG
AGTAAACTTGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCAGCCG
GAAGGGCCGAGCGCAGAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGAGTTACATGATCCC
```

-continued

```
CCATGTTGTGCAAAAAAGCGGTTAGCTCCTTCGGTCCTCCGATCGTTGTCAGAAGTAAGTTGGCCGCAGT
GTTATCACTCATGGTTATGGCAGCACTGCATAATTCTCTTACTGTCATGCCATCCGTAAGATGCTTTTCT
GTGACTGGTGAGTACTCAACCAAGTCATTCTGAGAATAGTGTATGCGGCGACCGAGTTGCTCTTGCCCGG
CGTCAATACGGGATAATACCGCGCCACATAGCAGAACTTTAAAAGTGCTCATCATTGGAAAACGTTCTTC
GGGGCGAAAACTCTCAAGGATCTTACCGCTGTTGAGATCCAGTTCGATGTAACCCACTCGTGCACCCAAC
TGATCTTCAGCATCTTTTACTTTCACCAGCGTTTCTGGGTGAGCAAAAACAGGAAGGCAAATGCCGCAA
AAAAGGGAATAAGGGCGACACGGAAATGTTGAATACTCATACTCTTCCTTTTTCAATATTATTGAAGCAT
TTATCAGGGTTATTGTCTCATGAGCGGATACATATTTGAATGTATTTAGAAAAATAAACAAATAGGGGTT
CCGCGCACATTTCCCCGAAAAGTGCCACCTGACGTCTAAGAAACCATTATTATCATGACATTAACCTATA
AAAATAGGCGTATCACGAGGCCCTTTCGTC
```

The pGLY9008 plasmid sequence comprises the nucleotide sequence:

(SEQ ID NO: 6)
```
TCGCGCGTTTCGGTGATGACGGTGAAAACCTCTGACACATGCAGCTCCCGGAGACGGTCACAGCTTGTCT
GTAAGCGGATGCCGGGAGCAGACAAGCCCGTCAGGGCGCGTCAGCGGGTGTTGGCGGGTGTCGGGGCTGG
CTTAACTATGCGGCATCAGAGCAGATTGTACTGAGAGTGCACCATATGCGGTGTGAAATACCGCACAGAT
GCGTAAGGAGAAAATACCGCATCAGGCGCCATTCGCCATTCAGGCTGCGCAACTGTTGGGAAGGGCGATC
GGTGCGGGCCTCTTCGCTATTACGCCAGCTGGCGAAAGGGGGATGTGCTGCAAGGCGATTAAGTTGGGTA
ACGCCAGGGTTTTCCCAGTCACGACGTTGTAAAACGACGGCCAGTGAATTGAGATCTAACATCCAAAGAC
GAAAGGTTGAATGAAACCTTTTTGCCATCCGACATCCACAGGTCCATTCTCACACATAAGTGCCAAACGC
AACAGGAGGGGATACACTAGCAGCAGACCGTTGCAAACGCAGGACCTCCACTCCTCTTCTCCTCAACACC
CACTTTTGCCATCGAAAAACCAGCCCAGTTATTGGGCTTGATTGGAGCTCGCTCATTCCAATTCCTTCTA
TTAGGCTACTAACACCATGACTTTATTAGCCTGTCTATCCTGGCCCCCCTGGCGAGGTTCATGTTTGTTT
ATTTCCGAATGCAACAAGCTCCGCATTACACCCGAACATCACTCCAGATGAGGGCTTTCTGAGTGTGGGG
TCAAATAGTTTCATGTTCCCCAAATGGCCCAAAACTGACAGTTTAAACGCTGTCTTGGAACCTAATATGA
CAAAAGCGTGATCTCATCCAAGATGAACTAAGTTTGGTTCGTTGAAATGCTAACGGCCAGTTGGTCAAAA
AGAAACTTCCAAAAGTCGGCATACCGTTTGTCTTGTTTGGTATTGATTGACGAATGCTCAAAAATAATCT
CATTAATGCTTAGCGCAGTCTCTCTATCGCTTCTGAACCCCGGTGCACCTGTGCCGAAACGCAAATGGGG
AAACACCCGCTTTTTGGATGATTATGCATTGTCTCCACATTGTATGCTTCCAAGATTCTGGTGGGAATAC
TGCTGATAGCCTAACGTTCATGATCAAAATTTAACTGTTCTAACCCCTACTTGACAGCAATATATAAACA
GAAGGAAGCTGCCCTGTCTTAAACCTTTTTTTTATCATCATTATTAGCTTACTTTCATAATTGCGACTG
GTTCCTATTGACTAGCTTTTGATTTTAACGACTTTTAACGACAACTTGAGAAGATCAAAAAACAACTAAT
TATTCGAAACGGAATTCACGATGAGATTTCCTTCAATTTTTACTGCTGTTTTATTCGCAGCATCCTCCGC
ATTAGCTGACAAGACACATACTTGTCCACCATGTCCAGCTCCAGAATTGTTGGGTGGTCCATCCGTTTTC
TTGTTCCCACCAAAGCCAAAGGACACTTTGATGATCTCCAGAACTCCAGAGGTTACATGTGTTGTTGTTG
ACGTTTCTCACGAGGACCCAGAGGTTAAGTTCAACTGGTACGTTGACGGTGTTGAAGTTCACAACGCTAA
GACTAAGCCAAGAGAAGAGCAGTACAACTCCACTTACAGAGTTGTTTCCGTTTTGACTGTTTTGCACCAG
GACTGGTTGAACGGTAAAGAATACAAGTGTAAGGTTTCCAACAAGGCTTTGCCAGCTCCAATCGAAAGA
CTATCTCCAAGGCTAAGGGTCAACCAAGAGAGCCACAGGTTTACACTTTGCCACCATCCAGAGAAGAT
GACTAAGAACCAGGTTTCCTTGACTTGTTTGGTTAAAGGATTCTACCCATCCGACATTGCTGTTGAGTGG
```

-continued

```
GAATCTAACGGTCAACCAGAGAACAACTACAAGACTACTCCACCAGTTTTGGATTCTGATGGTTCCTTCT

TCTTGTACTCCAAGTTGACTGTTGACAAGTCCAGATGGCAACAGGGTAACGTTTTCTCCTGTTCCGTTAT

GCATGAGGCTTTGCACAACCACTACACTCAAAAGTCCTTGTCTTTGTCCCCTGGTGGTGGTGTCGAC

CAATTCTCTAACTCTACTTCCGCTTCCTCTACTGACGTTACTTCCTCCTCCTCTATTTCTACTTCCTCCG

GTTCCGTTACTATTACTTCCTCTGAGGCTCCAGAATCTGACAACGGTACTTCTACTGCTGCTCCAACTGA

AACTTCTACTGAGGCTCCTACTACTGCTATTCCAACTAACGGAACTTCCACAGAGGCTCCAACAACAGCT

ATCCCTACAAACGGTACATCCACTGAAGCTCCTACTGACACTACTACAGAAGCTCCAACTACTGCTTTGC

CTACTAATGGTACATCAACAGAGGCTCCTACAGATACAACAACTGAAGCTCCAACAACTGGATTGCCAAC

AAACGGTACTACTTCTGCTTTCCCACCAACTACTTCCTTGCCACCATCCAACACTACTACTACTCCACCA

TACAACCCATCCACTGACTACACTACTGACTACACAGTTGTTACTGAGTACACTACTTACTGTCCAGAGC

CAACTACTTTCACAACAAACGGAAAGACTTACACTGTTACTGAGCCTACTACTTTGACTATCACTGACTG

TCCATGTACTATCGAGAAGCCAACTACTACTTCCACTACAGAGTATACTGTTGTTACAGAATACACAACA

TATTGTCCTGAGCCAACAACATTCACTACTAATGGAAAAACATACACAGTTACAGAACCAACTACATTGA

CAATTACAGATTGTCCTTGTACAATTGAGAAGTCCGAGGCTCCTGAATCTTCTGTTCCAGTTACTGAATC

CAAGGGTACTACTACTAAAGAAACTGGTGTTACTACTAAGCAGACTACTGCTAACCCATCCTTGACTGTT

TCCACTGTTGTTCCAGTTTCTTCCTCTGCTTCTTCCCACTCCGTTGTTATCAACTCCAACGGTGCTAACG

TTGTTGTTCCTGGTGCTTTGGGATTGGCTGGTGTTGCTATGTTGTTCTTGTAATAGGGCCGGCCATTTAA

ATACAGGCCCCTTTTCCTTTGTCGATATCATGTAATTAGTTATGTCACGCTTACATTCACGCCCTCCTCC

CACATCCGCTCTTACCGAAAAGGAAGGAGTTAGACAACCTGAAGTCTAGGTCCCTATTTATTTTTTTAA

TAGTTATGTTAGTATTAAGTACGTTATTTATATTTCAAATTTTTCTTTTTTTTCTGTACAAACGCGTGTA

CGCATGTAACATTATACTGAAAACCTTGCTTGAGAAGGTTTTGGGACGCTCGAAGGCTTTAATTTGCAAG

CTGGATCCGCGGCCGCTTACGCGCCGTTCTTCGCTTGGTCTTGTATCTCCTTACACTGTATCTTCCCATT

TGCGTTTAGGTGGTTATCAAAAACTAAAAGGAAAAATTTCAGATGTTTATCTCTAAGGTTTTTTCTTTTT

ACAGTATAACACGTGATGCGTCACGTGGTACTAGATTACGTAAGTTATTTTGGTCCGGTGGGTAAGTGGG

TAAGTATAGAAAGCATGTAGGTTTACAAAAACGCAGTCACGAATTATTGCTACTTCGAGCTTGGAACCAC

CCCAAAGATTATATTGTACTGATGCACTACCTTCTCGATTTTGCTCCTCCAAGTACCTACGAAAAACATT

TCTTGAGCCTTTTCAACCTAGACTACACATCTAGTTATTTTAGGTATGTTCCGTTTACATGTAAGAAAAG

GAGAGGATAGATCGTTTATGGGGTACGTCGCCTGATTCAAGCGTGACCATTCGAAGAATAGGCCTTCGAA

AGCTGTATAAAGCAAATGTCAGTTGCGATTGGTATGCTGACAAATTAGCATAAAAAGCAATAGACTTTCT

AACCACCTGTTTTTTTCCTTTTACTTTATTTATATTTTGCCACCGTACTAACAAGTTCAGACAAATTAAT

TAACACCATGTCAGAAGATCAAAAAAGTGAAAATTCCGTACCTTCTAAGGTTAATATGGTGAATCGCACC

GATATACTGACTACGATCAAGTCATTGTCATGGCTTGACTTGATGTTGCCATTTACTATAATTCTCTCCA

TAATCATTGCAGTAATAATTTCTGTCTATGTGCCTTCTTCCCGTCACACTTTTGACGCTGAAGGTCATCC

CAATCTAATGGGAGTGTCCATTCCTTTGACTGTTGGTATGATTGTAATGATGATTCCCCCGATCTGCAAA

GTTTCCTGGGAGTCTATTCACAAGTACTTCTACAGGAGCTATATAAGGAAGCAACTAGCCCTCTCGTTAT

TTTTGAATTGGGTCATCGGTCCTTTGTTGATGACAGCATTGGCGTGGATGGCGCTATTCGATTATAAGGA

ATACCGTCAAGGCATTATTATGATCGGAGTAGCTAGATGCATTGCCATGGTGCTAATTTGGAATCAGATT

GCTGGAGGAGACAATGATCTCTGCGTCGTGCTTGTTATTACAAACTCGCTTTTACAGATGGTATTATATG

CACCATTGCAGATATTTTACTGTTATGTTATTTCTCATGACCACCTGAATACTTCAAATAGGGTATTATT

CGAAGAGGTTGCAAAGTCTGTCGGAGTTTTTCTCGGCATACCACTGGGAATTGGCATTATCATACGTTTG
```

-continued

```
GGAAGTCTTACCATAGCTGGTAAAAGTAATTATGAAAAATACATTTTGAGATTTATTTCTCCATGGGCAA
TGATCGGATTTCATTACACTTTATTTGTTATTTTTATTAGTAGAGGTTATCAATTTATCCACGAAATTGG
TTCTGCAATATTGTGCTTTGTCCCATTGGTGCTTTACTTCTTTATTGCATGGTTTTTGACCTTCGCATTA
ATGAGGTACTTATCAATATCTAGGAGTGATACACAAAGAGAATGTAGCTGTGACCAAGAACTACTTTTAA
AGAGGGTCTGGGGAAGAAAGTCTTGTGAAGCTAGCTTTTCTATTACGATGACGCAATGTTTCACTATGGC
TTCAAATAATTTTGAACTATCCCTGGCAATTGCTATTTCCTTATATGGTAACAATAGCAAGCAAGCAATA
GCTGCAACATTTGGGCCGTTGCTAGAAGTTCCAATTTTATTGATTTTGGCAATAGTCGCGAGAATCCTTA
AACCATATTATATATGGAACAATAGAAATTAATTAACAGGCCCCTTTTCCTTTGTCGATATCATGTAATT
AGTTATGTCACGCTTACATTCACGCCCTCCTCCCACATCCGCTCTAACCGAAAAGGAAGGAGTTAGACAA
CCTGAAGTCTAGGTCCCTATTTATTTTTTTAATAGTTATGTTAGTATTAAGAACGTTATTTATATTTCA
TATTTTTCTTTTTTTCTGTACAAACGCGTGTACGCATGTAACATTATACTGAAAACCTTGCTTGAGAAG
GTTTTGGGACGCTCGAAGGCTTTAATTTGCAAGCTGCGGCCTAAGGCGCGCCAGGCCATAATGGCCCAAA
TGCAAGAGGACATTAGAAATGTGTTTGGTAAGAACATGAAGCCGGAGGCATACAAACGATTCACAGATTT
GTAGGAGGAAAACAAACTGCATCCACCGGAAGTGCCAGCAGCCGTGTATGCCAACCTTGCTCTCAAAGGC
ATTCCTACGGATCTGAGTGGGAAATATCTGAGATTCACAGACCCACTATTGGAACAGTACCAAACCTAGT
TTGGCCGATCCATGATTATGTAATGCATATAGTTTTTGTCGATGCTCACCCGTTTCGAGTCTGTCTCGTA
TCGTCTTACGTATAAGTTCAAGCATGTTTACCAGGTCTGTTAGAAACTCCTTTGTGAGGGCAGGACCTAT
TCGTCTCGGTCCCGTTGTTTCTAAGAGACTGTACAGCCAAGCGCAGAATGGTGGCATTAACCATAAGAGG
ATTCTGATCGGACTTGGTCTATTGGCTATTGGAACCACCCTTTACGGGACAACCAACCCTACCAAGACTC
CTATTGCATTTGTGGAACCAGCCACGGAAAGAGCGTTTAAGGACGGAGACGTCTCTGTGATTTTTGTTCT
CGGAGGTCCAGGAGCTGGAAAAGGTACCCAATGTGCCAAACTAGTGAGTAATTACGGATTTGTTCACCTG
TCAGCTGGAGACTTGTTACGTGCAGAACAGAAGAGGGAGGGGTCTAAGTATGGAGAGATGATTTCCCAGT
ATATCAGAGATGGACTGATAGTACCTCAAGAGGTCACCATTGCGCTCTTGGAGCAGGCCATGAAGGAAAA
CTTCGAGAAAGGGAAGACACGGTTCTTGATTGATGGATTCCCTCGTAAGATGGACCAGGCCAAAACTTTT
GAGGAAAAAGTCGCAAAGTCCAAGGTGACACTTTTCTTTGATTGTCCCGAATCAGTGCTCCTTGAGAGAT
TACTTAAAAGAGGACAGACAAGCGGAAGAGAGGATGATAATGCGGAGAGTATCAAAAAAAGATTCAAAAC
ATTCGTGGAAACTTCGATGCCTGTGGTGGACTATTTCGGGAAGCAAGGACGCGTTTTGAAGGTATCTTGT
GACCACCCTGTGGATCAAGTGTATTCACAGGTTGTGTCGGTGCTAAAAGAGAAGGGGATCTTTGCCGATA
ACGAGACGGAGAATAAATAAACATTGTAATAAGATTTAGACTGTGAATGTTCTATGTAATATTTTTCGAG
ATACTGTATCTATCTGGTGTACCGTATCACTCTGGACTTGCAAACTCATTGATTACTTGTGCAATGGGCA
AGAAGGATAGCTCTAGAAAGAAGTAGAAAAAGGAGCCGCCTGAAGAGCTGGATCTTTCCGAGGTTGTTCC
AACTTTTGGTTATGAGGAATTTCATGTTGAGCAAGAGGAGAATCCGGTCGATCAAGACGAACTTGACGGC
CATAATGGCCTAGCTTGGCGTAATCATGGTCATAGCTGTTTCCTGTGTGAAATTGTTATCCGCTCACAAT
TCCACACAACATACGAGCCGGAAGCATAAAGTGTAAAGCCTGGGGTGCCTAATGAGTGAGCTAACTCACA
TTAATTGCGTTGCGCTCACTGCCCGCTTTCCAGTCGGGAAACCTGTCGTGCCAGCTGCATTAATGAATCG
GCCAACGCGCGGGGAGAGGCGGTTTGCGTATTGGGCGCTCTTCCGCTTCCTCGCTCACTGACTCGCTGCG
CTCGGTCGTTCGGCTGCGGCGAGCGGTATCAGCTCACTCAAAGGCGGTAATACGGTTATCCACAGAATCA
GGGGATAACGCAGGAAAGAACATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAGCGTGGCGCTTTCTCATAGCT
```

-continued

```
CACGCTGTAGGTATCTCAGTTCGGTGTAGGTCGTTCGCTCCAAGCTGGGCTGTGTGCACGAACCCCCGT

TCAGCCCGACCGCTGCGCCTTATCCGGTAACTATCGTCTTGAGTCCAACCCGGTAAGACACGACTTATCG

CCACTGGCAGCAGCCACTGGTAACAGGATTAGCAGAGCGAGGTATGTAGGCGGTGCTACAGAGTTCTTGA

AGTGGTGGCCTAACTACGGCTACACTAGAAGGACAGTATTTGGTATCTGCGCTCTGCTGAAGCCAGTTAC

CTTCGGAAAAAGAGTTGGTAGCTCTTGATCCGGCAAACAAACCACCGCTGGTAGCGGTGGTTTTTTTGTT

TGCAAGCAGCAGATTACGCGCAGAAAAAAAGGATCTCAAGAAGATCCTTTGATCTTTTCTACGGGGTCTG

ACGCTCAGTGGAACGAAAACTCACGTTAAGGGATTTTGGTCATGAGATTATCAAAAAGGATCTTCACCTA

GATCCTTTTAAATTAAAAATGAAGTTTTAAATCAATCTAAAGTATATATGAGTAAACTTGGTCTGACAGT

TACCAATGCTTAATCAGTGAGGCACCTATCTCAGCGATCTGTCTATTTCGTTCATCCATAGTTGCCTGAC

TCCCCGTCGTGTAGATAACTACGATACGGGAGGGCTTACCATCTGGCCCCAGTGCTGCAATGATACCGCG

AGACCCACGCTCACCGGCTCCAGATTTATCAGCAATAAACCAGCCAGCCGGAAGGGCCGAGCGCAGAAGT

GGTCCTGCAACTTTATCCGCCTCCATCCAGTCTATTAATTGTTGCCGGGAAGCTAGAGTAAGTAGTTCGC

CAGTTAATAGTTTGCGCAACGTTGTTGCCATTGCTACAGGCATCGTGGTGTCACGCTCGTCGTTTGGTAT

GGCTTCATTCAGCTCCGGTTCCCAACGATCAAGGCGAGTTACATGATCCCCCATGTTGTGCAAAAAAGCG

GTTAGCTCCTTCGGTCCTCCGATCGTTGTCAGAAGTAAGTTGGCCGCAGTGTTATCACTCATGGTTATGG

CAGCACTGCATAATTCTCTTACTGTCATGCCATCCGTAAGATGCTTTTCTGTGACTGGTGAGTACTCAAC

CAAGTCATTCTGAGAATAGTGTATGCGGCGACCGAGTTGCTCTTGCCCGGCGTCAATACGGGATAATACC

GCGCCACATAGCAGAACTTTAAAAGTGCTCATCATTGGAAAACGTTCTTCGGGGCGAAAACTCTCAAGGA

TCTTACCGCTGTTGAGATCCAGTTCGATGTAACCCACTCGTGCACCCAACTGATCTTCAGCATCTTTTAC

TTTCACCAGCGTTTCTGGGTGAGCAAAAACAGGAAGGCAAAATGCCGCAAAAAAGGGAATAAGGGCGACA

CGGAAATGTTGAATACTCATACTCTTCCTTTTTCAATATTATTGAAGCATTTATCAGGGTTATTGTCTCA

TGAGCGGATACATATTTGAATGTATTTAGAAAAATAAACAAATAGGGGTTCCGCGCACATTTCCCCGAAA

AGTGCCACCTGACGTCTAAGAAACCATTATTATCATGACATTAACCTATAAAAATAGGCGTATCACGAGG

CCCTTTCGTC
```

To test the capacity of this configuration for displaying monovalent antibody fragments (comprising human IgGs) (1 heavy chain immunoglobulin and 1 light chain immunoglobulin (H+L)) on the yeast cell wall, pGLY9008 was introduced into GFI 5.0 strains that have been selected previously as expression hosts of human anti-Her2 or anti-PCSK9 IgGs. An empty strain was included as a control (Table 1).

TABLE 1

Yeast Strains

| Strain | mAb |
| --- | --- |
| YGLY8316 | Empty |
| YGLY18483 | Anti-PCSK9 (AX189) |
| YGLY18281 | Anti-PCSK9 (AX132) |
| YGLY14755 | Anti-PCSK9 (1DG) |
| YGLY13979 | Anti-Her2 |
| YGLY14836 | Anti-Her2 |

*These Pichia pastoris strains form part of the present invention

The glycoengineered Pichia pastoris monoclonal antibody production strains in Table 1 were grown in 50 mL BMGY media until the culture optical density, at 600 nm, was 2. The cells were washed three times with 1 M sorbitol and resuspended in 1 mL 1 M sorbitol. About 1-2 micrograms of SpeI linearized pGLY9008 was mixed with these competent cells. Transformation was performed with a Bio-Rad electroporation apparatus using the manufacturer's program specific for electroporation of nucleic acids into Pichia pastoris. One mL recovery media was added to the cells, which were then plated out on yeast-soytone-dextrose (YSD) media with 50 µg/mL arsenite.

Growth and Induction of Fc-Monovalent Antibody Fragment (H+L) Displaying Yeast.

Figure 3A:
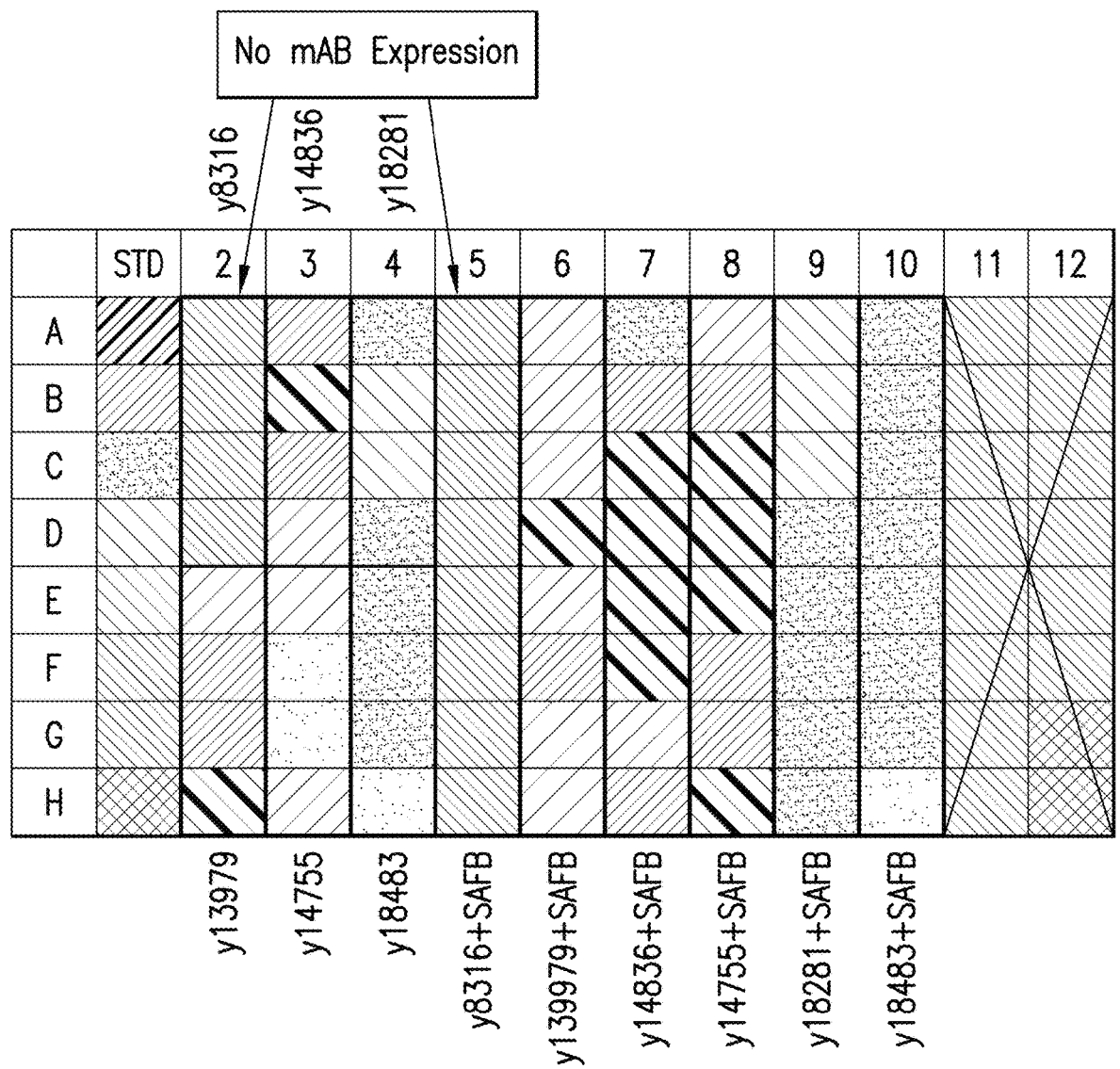
FIGS. 3A-3C.
Figure 3B:
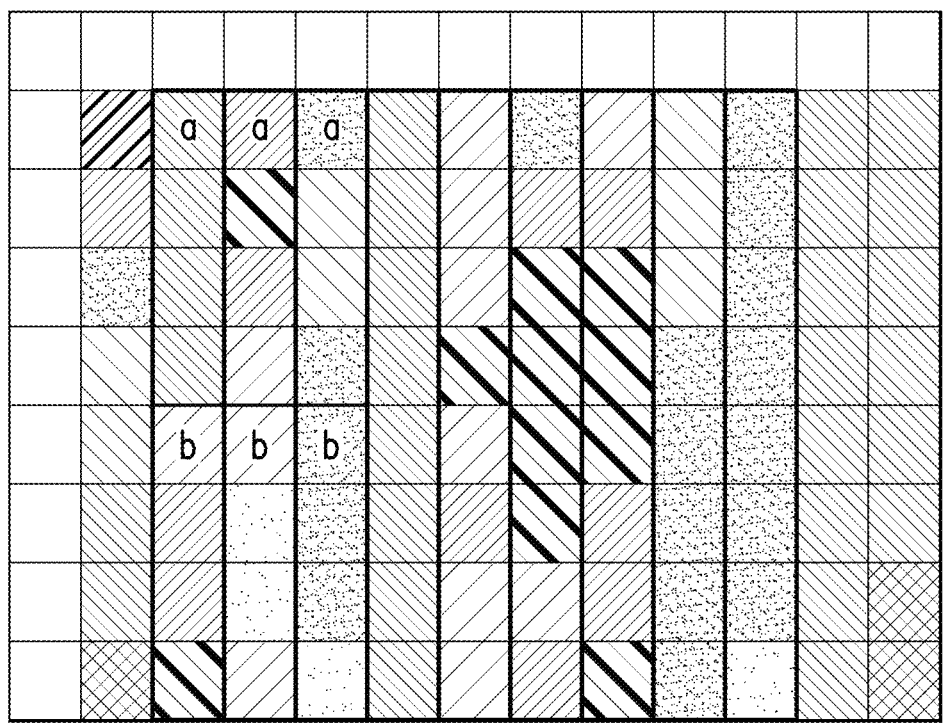
Figure 3C:
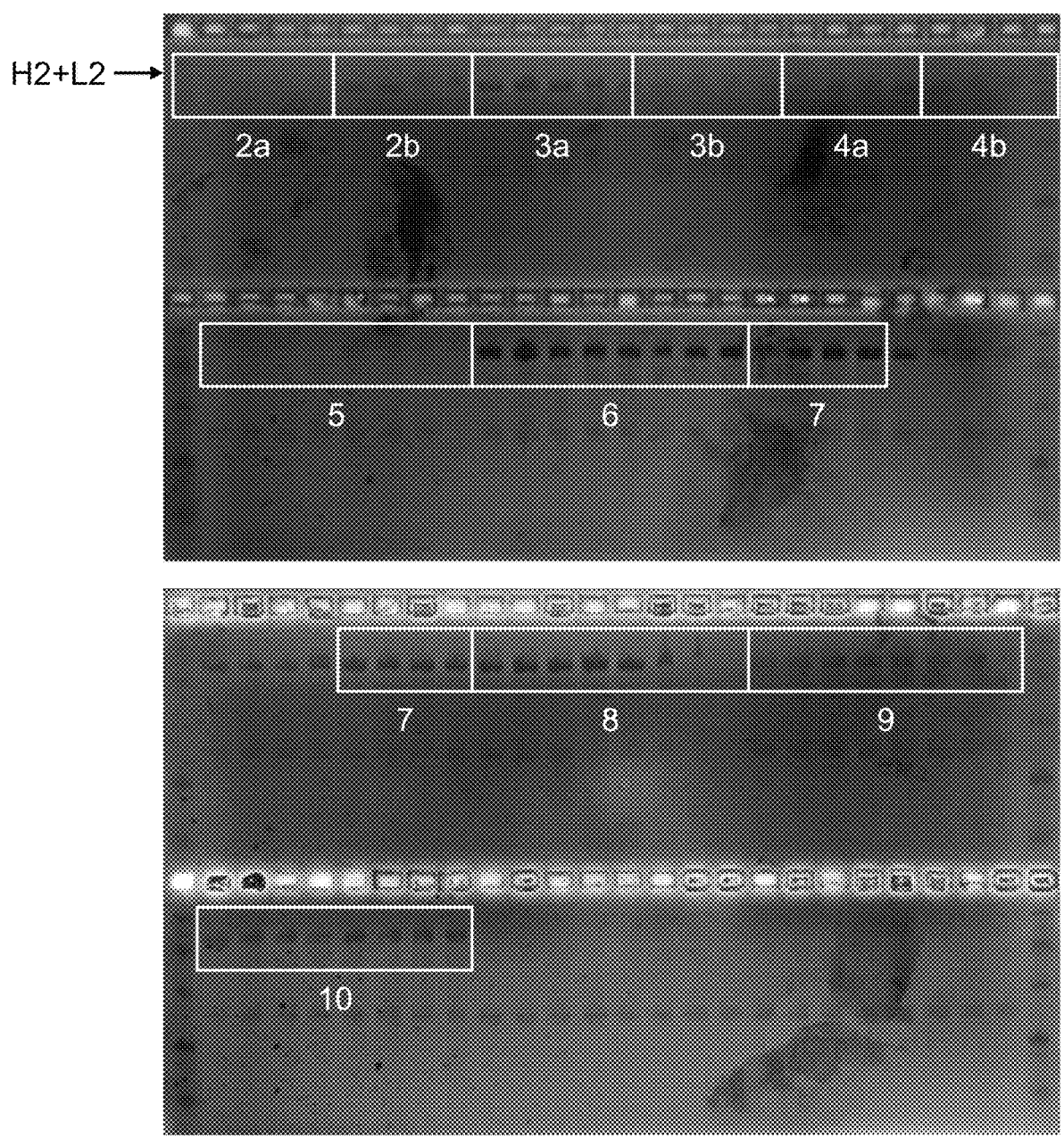

Glycoengineered yeast expressing human IgGs and the Fc-SEDT bait expression cassette were inoculated using 600 µL BMGY in a 96 deep well plate or 50 mL BMGY in a 250 mL shake flasks for two days. The cells were collected by centrifugation and the supernatant was discarded. The cells were induced by incubation in 300 µL or 25 mL BMMY with PMTi inhibitor overnight following the methods described in international application publication no. WO2007/061631. Following induction, culture supernatants were assayed for antibody expression using Kappa ELISA, according to the manufacturer's protocol, and Protein A capture SDS-PAGE analysis. The data in FIGS. 3A-3C, respectively, describe the results of both of these assays. As outlined in the figures, supernatants of cultures containing the Fc-Sed1 protein bait were found to contain similar levels of secreted full antibody molecules (2 heavy chain immunoglobulins and 2 light chain immunoglobulins ((H2+L2)) compared to their parent strains (containing no Fc-Sed1p).

This indicated that the presence of the Fc-Sed1p bait did not interfere with the yeast ability to secret full IgG antibodies (H2+L2).

To determine the efficiency of surface displaying antibodies using this method, cells were labeled with APC 635 labeled mouse anti-Human Kappa, which detects the light chain of human antibody molecules, and were processed by flow cytometry. Briefly, each culture, after growth to an optical density, at 600 nm, of 2, was pelleted by centrifugation and washed in 100 µL PBS. Cells were incubated for 30 minutes at room temperature (RT) in 100 µL phosphate buffer saline (PBS) containing fluorescently labeled (APC635) mouse anti-human Kappa light chain and washed in 100 µl PBS. One hundred microliters of PBS was used to resuspend pellets before analyzing in a flow cytometer.

Figure 4A:
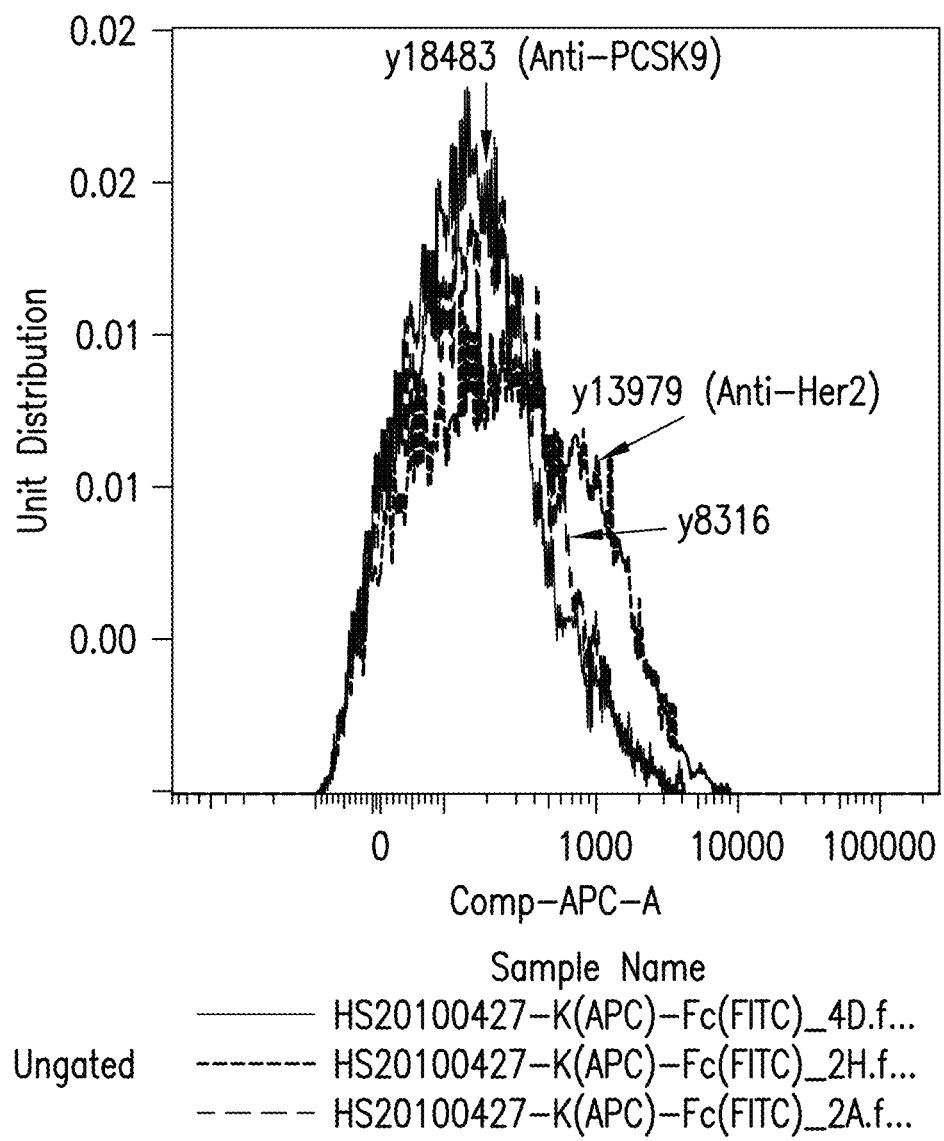
FIGS. 4A-4C show FACS data demonstrating the different fluorescence intensities observed between various *Pichia pastoris* strains.
Figure 4B:
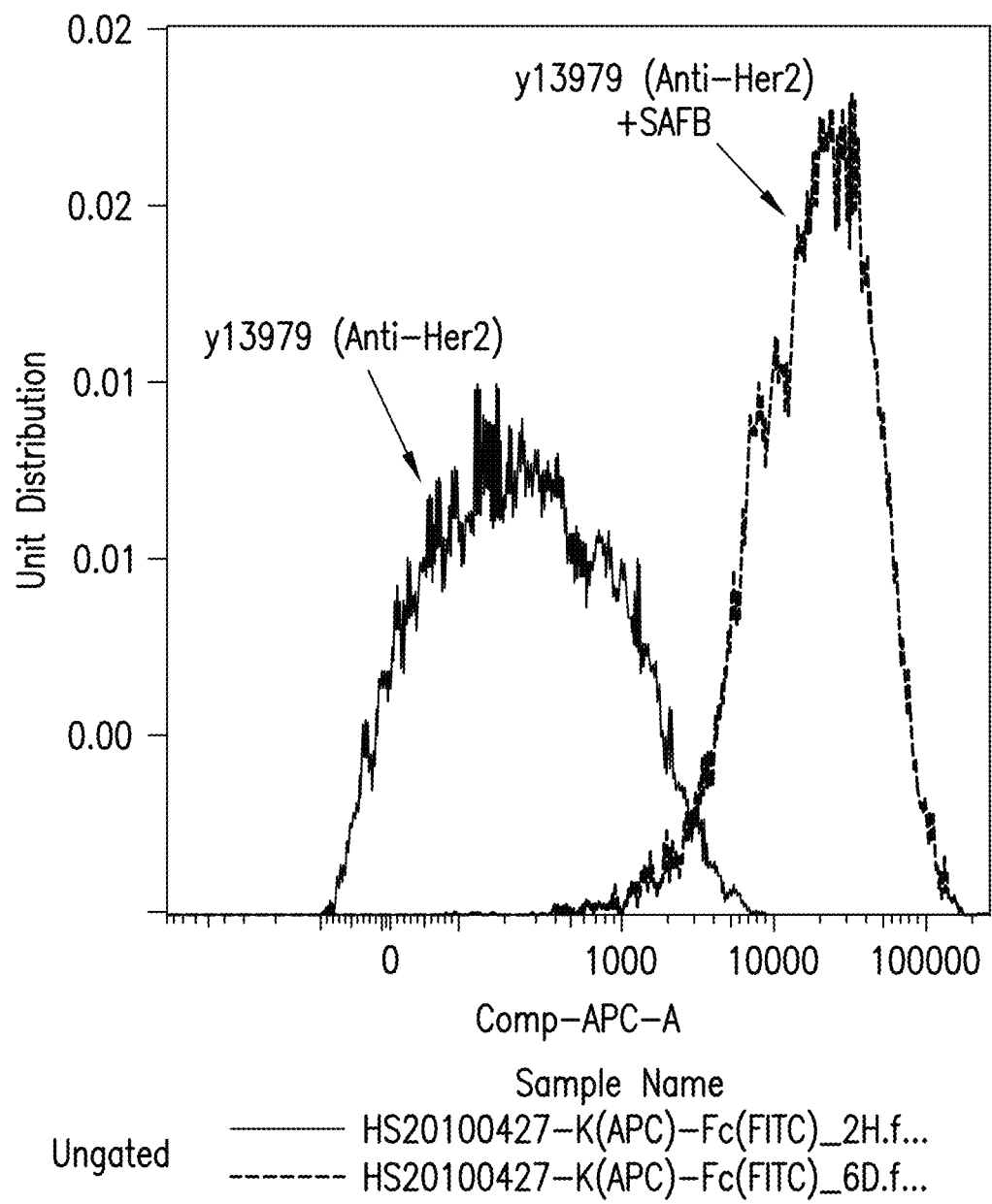
Figure 4C:
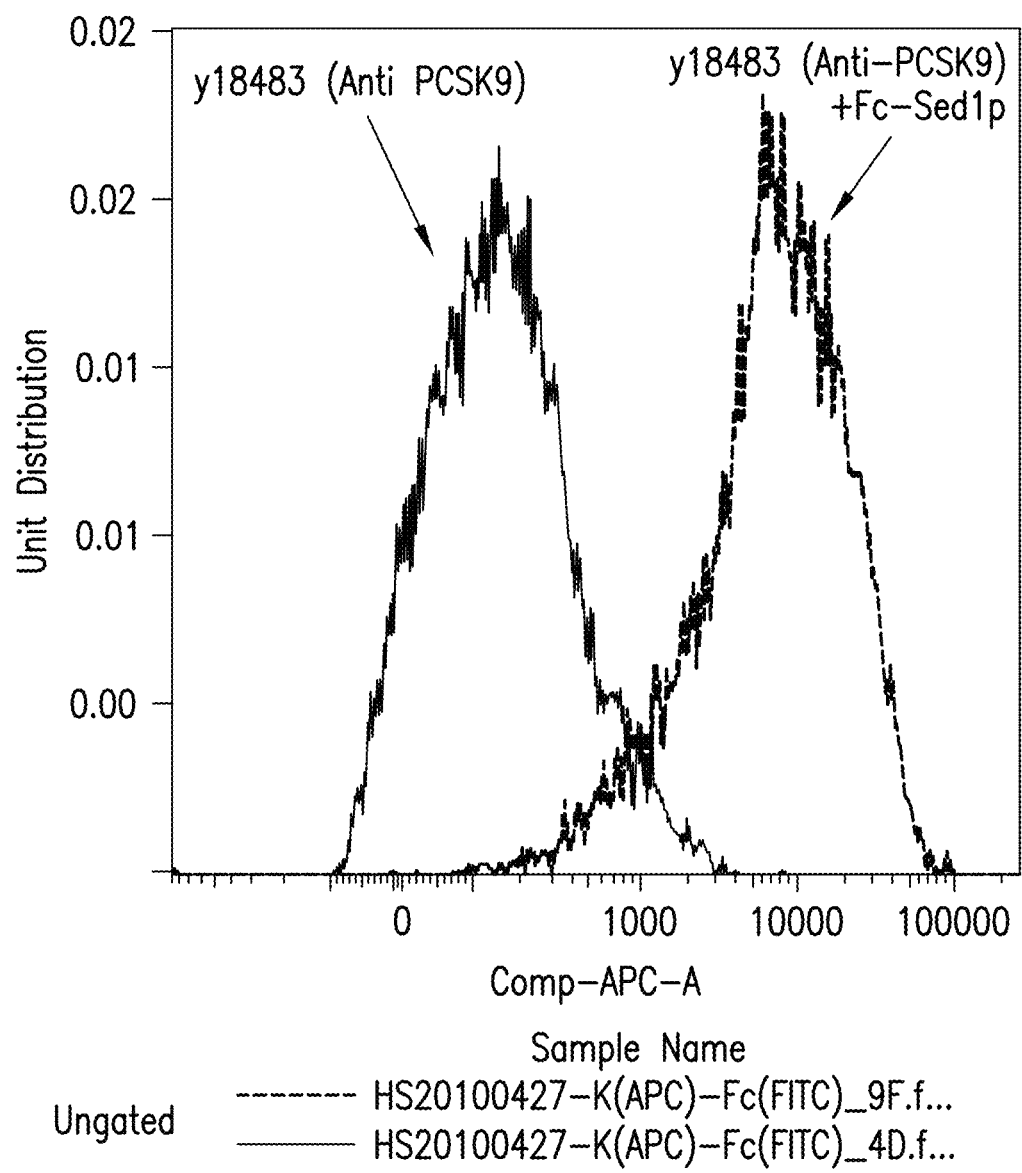

Flow cytometry analysis was conducted using the cells co-expressing Fc-Sed1p bait and anti-Her2, or Fc-Sed1p bait and anti-PCSK9. Controls were prepared in which an empty strain expressing Fc-Sed1p bait only or a strain that expressed full length antibody (H2+L2) without the Fc-Sed1p. Strains co-expressing anti-Her2 or anti-PCSK9 with the Fc-Sed1p bait were found to display significant levels of anti-Kappa binding while strains lacking the Fc-Sed1p bait showed background signal levels. In FIGS. 4A-4C, the fluorescent intensities from these experiments were compared. The figures show these different fluorescence intensities between the anti-Her2 displaying cells and the anti-PCSK9 displaying cells, and the parent strains that did not contain the Fc-Sed1p bait. It is noteworthy to mention that anti-Her2 displaying cells showed higher fluorescence intensity than the anti-PCSK9 displaying cells. These results were in congruence with what was known regarding expression levels of these two antibodies.

Figure 5:
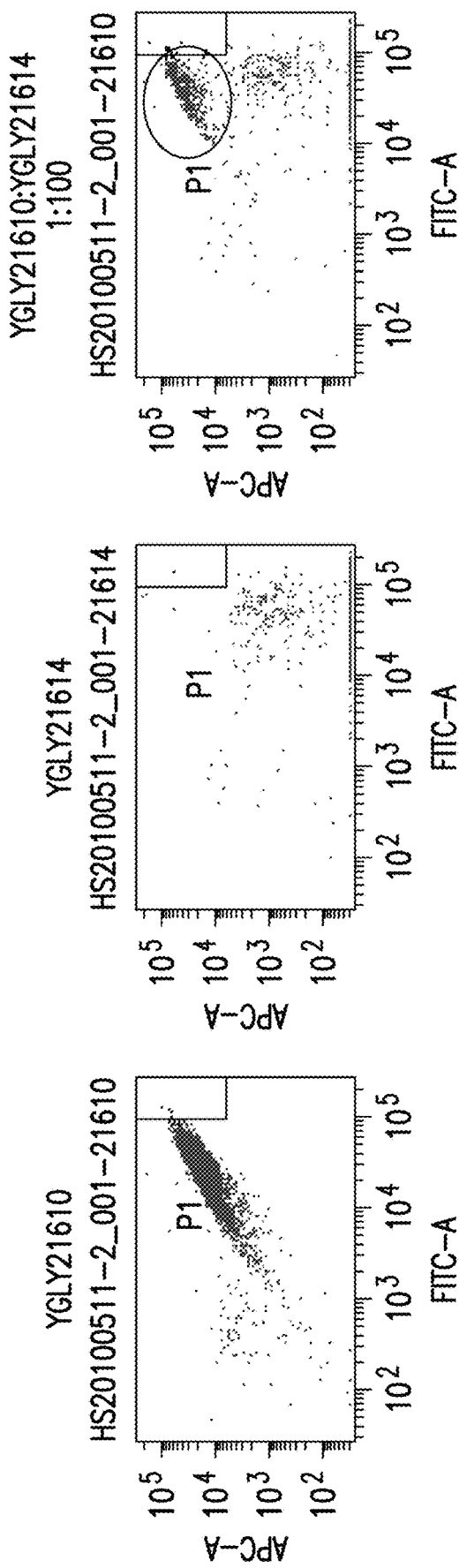
FIG. 5 shows FACS analysis of labeled *Pichia pastoris* yeast strains YGLY21610 and YGLY21614 displaying an Fc-Sed1p complexed with an anti-PCSK9 monovalent antibody fragment (H+L) or an anti-Her2 (H+L) monovalent antibody fragment. The cells were dually labeled with goat anti-human Fc Alexa 488, biotinylated PCSK9, and APC 635 labeled Streptavidin. The cells were analyzed separately (left and middle panels, respectively) and mixed together in a 1:00 ratio (right panel). The points representing the YGLY21610 cells in the right panel are circled.

To establish the utility of this method for separating antibody mixtures, fluorescence-activated cell sorting (FACS) of a mixture of cells displaying Fc-Sed1p anti-PCSK9 monovalent antibody fragment (H+L) (strain YGLY21610) and Fc-Sed1p anti-Her2 (H+L) (strain YGLY21614) was performed as follows. The cells displaying anti-PCSK9 (H+L) and cells displaying anti-Her2 (H+L) were mixed together in the following ratio 1:0; 0:1; and 1:100. Cells were dually labeled with goat anti-human Fc Alexa 488 and 100 nM biotinylated PCSK9 and APC 635 labeled Streptavidin. FIG. 5 shows that Fc-Sed1p/anti-PCSK9 (H+L) was able to bind biotinylated PCSK9 while Fc-Sed1p/anti-Her2 (H+L) was not. Both strains reacted with anti-human Fc Alexa 488 antibody. Two separate populations of cells were visible when cells from both cultures were mixed at a 1:100 ratio of Fc-Sed1p anti-PCSK9 displaying cells (circled) to Fc-Sed1p anti-Her2 displaying cells. The number of PCSK9 binders in this mixture was in agreement with the 1:100 ratio, thus lending further support for the robustness of this method in screening antibodies with desired antigen-binding.

The above experiments demonstrated that the Fc-Sed1p antibody display system can be used to display IgG monovalent antibody fragments (H+L) that retain specific antigen binding of their corresponding full antibody molecules (H2+L2) dimers. The next goal was to use this method to isolate and enrich for novel antibody molecules that can bind to any antigen of interest. To this end we took advantage of two recently constructed libraries. Library one was constructed by changing the sequence of the heavy chain of anti-PCSK9 antibody AX189 while marinating the original light chain sequence. This library had a diversity of about 2500 unique sequences and will be referred to as "BP550". The second library was generated by maintaining the original AX189 heavy chain sequence and changing the light chain sequence. This library contained about 4000 unique sequences and will be referred to as "BP551".

BP550 and BP551 were transformed as described previously into strain YGLY21605 (empty 5.0 strain carrying pGLY9008-expressing Fc-Sed1p) and plated out on YSD containing 300 micrograms per milliliter zeocin. Approximately, 50,000 colonies were obtained for each transformation, thus providing ample statistical coverage of all possible sequences in the libraries. The colonies resulting from transforming the two libraries were scraped off the solid media and inoculated separately in 250 mL shake flasks containing 50 mL of YSG liquid medium with 300 µ/mL zeocin. The cultures were passaged 3 times by re-inoculating 1 mL of each culture into the fresh selective liquid media (YSG+zeocin). The third passages were allowed to grow to saturation in YSG media and induced in 25 mL BMMY with PMTi inhibitor (PMTi4: L000001772; at a concentration of 1 micrograms/ml) overnight following the methods described in international patent publication no. WO2007/061631. Strains YGLY21610 (Fc-Sed1p anti-PCSK9 (AX189)) and YGLY21614 (Fc-Sed1p anti-Her2) were included as positive and negative controls, respectively.

After 24 hours of induction, each of the four cultures were grown to an optical density, at 600 nm, of 2. Pellets were collected by centrifugation and washed with 100 µL 1×PBS then labeled in 100 µL PBS containing anti-Kappa Alexa 488 and 100 nM of biotin-PCSK9. Mixtures were incubated at room temperature for 30 minutes then washed with 100 µL PBS solution. Cells were incubated at room temperature with APC 635 labeled Streptavidin in 100 µL PBS for 10 minutes and washed 2× in PBS and submitted for FACS.

Using the flow cytometer dot plots generated with YGLY21610 and YGLY21614 as boundaries to gate potential binders, clones from 100,000 cells of populations of both libraries, BP550 and BP551, were sorted in a FACS sorter and collected in 5 mL YSG media. Cultures were allowed to recover by shaking at room temperature for 5 days. Sorting round 1 pools were re-inoculated in 50 mL YSG liquid media and the same process was repeated to induce and label the cultures. Another round of sorting (round 2) was conducted on the round 1 pool and cells were collected as above and induced. To obtain single colonies, 1000 cells of both two-round sorted populations (BP550 and BP551) were plated out of solid media and were analyzed by Kappa ELISA and PCSK9 affinity ELISA to determine protein titer and binding affinities for PCSK9, respectively. Additionally, a yeast colony PCR amplification reaction was performed to amplify heavy chain and light chain genes of the round 2 clones which were submitted for DNA sequence analysis.

Figure 6:
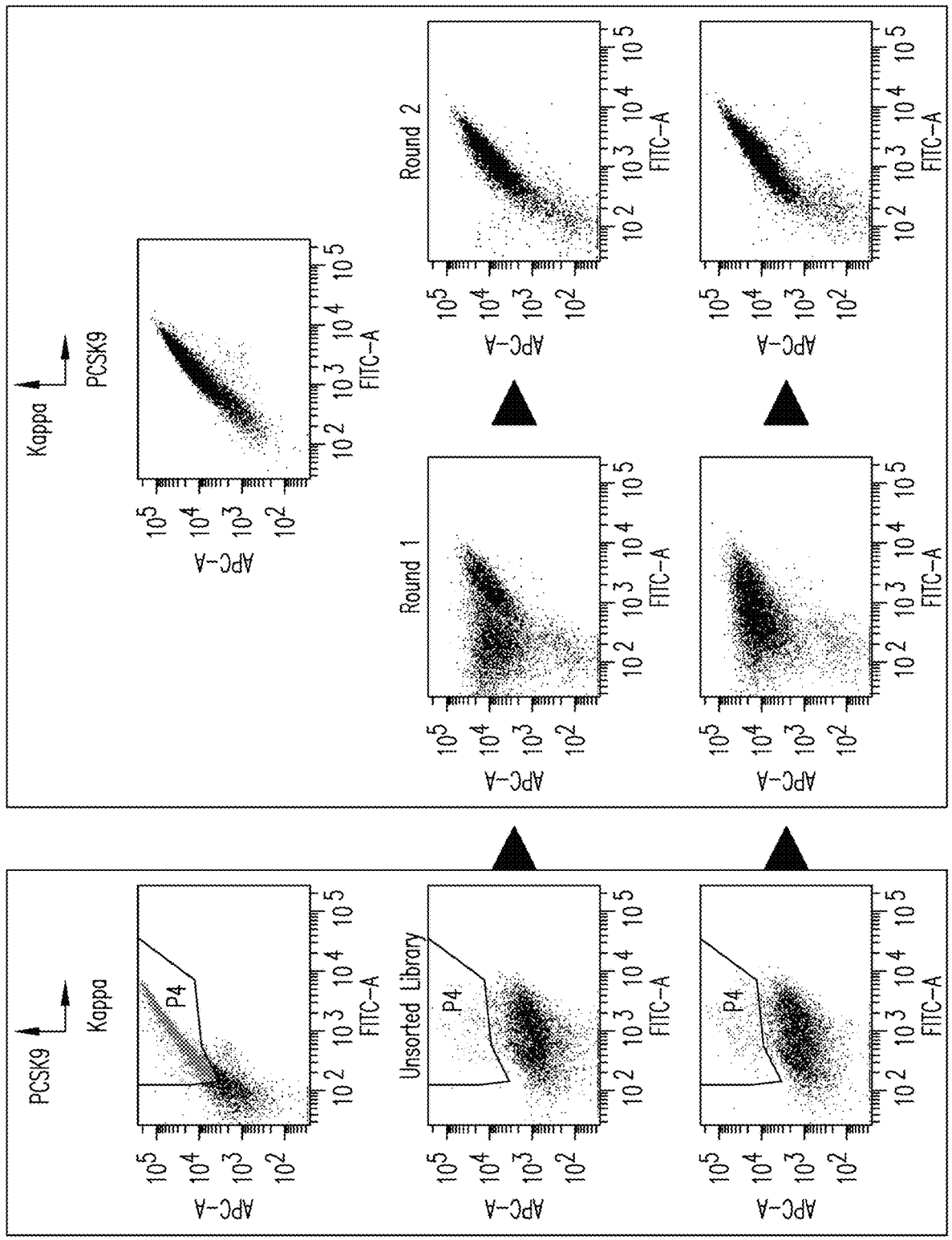
FIG. 6 shows FACS analysis of *Pichia pastoris* cells expressing the Fc-SEDT bait and; (1) anti-PCSK9 antibody AX189 heavy and light chains (Anti-PCSK9; AX189-Fc-Sed1p); or (2) AX189 light chain and heavy chain from the BP550 library (BP550-Fc-Sed1p); or (3) AX189 heavy chain and light chain from the BP551 library (BP551-Fc-Sed1p). The left panel shows data relating to unsorted strains containing the library, and the right panel shows data relating to cells containing the library that were sorted once or twice. FACS data relating to the control AX189 expressing cells are also shown.
Figure 8:
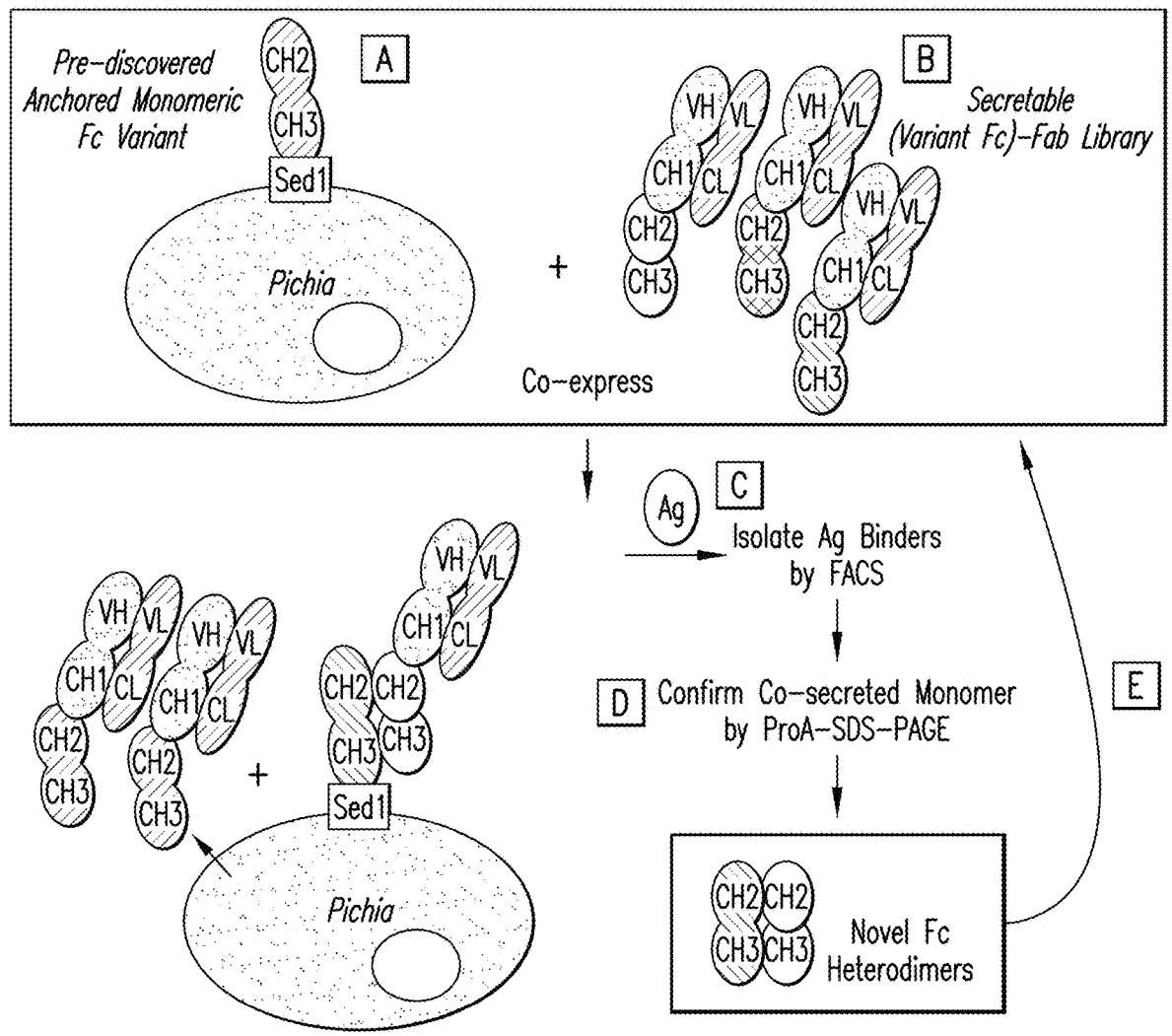
FIG. 8 shows the use of Fc-Sed1p display to discover novel heterodimeric Fc fragments for use in bispecifics and other applications. In this approach, an Fc mutant that lost its ability to homodimerize with self or heterodimerize with wild-type Fc can be displayed on a cell surface (A) and co-expressed with a library of H+L mutations where Fab region remains constant but CH2 and/or CH3 domains are mutated (B). Using surface display binding to Fab, cells that are positive for antigen binding can be isolated using FACS (C). Those cells will contain novel Fc variants that restore dimerization to the displayed bait-Fc. The culture supernatants can be assayed by SDS-PAGE to ensure monomeric secretion H+L containing the novel Fc (D). This exercise will result in identification of novel heterodimeric Fc pairs or partners that can be subject to subsequent engineering using the same assay (E).

As shown in FIG. 6, two rounds of sorting using biotinylated PCSK9 antigen resulted in significant enrichment of specific PCSK9 binders. The PCSK9 ELISA compared presorted library to round 2 sorted pools for both BP550 and BP551 (FIG. 7A and FIG. 7B). Round 2 sorted pools from both libraries contained a high percentage of binders over the presorted populations. DNA sequencing confirmed the enrichment for new anti-PCSK9 binding sequences.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. A method for making an antibody comprising culturing an isolated eukaryotic host cell in a growth medium under conditions allowing expression of an immunoglobulin light chain and an immunoglobulin heavy chain of said antibody, wherein the host cell is selected from the group consisting of a yeast and filamentous fungi; wherein the eukaryotic host cell comprises:
   (i) a first polynucleotide encoding said immunoglobulin light chain; and a second polynucleotide encoding said immunoglobulin heavy chain wherein the heavy chain is VH—CH1-CH2-CH3, each of said first and second polynucleotides operably associated with a promoter for expressing the immunoglobulin heavy and light chains; and
   (ii) a third polynucleotide encoding a bait comprising a heavy Fc immunoglobulin domain fused to a surface anchor polypeptide on the surface of said eukaryotic host cell, operably associated with a regulatable promoter for expressing the polynucleotide encoding the bait;
   wherein the Fc of said bait when expressed forms a complex with the Fc of the immunoglobulin heavy chain, which complex is displayed on the surface of the host cell; and
   wherein when expression of the bait is inhibited, said antibody is secreted from said eukaryotic host cell.

2. The method of claim 1, wherein the yeast is *Pichia*.

3. The method of claim 2, wherein the *Pichia* is *Pichia pastoris*.

4. The method of claim 1, wherein the yeast is *S. cerevisiae*.

5. The method of claim 1, wherein said antibody is isolated from said eukaryotic host cell and medium.

* * * * *